(12) United States Patent
Bourguignon et al.

(10) Patent No.: US 7,250,410 B2
(45) Date of Patent: Jul. 31, 2007

(54) CYCLIC NUCLEOTIDE PHOSPHODIESTERASE INHIBITORS, PREPARATION AND USES THEREOF

(75) Inventors: Jean-Jacques Bourguignon, Hipsheim (FR); Yan Lagouge, Strasbourg (FR); Claire Lugnier, Strasbourg (FR); Eveline Klotz, Mutzig (FR); Jean-Paul Macher, Bergholtz-Zell (FR); Pierre Raboisson, Eckbolsheim (FR); Dominique Schultz, Illkirch (FR)

(73) Assignee: Via Pharmaceuticals, Inc., San Francisco, CA (US)

( * ) Notice: Subject to any disclaimer, the term of this patent is extended or adjusted under 35 U.S.C. 154(b) by 279 days.

(21) Appl. No.: 10/479,000

(22) PCT Filed: Jun. 7, 2002

(86) PCT No.: PCT/FR02/01952

§ 371 (c)(1),
(2), (4) Date: Nov. 26, 2003

(87) PCT Pub. No.: WO02/098865

PCT Pub. Date: Dec. 12, 2002

(65) Prior Publication Data

US 2004/0152888 A1 Aug. 5, 2004

(30) Foreign Application Priority Data

Jun. 7, 2001 (FR) .................................. 01 07458

(51) Int. Cl.
*A61P 25/00* (2006.01)
*A61K 31/551* (2006.01)
*A61K 31/5513* (2006.01)
*C07D 243/00* (2006.01)

(52) U.S. Cl. ...................... 514/221; 540/504; 540/505; 540/507; 540/509; 540/510; 540/512; 540/514

(58) Field of Classification Search ................ 514/221; 540/504, 505, 507, 509, 510, 512, 514
See application file for complete search history.

(56) References Cited

U.S. PATENT DOCUMENTS

| 3,182,067 A | 5/1965 | Fryer et al. | 260/296 |
| 3,398,159 A | 8/1968 | Berger et al. | 260/326.5 |
| 3,631,029 A | 12/1971 | Yamamoto et al. | 260/239.3 |

FOREIGN PATENT DOCUMENTS

| DE | 20 17 060 | 10/1970 |
| DE | 17 95 832 | 4/1976 |
| EP | 0 065 229 | 11/1982 |
| EP | 0 387 618 | 9/1990 |
| EP | 0 552 665 | 7/1993 |
| FR | 7 666 M | 2/1970 |
| FR | 2 085 645 | 12/1971 |
| FR | 2 273 547 | 1/1976 |
| GB | 972963 | 10/1964 |
| WO | WO 97/28135 | 8/1997 |
| WO | WO 97/34878 | 9/1997 |
| WO | WO 00/79263 | 12/2000 |
| WO | WO 02/51838 | 7/2002 |

OTHER PUBLICATIONS

Sotiriadis et al, "New synthesis of substituted 3,5-dihydro-4H-2,3-benzodiazepin-4-ones", CS 81:152197 & J. Heterocycl. Chem. (1974), 11(3), pp. 401-403, XP-002191653.

Flammang, "2,3-Benzodiazepines: 2-amino-3-isoquinolinones from ring contraction of 4-oxo-2,3-benzodiazepines", CS 93:167330 & C.R. Seances Acad. Scie., Ser. C (1980), 290(17), pp. 349-351, XP-002191655.

Bogza et al, "Recyclization of 2-oxobenzo[c]pyrrole[3,2-e]pyrylium perchlorates by acid hydrazides", CS 124:343246 & Khim. Geterotsikl Soedin, (1995), (12), pp. 1691-1692, XP-002191656.

Bogza et al, "Synthesis of benzo[c]pyrylium salts from 2-(3,4-dimethoxyphenyl)succinic acid derivatives and their transformations", CS 126:7948 & Zh. Org. Khim. (1996), 32(4), pp. 596-603, XP-002191657.

"3H-2,3-Benzodiazepine-5-acetamide, 3-(aminocarbonyl)-4,5-dihydro-7,8-dimethoxy-1-methyl-4-oxo-N-phenyl", Chemcats 2001-2609076 and Ambinter: Exploratory Library, May 31, 2001.

"4H-2,3—Benzodiazepin-4-one, 3-[2-(diethylamino)ethyl]-3,5-dihydro-7,8-dimethoxy-1-methyl-(9CI)", CA 48202-61-5 Registry, 1984.

Shimamoto et al, "Pharmacological Screening of New Benzodiazepines in Mice", Journal of the Takeda Research Laboratories, Osaka, JP, vol. 29, No. 1, 1970, pp. 134-144.

Gatta et al, "Derivatives of 2,3-Benzodiazepine", Il Farmaco, Rome IT, vol. 40, No. 12, 1985, pp. 942-955.

Sotiriadis et al, "New Synthesis of Substituted 3,5-Dihydro-4H-2,3-benzodiazepine-4-ones", J. Heterocycl. Chem. (1974), 11(3), pp. 401-403.

(Continued)

*Primary Examiner*—Brenda Coleman

(57) ABSTRACT

The invention concerns novel benzodiazepine derivatives and their uses in the field of therapeutics particularly for treating pathologies involving the activity of a cyclic nucleotide phosphodiesterase. It also concerns methods for preparing them and novel synthesis intermediates. The inventive compounds more particularly correspond to general formula (I):

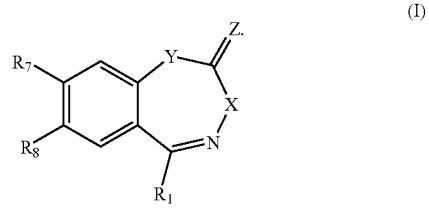

18 Claims, 2 Drawing Sheets

OTHER PUBLICATIONS

Flammang et al, "2,3-Benzodiazepine systems. II. 4-Oxo-3,5-dihydro(4H)-2,3-benzodiazepines. Synthesis and pharmacological study", CA 85:46605 & Eur. J. Med. Chem.—Chim. Ther. (1976), 11(1), pp. 83-87.

Flammang, "2,3—Benzodiazepines: 2-amino-3-isoquinolinones from ring contraction of 4-oxo-2,3-benzodiazepines", CS 93:167330 & C.R. Seances Acad. Sci., Ser. C (1980) 290(17), pp. 349-351.

De Sarro et al, "Synthesis and anticonculsant activity of new 2,3-benzodiazepines as AMPA receptor antagonists", Farmaco, Society Chimica Italiana, Pavia, IT., vol. 54, No. 3, 1999, pp. 178-187.

Nagarajan et al, "Derivatives of 3,5-Dihydro-4H-benzo [2,3] diazepin-4-one", J Med. Chem. (1972), 15(10), pp. 1091-1092.

Bogza et al, "Synthesis of benzo[c]pyrylium salts from 2-(3,4-dimethoxyphenyl)succinic acid derivatives and their transformations", CA 126:7948 & Zhurnal Organicheskoi Khimii (1996), 32(4), pp. 596-603.

Chimirri et al, "1-Aryl-3,5-dihydro-4H-2,3-benzoidiazepin-4-ones: Novel AMPA Receptor Antagonists", J. Med. Chem. (1997), 40(8), pp. 1258-1269.

Chimirri et al, "3,5-Dihydro-4H-2,3-benzodiazepine-4-thiones: A New Class of AMPA Receptor Antagonists", J. Med. Chem. (1998), 41(18), pp. 3409-3416.

CA BAS 0340144 and "AsinEx Compound Collection", May 10, 2001, Asinex, 6 Shukinskaya Street, Moscow, 123182, Russia.

Sugasawa et al, "1-Azacycloalkyl-1,4-benzodiazepin-2-ones with antianxiety-antidepressent actions", Journal of Medical Chemistry, American Chemical Society, Washington, US, vol. 28, No. 6, 1985, pp. 699-707.

Vassilev et al, "Cell-based screening approach for antitumor drug leads which exploits sensitivity differences between normal and cancer cells: identification of two novel cell-cycle inhibitors", CA 136:226419 & Anti-Cancer Drug Design (2001), 16(1). pp. 7-17.

Bogatskii et al, "Predicting the pharmacological activities of tranquilizers which are 1,4-diazepin-2-one derivatives", CS 95:180658 & USP. Kvantovoi Khim. Kvantovoi Biol., Tr. Mezhdunar. Konf. (1980), Meeting Date 1978, vol. 2, 33-40. Editor(s): Petrov, E.G.; Loewdin, Per Olov, Zener, M. Publisher: Izd, Naukova Dumka, Kiev, USSR.

Combs et al, "Phosphoryl chloride-induced ring contraction of 1,4-benzodiazepinones to (chloromethyl)quinazolines" Journal of Heterocyclic Chemistry (1986), 23(4), pp. 1263-1264.

Ivanov, "1-4-Benzodiazepines. V. Synthesis of 7,8-dimethoxy-5-[6,',7'-dimethoxyisoquinolyl]-1,3-dihydro-2H-1,4b enzodiazepin-2-ones", CS 86:189880 & Khim.-Farm. Zh. (1977), 11(2), pp. 32-36.

Compton et al, The Lancet, vol. 358, Jul. 28, 2001, pp. 265-270.

Houslay et al, DDT, vol. 10, No. 22, Nov. 2005, pp. 1503-1519.

O'Donnell et al, TRENDS in Pharmacological Sciences, vol. 25, No. 3, Mar. 2004, pp. 158-163.

Teixeira et al, TiPS, May 1997, vol. 18, pp. 164-170.

Barad et al, Proc. Natl. Acad. Sci., vol. 95, Dec. 1998, pp. 15020-15025.

Torphy et al, Am. J. Respir. Crit. Care Med., vol. 157, 1998, pp. 351-370.

CYCLIC NUCLEOTIDE PHOSPHODIESTERASE INHIBITORS, PREPARATION AND USES THEREOF

This application is the US national phase of international application PCT/FR02/01952 filed 7 Jun. 2002 which designated the U.S. and claims benefit of FR 0107458, dated 7 Jun. 2001, the entire contents of each of which is hereby incorporated by reference.

The invention concerns novel benzodiazepine derivatives and their uses in the field of therapeutics particularly for treating pathologies involving the activity of a cyclic nucleotide phosphodiesterase. It also concerns methods for preparing them and novel synthesis intermediates.

The compounds whose synthesis is described in the present invention are novel and possess very interesting pharmacological properties: they are inhibitors of cyclic nucleotide phosphodiesterases and more particularly of cAMP-phosphodiesterase type 4 (PDE4) and, as such, they have very interesting therapeutic applications.

The functions of most tissues are modulated by endogenous substances such as hormones, transmitters, etc. or by exogenous substances. The biological effect of some of these substances is transmitted inside the cell by enzymatic effectors, such as adenylate cyclase or guanylate cyclase. Stimulation of such enzymes results in an elevation of intracellular levels of cyclic AMP (cAMP) or cyclic GMP (cGMP), second messengers involved in regulating many cellular activities. These cyclic nucleotides are degraded by a family of enzymes—the phosphodiesterases (PDE)—comprising at least seven groups. One of them, PDE4, is present in many different tissues (heart, brain, vascular or tracheobronchial smooth muscle, etc.) and specifically hydrolyzes cyclic AMP.

By slowing down the degradation of cyclic AMP, the PDE4 inhibitors increase or maintain cAMP levels in cells, and find use particularly in the treatment of inflammatory disorders or pathologies of tracheobronchial smooth muscle, by combining both an anti-inflammatory effect and smooth muscle relaxation.

The applicant has now demonstrated that certain benzodiazepines or benzodiazepinones have inhibitory effects on cyclic nucleotide phosphodiesterases, particularly inhibition of PDE4. The invention also describes novel compounds which show potent inhibitory activity towards PDE4, and preferentially display an excellent selectivity profile with respect to other PDE isoforms, in particular a weak action on PDE3. Moreover, the preferred compounds according to the invention possess anti-inflammatory properties that may be used in this respect to treat central or peripheral nervous system disorders, and advantageously are devoid of hypotensive or emetic effects.

More particularly, the invention has as its object compounds represented by general formula (I)

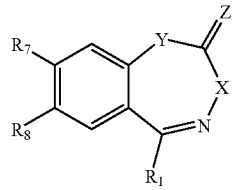

(I)

wherein:
either X represents an $NR_4$ group and Y represents a $CR_6R_6'$ group, $R_4$, $R_6$ and $R_6'$ being defined hereinafter,
or X represents a $CR_4R_4'$ group and Y represents an $NR_6$ group, $R_4$, $R_4'$ and $R_6$ being defined hereinafter, Z represents an oxygen or sulfur atom.

$R_1$ is a $(C_1-C_{12})$alkyl, $(C_3-C_6)$cycloalkyl, $(C_6-C_{18})$aryl, $(C_6-C_{18})$aryl$(C_1-C_4)$alkyl, $(C_1-C_{12})$alkyl$(C_6-C_{18})$aryl group, $(C_5-C_{18})$heterocycle, aromatic or not, containing 1 to 3 heteroatoms, or an $OR_2$, $SR_2$ or $NR_2R_3$ group in which (i) $R_2$ and $R_3$, independently of each other, are selected in the group consisting of a hydrogen atom, a $(C_1-C_6)$alkyl, $(C_3-C_6)$cycloalkyl, $(C_6-C_{12})$aryl group, and a $(C_5-C_{12})$heterocycle, aromatic or not, containing 1 to 3 heteroatoms or, (ii) $R_2$ and $R_3$ together form a linear or branched hydrocarbon having from 2 to 6 carbon atoms, possibly containing one or more double bonds and/or possibly interrupted by an oxygen, sulfur or nitrogen atom;

$R_4$ and $R_4'$, which are the same or different, represent a $(C_3-C_6)$cycloalkyl, unsubstituted $(C_6-C_{18})$aryl, $(C_6-C_{18})$aryl$(C_1-C_4)$alkyl, $(C_1-C_{12})$alkyl$(C_6-C_{18})$aryl group or a $(C_5-C_{18})$heterocycle, aromatic or not, containing 1 to 3 heteroatoms, and, when X is the group $CR_4R_4'$, $R_4$ and $R_4'$, which are the same or different, are selected in the group consisting of the hydrogen atom and a $(C_1-C_{12})$alkyl, $(C_6-C_{18})$aryl, $(C_2-C_6)$alkenyl, $(C_2-C_6)$alkynyl, $NO_2$, $CF_3$, $CN$, $NR'R''$, $SR'$, $OR'$, $COOR'$, $CONR'R''$ and $NHCOR'R''$ group, $R'$ and $R''$, independently of each other, being selected in the group consisting of the hydrogen atom, a $(C_1-C_6)$alkyl, $(C_1-C_6)$alkoxy, $(C_3-C_6)$cycloalkyl, $(C_6-C_{12})$aryl group, and a $(C_5-C_{12})$heterocycle, aromatic or not, containing 1 to 3 heteroatoms;

$R_6$ and $R_6'$, which are the same or different, are selected in the group consisting of the hydrogen atom, $(C_1-C_6)$alkyl, $(C_6-C_{18})$aryl, $(C_6-C_{18})$aryl$(C_1-C_4)$alkyl, $(C_1-C_{12})$alkyl$(C_6-C_{18})$aryl, preferably a phenyl, benzyl group and a $(C_1-C_6)$alkylphenyl group;

$R_7$ and $R_8$, independently of each other, are selected in the group consisting of the hydrogen atom, a $(C_1-C_{12})$alkyl group and an $OR_2$ group, $R_2$ being defined hereinabove, with the condition that $R_7$ and $R_8$ do not both represent a hydrogen atom, or $R_7$ and $R_8$ together form a linear or branched hydrocarbon chain having from 2 to 6 carbon atoms, possibly containing one or more double bonds and/or possibly interrupted by an oxygen, sulfur or nitrogen atom;

the alkyl, alkenyl, alkynyl, alkylaryl, aralkyl, cycloalkyl, aryl, phenyl, heterocycle groups and the hydrocarbon chain defined hereinabove possibly being substituted by one or more substituents, which are the same or different, preferably selected in the group consisting of a halogen atom, a $(C_1-C_{12})$alkyl, $(C_6-C_{18})$aryl, $(C_2-C_6)$alkenyl, $(C_2-C_6)$alkynyl, heterocycle, OH, =O, $NO_2$, $NR'R''$, CN, $CF_3$, COR', COOR', $(C_1-C_6)$alkoxy, (di)$(C_1-C_6)$alkylamino, NHCOR' and CONR'R'' group, in which R' and R'' are defined as hereinabove, and the salts thereof.

The invention also concerns pharmaceutical compositions comprising one or more compounds represented by general formula (I) such as defined hereinabove, and a pharmaceutically acceptable vehicle or excipient.

The invention further relates to the use of compounds represented by general formula (I) such as defined hereinabove for preparing a pharmaceutical composition designed to inhibit a cyclic nucleotide phosphodiesterase, particularly phosphodiesterase 4 (PDE4). More particularly, the invention concerns the use of the hereinabove compounds for treating pathologies involving a deregulation of intracellular cyclic AMP levels.

In the context of the invention, the term "alkyl" designates a linear or branched hydrocarbon group advantageously containing from 1 to 12 carbon atoms, such as methyl, ethyl, propyl, isopropyl, butyl, isobutyl, tert-butyl, pentyl, neopentyl, n-hexyl, n-decyl, n-dodecyl, etc. $C_1$–$C_4$ groups are preferred. The alkyl groups may be substituted by an aryl group such as defined hereinafter, in which case it is called an arylalkyl group. Benzyl and phenethyl are specific examples of arylalkyl groups.

The term "cycloalkyl" denotes a cyclic hydrocarbon system, which may advantageously contain from 3 to 6 carbon atoms and be mono- or poly-cyclic. Examples include cyclopropyl and cyclohexyl groups in particular.

"Aryl" groups are mono-, bi- or tri-cyclic aromatic hydrocarbon systems, preferably monocyclic or bicyclic aromatic hydrocarbons containing from 6 to 18 carbon atoms, even more preferably 6 carbon atoms. Examples include phenyl, naphthyl and biphenyl groups.

"Heterocycle" groups denote hydrocarbon systems, aromatic or not, containing one or more cyclic heteroatoms. Preferably they are cyclic hydrocarbon systems containing from 5 to 18 carbon atoms and one or more cyclic heteroatoms, particularly from 1 to 3 or 4 cyclic heteroatoms chosen from among N, O and S. Preferred aromatic heterocyclic groups (heteroaryls) include in particular thienyl, benzothienyl, benzofuryl, naphthyl, pyridyl, pyrimidinyl, pyridazinyl, isoquinolinyl, morpholino, thiazolyl, furyl, pyranyl, pyrrolyl, 2H-pyrrolyl, imidazolyl, benzymidazolyl, pyrazolyl, isothiazolyl, isoxazolyl and indolyl groups. Among the preferred non-aromatic heterocyclic groups, piperidinyl and pyrrolidinyl groups are particular examples.

The aryl and heterocycle groups may be substituted by an OH function, an alkyl, alkenyl or alkynyl group. An aryl or a heterocycle substituted by an alkyl group is called an alkylaryl or alkylheterocycle group. Examples of alkylaryl groups include in particular tolyl, mesythyl and xylyl. An aryl or a heterocycle substituted by an alkenyl group is referred to as an alkenylaryl or alkenylheterocycle group. Examples of alkenylaryl groups include in particular the cinnamyl group. An aryl or a heterocycle substituted by an alkynyl group is called an alkynylaryl or alkynylheterocycle group.

The aryl and heterocycle groups may also be substituted by a group independently chosen from among aryl or heterocycle groups, themselves possibly substituted by one or more substituents chosen preferably from among a halogen atom and an $NO_2$, CN, $CF_3$, OR', COR', COOR', alkoxy, NHCOR' or CONR'R" group, R' and R" being defined as hereinabove.

Specific examples of aryl and heterocycle groups substituted by an aryl or heterocycle group are the benzothienyl, benzofuryl, furylphenyl, benzyloxynaphthyl, pyridylphenyl, phenylphenyl and thienylphenyl groups. As noted, the hereinabove groups may be substituted. In this respect one example is the phenyl groups substituted by a phenyl group itself substituted by a halogen atom, an $NO_2$, $CF_3$, methoxy or methyl group.

"Alkenyl" groups are linear or branched hydrocarbon functions containing one or more double bonds, such as for instance the allyl group. They advantageously contain from 2 to 6 carbon atoms and, preferably, 1 or 2 double bonds. Alkenyl groups may be substituted by an aryl group such as defined hereinabove, in which case it is called an arylalkenyl group.

"Alkynyl" groups are linear or branched hydrocarbon functions containing one or more triple bonds, such as for instance the 3-(benzyloxy)prop-1-ynyl, phenylethynyl, prop-2-ynyl and tert-butyl-prop-2-ynylcarbamate groups. They advantageously contain from 2 to 6 carbon atoms and, preferably, 1 or 2 double bonds. Alkynyl groups may be substituted by an aryl group such as defined hereinabove, in which case it is called an arylalkynyl group.

"Alkoxy" groups correspond to the alkyl and cycloalkyl groups defined hereinabove linked to the nucleus by means of an —O-(ether) bond. Methoxy and ethoxy groups are especially preferred.

"Halogen" designates a fluorine, chlorine, bromine or iodine atom.

"Heteroatom" is an atom chosen from among O, N and S.

More particularly, the invention has as its object the compounds represented by general formula (I) hereinabove wherein X is a $CR_4R_4'$ group and Y is an $NR_6$ group.

Such compounds are represented by formula (II) below:

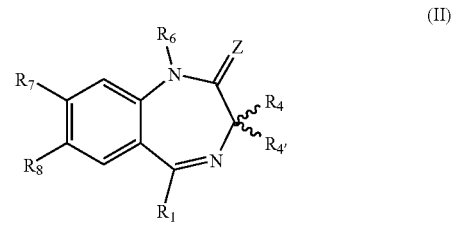

(II)

wherein $R_1$, $R_4$, $R_{4'}$, $R_6$, $R_7$ and $R_8$ are defined as hereinabove. Such compounds possess inhibitory properties that are especially marked and preferential for phosphodiesterase 4.

A further specific object of the invention concerns compounds having general formula (I) hereinabove wherein X is the $NR_4$ group and Y is the $CR_6R_6'$ group. Such compounds are represented by formula (III) below:

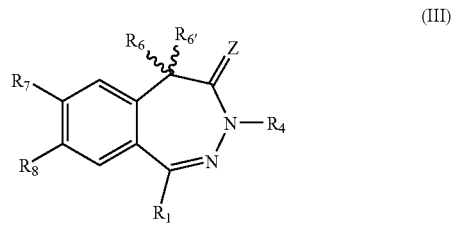

(III)

wherein $R_1$, $R_4$, $R_6$, $R_{6'}$, $R_7$ and $R_8$ are defined as hereinabove. Such compounds display especially marked and preferential inhibition of phosphodiesterase 4.

Particular compounds according to the invention are those in which:

Z is the oxygen atom and/or $R_7$ and $R_8$, independently of each other, represent an $OR_2$ group wherein $R_2$ is a $(C_1$–$C_6)$alkyl group, preferably an ethyl or methyl group, and/or $R_7$ represents a hydrogen atom and $R_8$ represents a halogen atom or vice versa, and/or $R_7$ and $R_8$ each represent an ethoxy or methoxy group, and/or $R_6$ and $R_6'$, which are the same or different, represent the hydrogen atom or a $(C_1$–$C_6)$alkyl group, and/or $R_6$ represents the hydrogen atom or a $(C_1$–$C_6)$alkyl group and $R_6'$ is the hydrogen atom, and/or X is the $CR_4R_4'$ group wherein $R_4$ and $R_4'$, which are the same or different, represent a $(C_1-C_{12})$alkyl or $(C_6-C_{18})$aryl$(C_1-C_4)$alkyl group, possibly substituted by one or more substituents, which are the same or different, chosen from among a halogen atom and an OH, =O, $NO_2$, $NH_2$, CN, $CF_3$, COR', COOR', $(C_1-C_6)$ alkoxy, (di)$(C_1-C_6)$alkylamino, NHCOR' or CONR'R" group, in which R' and R" are defined as hereinabove, and/or $R_4'$ is the hydrogen atom, and/or X is the $CR_4R_4'$ group in which $R_4$ represents a $(C_1-C_{12})$ alkyl or $(C_6-C_{18})$aryl$(C_1-C_4)$alkyl group, more particularly benzyl, possibly substituted by one or more substituents, which are the same or different, selected in the group consisting of a halogen atom and an OH, =O, $NO_2$, $NH_2$, CN, $CF_3$, COR', COOR', $(C_1-C_6)$ alkoxy, (di)$(C_1-C_6)$alkylamino, NHCOR' and CONR'R" group, in which R' and R" are defined as hereinabove, and $R_4'$ is the hydrogen atom, and/or X is the $CR_4R_4$ group in which $R_4$ and $R_4'$ are a hydrogen atom, and/or $R_1$ is a $(C_6-C_{18})$aryl group, more particularly phenyl, $(C_6-C_{18})$aryl$(C_1-C_4)$alkyl, more particularly benzyl, $(C_1-C_{12})$alkyl$(C_6-C_{18})$aryl or a $(C_5-C_{18})$heterocycle, aromatic or not, containing 1 to 3 heteroatoms, possibly substituted.

A specific family of compounds is represented by compounds having general formula (II) such as defined hereinabove wherein $R_4$ and $R_4'$ represent the hydrogen atom.

A specific family of compounds is represented by compounds having the general formula (II) such as defined hereinabove wherein $R_7$ and $R_8$ together form a hydrocarbon chain, such as for example the chain —O—$CH_2$—$CH_2$—O—.

Another family comprises compounds represented by general formula (I) wherein X is the $CR_4R_4'$ group, Y is the $NR_6$ group, Z is the oxygen atom, $R_7$ and $R_8$ represent, independently of each other, an $OR_2$ group in which $R_2$ is a $(C_1-C_6)$alkyl group, $R_6$ represents the hydrogen atom or a $(C_1-C_6)$alkyl group and $R_4$ and $R_4'$ represent the hydrogen atom.

Another family comprises compounds represented by general formula (I) wherein X is the $CR_4R_4'$ group, Y is the $NR_6$ group, Z is the oxygen atom, $R_7$ represents a hydrogen atom and $R_8$ represents a halogen atom or vice versa.

Another family comprises compounds represented by general formula (I) wherein X is the $NR_4$ group, Y is the $CR_6R_6'$ group, Z is the oxygen atom, $R_7$ and $R_8$ represent, independently of each other, an $OR_2$ group in which $R_2$ is a $(C_1-C_6)$alkyl group, $R_6$ and $R_{16}$, which are the same or different, represent the hydrogen atom or a $(C_1-C_6)$alkyl group and $R_4$ represents a $(C_1-C_{12})$alkyl or $(C_6-C_{18})$aryl $(C_1-C_4)$alkyl group, possibly substituted by one or more substituents, which are the same or different, chosen from among a halogen atom and an OH, =O, $NO_2$, $NH_2$, CN, $CF_3$, COR', COOR', $(C_1-C_6)$alkoxy, (di)$(C_1-C_6)$alkylamino, NHCOR' or CONR'R"group, in which R' and R" are defined as hereinabove.

Another family comprises compounds having general formula (I) wherein X is the $CR_4R_4'$ group, Y is the $NR_6$ group, Z is the oxygen atom, $R_7$ represents a hydrogen atom and $R_8$ represents an $OR_2$ function in which $R_2$ is a $(C_1-C_6)$ alkyl group.

In a preferred manner, in the compounds represented by general formula (I), (II) and (III) according to the invention and in the specific families described hereinabove, the groups $R_7$ and $R_8$ represent, independently of each other, a methoxy or ethoxy group, more preferably they both represent a methoxy or ethoxy group.

In a preferred manner, in the compounds represented by general formula (I), (II) and (III) according to the invention and in the specific families described hereinabove, the $R_6$ and $R_6'$ groups, which are the same or different, represent a hydrogen atom or a methyl, ethyl or n-propyl group. In an especially advantageous variant, in the compounds represented by general formula (I), (II) and (III) according to the invention and in the specific families described hereinabove the $R_6$ group represents a hydrogen atom or a methyl, ethyl or n-propyl group and the $R_6'$ group is a hydrogen atom. In another particularly advantageous variant, in the compounds represented by general formula (I), (II) and (III) according to the invention and in the specific families described hereinabove, the $R_6$ and $R_6'$ groups, which are the same or different, represent a methyl or ethyl group.

In the compounds represented by general formula (I), (II) and (III) according to the invention and in the specific families described hereinabove, preferred examples are those wherein $R_4'$ is the hydrogen atom and, when $R_4$ is not the hydrogen atom, $R_4$ more preferably represents a methyl, ethyl, n-propyl, n-dodecyl or benzyl group.

As noted, in the compounds represented by general formula (I), (II) and (III) according to the invention and in the specific families described hereinabove, $R_1$ advantageously represents a $(C_6-C_{18})$aryl, $(C_6-C_{18})$aryl$(C_1-C_4)$alkyl, $(C_1-C_{12})$alkyl$(C_6-C_{18})$aryl group or a $(C_5-C_{18})$heterocycle, aromatic or not, containing 1 to 3 heteroatoms, said group or heterocycle possibly being substituted.

According to a first variant of the invention, $R_1$ is a phenyl group, particularly a substituted phenyl, preferably a phenyl group substituted by:
  (a) one or more halogen atoms, particularly chlorine, bromine or iodine, preferably chlorine, or
  (b) one or more OR' groups, particularly methoxy or ethoxy, or
  (c) a COR' group, particularly acetyl, or
  (d) a trifluoromethyl group, or
  (e) an alkyl or alkynyl group, for example heptinyl, or
  (f) an aryl group or heterocycle, particularly a phenyl, furyl, pyridyl or thienyl group, said aryl group or heterocycle itself possibly being substituted by one or more groups chosen preferably from among groups (a)–(e).

According to another specific variant of the invention, $R_1$ is an aromatic heterocycle, particularly naphthyl, thienyl, furyl, indolyl or pyridyl, possibly substituted by one or more groups chosen preferably from among the groups (a)–(f) hereinabove. In a specific variant, $R_1$ is a naphthyl group possibly substituted by one or more groups chosen from among the groups (a)–(f) hereinabove.

According to a further specific variant of the invention, $R_1$ is a non-aromatic heterocycle, particularly piperidinyl or isoquinolinyl, possibly substituted by one or more groups chosen preferably from among the groups (a)–(f) hereinabove.

Specific examples of $R_1$ groups that are particularly advantageous for carrying out the invention are the 4-chlorophenyl, 3,4-dichlorophenyl, 2-naphthyl, 2-benzo[b]thienyl, 4-(2-furyl)phenyl, 3-pyridyl and 3-trifluoromethylphenyl groups.

The following compounds are especially preferred:
7,8-dimethoxy-1-(2-naphthyl)-3-methyl-3,5-dihydro-4H-2,3-benzodiazepin-4-one.
1-(4-chlorophenyl)-7,8-dimethoxy-3-methyl-3,5-dihydro-4H-2,3-benzodiazepin-4-one.

1-(2-benzo[b]thienyl)-7,8-dimethoxy-3-methyl-3,5-dihydro-4H-2,3-benzodiazepin-4-one.
1-[4-(2-furyl)phenyl]-7,8-dimethoxy-3-methyl-3,5-dihydro-4H-2,3-benzodiazepin-4-one.
1-(2-benzo[b]thienyl)-7,8-diethoxy-3-methyl-3,5-dihydro-4H-2,3-benzodiazepin-4-one.
1-(2-benzo[b]thienyl)-7,8-diethoxy-5-ethyl-3-methyl-3,5-dihydro-4H-2,3-benzodiazepin-4-one.
1-(4-chlorophenyl)-7,8-diethoxy-3-methyl-3,5-dihydro-4H-2,3-benzodiazepin-4-one.
5-(4-chlorophenyl)-7,8-dimethoxy-1-methyl-1,3-dihydro-1,4-benzodiazepin-2-one.

Other particular compounds in the context of the invention are the following compounds:

7,8-dimethoxy-1-phenyl-3,5-dihydro-4H-2,3-benzodiazepin-4-one.
1-(2-benzo[b]thienyl)-7,8-diethoxy-3,5-dihydro-4H-2,3-benzodiazepin-4-one.
1-(2-benzo[b]thienyl)-7,8-diethoxy-5-n-propyl-3,5-dihydro-4H-2,3-benzodiazepin-4-one.
7,8-dimethoxy-3-methyl-1-(1-naphthyl)-3,5-dihydro-4H-2,3-benzodiazepin-4-one.
3-benzyl-7,8-dimethoxy-1-phenyl-3,5-dihydro-4H-2,3-benzodiazepin-4-one.
3-dodecyl-7,8-dimethoxy-1-phenyl-3,5-dihydro-4H-2,3-benzodiazepin-4-one.
7,8-dimethoxy-3-(12-methoxy-12-oxododecyl)-1-phenyl-3,5-dihydro-4H-2,3-benzodiazepin-4-one.
3-ethyl-7,8-dimethoxy-1-phenyl-3,5-dihydro-4H-2,3-benzodiazepin-4-one.
7,8-dimethoxy-1-phenyl-3-n-propyl-3,5-dihydro-4H-2,3-benzodiazepin-4-one.
1-(4-iodophenyl)-7,8-dimethoxy-3-methyl-3,5-dihydro-4H-2,3-benzodiazepin-4-one.
7,8-dimethoxy-1-[4-(2-methoxyphenyl)phenyl]-3-methyl-3,5-dihydro-4H-2,3-benzodiazepin-4-one.
7,8-dimethoxy-1-[4-(3-methoxyphenyl)phenyl]-3-methyl-3,5-dihydro-4H-2,3-benzodiazepin-4-one.
1-[4-(3-acetylphenyl)phenyl]-7,8-dimethoxy-3-methyl-3,5-dihydro-4H-2,3-benzodiazepin-4-one.
7,8-dimethoxy-3-methyl-1[4-(3-pyridyl)phenyl]-3,5-dihydro-4H-2,3-benzodiazepin-4-one.
1-[4-(4-acetylphenyl)phenyl]-7,8-dimethoxy-3-methyl-3,5-dihydro-4H-2,3-benzodiazepin-4-one.
1-[4-(3-acetamidophenyl)phenyl]-7,8-dimethoxy-3-methyl-3,5-dihydro-4H-2,3-benzodiazepin-4-one.
1-(4-bromophenyl)-7,8-dimethoxy-3-methyl-3,5-dihydro-4H-2,3-benzodiazepin-4-one.
7,8-dimethoxy-1-[4-(4-methoxyphenyl)phenyl]-3-methyl-3,5-dihydro-4H-2,3-benzodiazepin-4-one.
1-{4-[3-(trifluoromethyl)phenyl]phenyl}-7,8-dimethoxy-3-methyl-3,5-dihydro-4H-2,3-benzodiazepin-4-one.
7,8-dimethoxy-3-methyl-1-[4-(2-methylphenyl)phenyl]-3,5-dihydro-4H-2,3-benzodiazepin-4-one.
7,8-dimethoxy-3-methyl-1-[4-(3-methylphenyl)phenyl]-3,5-dihydro-4H-2,3-benzodiazepin-4-one.
7,8-dimethoxy-3-methyl-1-[4-(4-methylphenyl)phenyl]-3,5-dihydro-4H-2,3-benzodiazepin-4-one.
1-[4-(4-chlorophenyl)phenyl]-7,8-dimethoxy-3-methyl-3,5-dihydro-4H-2,3-benzodiazepin-4-one.
7,8-dimethoxy-3-methyl-1-[4-(2-thienyl)phenyl]-3,5-dihydro-4H-2,3-benzodiazepin-4-one.
1-{4-[3,5-bis-(trifluoromethyl)phenyl]phenyl}-7,8-dimethoxy-3-methyl-3,5-dihydro-4H-2,3-benzodiazepin-4-one.
1-[4-(heptyn-1-yl)phenyl]-7,8-dimethoxy-3-methyl-3,5-dihydro-4H-2,3-benzodiazepin-4-one.
7,8-dimethoxy-3-methyl-1-[4-(3-nitrophenyl)phenyl]-3,5-dihydro-4H-2,3-benzodiazepin-4-one.
1-(2-benzo[b]thienyl)-7,8-diethoxy-3-ethyl-3,5-dihydro-4H-2,3-benzodiazepin-4-one.
1-(2-benzo[b]thienyl)-7,8-diethoxy-3-methyl-5-n-propyl-3,5-dihydro-4H-2,3-benzodiazepin-4-one.
3,5-dibenzyl-7,8-dimethoxy-1-phenyl-3,5-dihydro-4H-2,3-benzodiazepin-4-one.
7,8-dimethoxy-1-phenyl-3-(3-hydroxypropyl)-3,5-dihydro-4H-2,3-benzodiazepin-4-one.
7,8-dimethoxy-1-methyl-5-phenyl-1,3-dihydro-1,4-benzodiazepin-2-one.
7,8-dimethoxy-5-(3,4-dimethoxyphenyl)-1-methyl-1,3-dihydro-1,4-benzodiazepin-2-one.
5-(2-benzo[b]thienyl)-7,8-dimethoxy-1-methyl-1,3-dihydro-1,4-benzodiazepin-2-one.
5-(2-benzo[b]furyl)-7,8-dimethoxy-1-methyl-1,3-dihydro-1,4-benzodiazepin-2-one.
5-(2-furyl)-7,8-dimethoxy-1-methyl-1,3-dihydro-1,4-benzodiazepin-2-one.
5-(4-acetylphenyl)-7,8-dimethoxy-1-methyl-1,3-dihydro-1,4-benzodiazepin-2-one.
7,8-dimethoxy-1-methyl-5-(2-thienyl)-1,3-dihydro-1,4-benzodiazepin-2-one.
7,8-dimethoxy-5-(3-methoxyphenyl)-1-methyl-1,3-dihydro-1,4-benzodiazepin-2-one.
7,8-dimethoxy-5-(2-methoxyphenyl)-1-methyl-1,3-dihydro-1,4-benzodiazepin-2-one.
5-(5-indolyl)-7,8-dimethoxy-1-methyl-1,3-dihydro-1,4-benzodiazepin-2-one.
5-(6-benzyloxy-2-naphthyl)-7,8-dimethoxy-1-methyl-1,3-dihydro-1,4-benzodiazepin-2-one.
7,8-dimethoxy-5-(6-methoxy-2-naphthyl)-1-methyl-1,3-dihydro-1,4-benzodiazepin-2-one.
5-(2-indolyl)-7,8-dimethoxy-1-methyl-1,3-dihydro-1,4-benzodiazepin-2-one.
7,8-dimethoxy-1-methyl-5-(piperidin-1-yl)-1,3-dihydro-1,4-benzodiazepin-2-one.
7,8-dimethoxy-1-methyl-5-(2-methylphenyl)-1,3-dihydro-1,4-benzodiazepin-2-one.
7,8-dimethoxy-5-(4-methoxyphenyl)-1-methyl-1,3-dihydro-1,4-benzodiazepin-2-one.
5-(1,1'-biphenyl-3-yl)-7,8-dimethoxy-1-methyl-1,3-dihydro-2H-1,4-benzodiazepin-2-one.
5-(4-bromophenyl)-7,8-dimethoxy-1-methyl-1,3-dihydro-2H-1,4-benzodiazepin-2-one.
5-(4-bromophenyl)-7,8-dimethoxy-1,3-dihydro-2H-1,4-benzodiazepin-2-one.
8-bromo-5-(4-bromophenyl)-1,3-dihydro-2H-1,4-benzodiazepin-2-one.
7-iodo-5-[3-(trifluoromethyl)phenyl]-1,3-dihydro-2H-1,4-benzodiazepin-2-one.
7-methoxy-5-[3-(trifluoromethyl)phenyl]-1,3-dihydro-2H-1,4-benzodiazepin-2-one.
7,8-dimethoxy-5-phenyl-1,3-dihydro-2H-1,4-benzodiazepin-2-one.
1-benzyl-7,8-dimethoxy-5-phenyl-1,3-dihydro-2H-1,4-benzodiazepin-2-one.
7,8-diethoxy-5-phenyl-1,3-dihydro-2H-1,4-benzodiazepin-2-one.
1-ethyl-7,8-dimethoxy-5-phenyl-1,3-dihydro-2H-1,4-benzodiazepin-2-one.
7,8-dimethoxy-5-phenyl-1-propyl-1,3-dihydro-2H-1,4-benzodiazepin-2-one.
7,8-diethoxy-1-methyl-5-phenyl-1,3-dihydro-2H-1,4-benzodiazepin-2-one.

7,8-diethoxy-1-ethyl-5-phenyl-1,3-dihydro-2H-1,4-benzodiazepin-2-one.

ethyl (7,8-diethoxy-2-oxo-5-phenyl-2,3-dihydro-1H-1,4-benzodiazepin-1-yl)acetate.

10-phenyl-2,3,6,8-tetrahydro-7H-[1,4]dioxino[2,3-h][1,4]benzodiazepin-7-one.

1-benzyl-7,8-diethoxy-5-phenyl-1,3-dihydro-2H-1,4-benzodiazepin-2-one.

7,8-diethoxy-3-methyl-5-phenyl-1,3-dihydro-2H-1,4-benzodiazepin-2-one.

3-benzyl-7,8-diethoxy-5-phenyl-1,3-dihydro-2H-1,4-benzodiazepin-2-one.

1-ethyl-7,8-dihydroxy-5-phenyl-1,3-dihydro-2H—1,4-benzodiazepin-2-one.

5-(4-bromophenyl)-1-ethyl-7,8-dimethoxy-1,3-dihydro-2H-1,4-benzodiazepin-2-one.

5-(3-bromophenyl)-7,8-dimethoxy-1-methyl,3-dihydro-2H-1,4-benzodiazepin-2-one.

5-(3-bromophenyl)-7,8-dimethoxy-1,3-dihydro-2H-1,4-benzodiazepin-2-one.

5-(3-bromophenyl)-1-ethyl-7,8-dimethoxy-1,3-dihydro-2H-1,4-benzodiazepin-2-one.

5-{4-[3-(benzyloxy)prop-1-ynyl]phenyl}-1-ethyl-7,8-dimethoxy-1,3-dihydro-2H-1,4-benzodiazepin-2-one.

tert-butyl 3-[4-(1-ethyl-7,8-dimethoxy-2-oxo-2,3-dihydro-1H-1,4-benzodiazepin-5-yl)phenyl]prop-2-ynyl carbamate.

5-(1,1'-biphenyl-4-yl)-1-ethyl-7,8-dimethoxy-1,3-dihydro-2H-1,4-benzodiazepin-2-one.

3-(4-chlorobenzyl)-1-ethyl-7,8-dimethoxy-5-phenyl-1,3-dihydro-2H-1,4-benzodiazepin-2-one.

1-ethyl-7,8-dimethoxy-5-[4-(phenylethynyl)phenyl]-1,3-dihydro-2H-1,4-benzodiazepin-2-one.

3-allyl-1-ethyl-7,8-dimethoxy-5-phenyl-1,3-dihydro-2H-1,4-benzodiazepin-2-one.

1-ethyl-7,8-dimethoxy-5-phenyl-3-prop-2-ynyl-1,3-dihydro-2H-1,4-benzodiazepin-2-one.

1-ethyl-7,8-dimethoxy-5-[4-(2-phenylethyl)phenyl]-1,3-dihydro-2H-1,4-benzodiazepin-2-one.

ethyl (1-ethyl-7,8-dimethoxy-2-oxo-5-phenyl-2,3-dihydro-1H-1,4-benzodiazepin-3-yl)acetate.

1-ethyl-7,8-dimethoxy-5-[3-(phenylethynyl)phenyl]-1,3-dihydro-2H-1,4-benzodiazepin-2-one.

5-(2-bromophenyl)-7,8-dimethoxy-1,3-dihydro-2H-1,4-benzodiazepin-2-one.

(1-ethyl-7,8-dimethoxy-2-oxo-5-phenyl-2,3-dihydro-1H-1,4-benzodiazepin-3-yl)acetonitrile.

3-(2-bromobenzyl)-1-ethyl-7,8-dimethoxy-5-phenyl-1,3-dihydro-2H-1,4-benzodiazepin-2-one.

3-(4-bromobenzyl)-1-ethyl-7,8-dimethoxy-5-phenyl-1,3-dihydro-2H-1,4-benzodiazepin-2-one.

3-[(3-bromophenyl)(hydroxy)methyl]-1-ethyl-7,8-dimethoxy-5-phenyl-1,3-dihydro-2H-1,4-benzodiazepin-2-one.

3-(3-bromobenzyl)-1-ethyl-7,8-dimethoxy-5-phenyl-1,3-dihydro-2H-1,4-benzodiazepin-2-one.

3-(1,1'-biphenyl-4-ylmethyl)-1-ethyl-7,8-dimethoxy-5-phenyl-1,3-dihydro-2H-1,4-benzodiazepin-2-one.

3-(1-benzyl-4-hydroxypiperidin-4-yl)-1-ethyl-7,8-dimethoxy-5-phenyl-1,3-dihydro-2H-1,4-benzodiazepin-2-one.

3-(4-chlorobenzyl)-1-ethyl-7,8-dimethoxy-5-phenyl-1,3-dihydro-2H-1,4-benzodiazepin-2-one.

3-[(1-ethyl-7,8-dimethoxy-2-oxo-5-phenyl-2,3-dihydro-1H-1,4-benzodiazepin-3-yl)methyl]benzonitrile.

3-benzyl-1-ethyl-7,8-dimethoxy-5-phenyl-1,3-dihydro-2H-1,4-benzodiazepin-2-one.

1-ethyl-7,8-dimethoxy-3-(2-methoxybenzyl)-5-phenyl-1,3-dihydro-2H-1,4-benzodiazepin-2-one.

3-[(1-ethyl-7,8-dimethoxy-2-oxo-5-phenyl-2,3-dihydro-1H-1,4-benzodiazepin-3-yl)methyl]benzamide.

3-[3-(aminomethyl)benzyl]-1-ethyl-7,8-dimethoxy-5-phenyl-1,3-dihydro-2H-1,4-benzodiazepin-2-one.

3-(1,1'-biphenyl-3-ylmethyl)-1-ethyl-7,8-dimethoxy-5-phenyl-1,3-dihydro-2H-1,4-benzodiazepin-2-one.

3-benzyl-7,8-diethoxy-1-ethyl-5-phenyl-1,3-dihydro-2H-1,4-benzodiazepin-2-one.

2-(1-ethyl-7,8-dimethoxy-2-oxo-5-phenyl-2,3-dihydro-1H-1,4-benzodiazepin-3-yl)acetamide.

3-(2-chlorobenzyl)-1-ethyl-7,8-dimethoxy-5-phenyl-1,3-dihydro-2H-1,4-benzodiazepin-2-one.

1-ethyl-7,8-dimethoxy-3-(2-methylbenzyl)-5-phenyl-1,3-dihydro-2H-1,4-benzodiazepin-2-one.

8-ethoxy-7-methoxy-5-phenyl-1,3-dihydro-2H-1,4-benzodiazepin-2-one.

8-ethoxy-7-methoxy-1-methyl-5-phenyl-1,3-dihydro-2H-1,4-benzodiazepin-2-one.

1-ethyl-7,8-dimethoxy-5-phenyl-3-[3-(trifluoromethyl)benzyl]-1,3-dihydro-2H-1,4-benzodiazepin-2-one.

1-ethyl-7,8-dimethoxy-3-(3-methoxybenzyl)-5-phenyl-1,3-dihydro-2H-1,4-benzodiazepin-2-one.

1-ethyl-7,8-dimethoxy-3-(4-methylbenzyl)-5-phenyl-1,3-dihydro-2H-1,4-benzodiazepin-2-one.

3-[1,2-bis(4-bromophenyl)ethyl]-1-ethyl-7,8-dimethoxy-5-phenyl-1,3-dihydro-2H-1,4-benzodiazepin-2-one.

3-[(8-ethoxy-7-methoxy-1-methyl-2-oxo-5-phenyl-2,3-dihydro-1H-1,4-benzodiazepin-3-yl)methyl]benzonitrile.

2-[(8-ethoxy-7-methoxy-1-methyl-2-oxo-5-phenyl-2,3-dihydro-1H-1,4-benzodiazepin-3-yl)methyl]benzonitrile.

3-[(8-ethoxy-7-methoxy-1-methyl-2-oxo-5-phenyl-2,3-dihydro-1H-1,4-benzodiazepin-3-yl)methyl]benzamide.

8-methoxy-5-phenyl-1,3-dihydro-2H-1,4-benzodiazepin-2-one.

7-methoxy-5-phenyl-1,3-dihydro-2H-1,4-benzodiazepin-2-one.

7-methoxy-1-methyl-5-phenyl-1,3-dihydro-2H-1,4-benzodiazepin-2-one.

8-methoxy-1-methyl-5-phenyl-1,3-dihydro-2H-1,4-benzodiazepin-2-one.

7,8-dimethoxy-5-(4-fluorophenyl)-1-methyl-1,3-dihydro-2H-1,4-benzodiazepin-2-one.

7,8-dimethoxy-1-methyl-5-(4-pyridyl)-1,3-dihydro-2H-1,4-benzodiazepin-2-one.

7,8-dimethoxy-1-methyl-5-(3,5 bis trifluoromethylphenyl)-1,3-dihydro-2H-1,4-benzodiazepin-2-one.

7,8-dimethoxy-5-(4-N,N-dimethylaminophenyl)-1-methyl-1,3-dihydro-2H-1,4-benzodiazepin-2-one.

7,8-dimethoxy-1-methyl-5-[(E)-2-phenylethenyl]-1,3-dihydro-2H-1,4-benzodiazepin-2-one.

7,8-dimethoxy-1-methyl-5-(2-phenylethynyl)-1,3-dihydro-2H-1,4-benzodiazepin-2-one.

7,8-dimethoxy-1-methyl-5-(N-tetrahydro-1,2,3,4-isoquinolyl)-1,3-dihydro-2H-1,4-benzodiazepin-2-one.

7,8-dimethoxy-3-isobutyl-5-phenyl-1,3-dihydro-2H-1,4-benzodiazepin-2-one.

3-benzyl-7,8-dimethoxy-5-phenyl-1,3-dihydro-2H-1,4-benzodiazepin-2-one.

7,8-dimethoxy-3-methyl-5-phenyl-1,3-dihydro-2H-1,4-benzodiazepin-2-one.

7,8-dimethoxy-3-(1H-imidazol-4-ylmethyl)-5-phenyl-1,3-dihydro-2H-1,4-benzodiazepin-2-one.

7,8-dimethoxy-3-(1H-indol-3-ylmethyl)-5-phenyl-1,3-dihydro-2H-1,4-benzodiazepin-2-one.

7,8-dimethoxy-3-(2-methylthioethyl)-5-phenyl-1,3-dihydro-2H-1,4-benzodiazepin-2-one.

(S) 3-benzyl-7,8-dimethoxy-5-phenyl-1,3-dihydro-2H-1,4-benzodiazepin-2-one.

(S)-3-benzyl-7,8-dimethoxy-1-methyl-5-phenyl-1,3-dihydro-2H-1,4-benzodiazepin-2-one.

7,8-dimethoxy-1-methyl-5-(2-phenylethyl)-1,3-dihydro-2H-1,4-benzodiazepin-2-one.

(7,8-dimethoxy-5-phenyl-2-oxo-2,3-dihydro-1H-1,4-benzodiazepin-3-yl)benzyl(S)-butylcarbamate.

(S)-3-(4-aminobutyl)-7,8-dimethoxy-5-phenyl-1,3-dihydro-2H-1,4-benzodiazepin-2-one.

(S)-N-[4-(7,8-dimethoxy-2-oxo-5-phenyl-2,3-dihydro-1H-1,4-benzodiazepin-3-yl)butyl]acetamide.

N-[4-(7,8-dimethoxy-2-oxo-5-phenyl-2,3-dihydro-1H-1,4-benzodiazepin-3-yl)butyl]guanidinium(S)-bis trifluoroacetate.

7,8-dimethoxy-1-ethyl-3-(2-nitrobenzyl)-5-phenyl-1,3-dihydro-2H-1,4-benzodiazepin-2-one.

3-(3,5-dibromobenzyl)-7,8-dimethoxy-1-ethyl-5-phenyl-1,3-dihydro-2H-1,4-benzodiazepin-2-one.

7,8-dimethoxy-3-(diphenylhydroxymethyl)-1-ethyl-5-phenyl-1,3-dihydro-2H-1,4-benzodiazepin-2-one.

7,8-dimethoxy-1-ethyl-3-(E-3-phenylpropen-2yl)-5-phenyl-1,3-dihydro-2H-1,4-benzodiazepin-2-one.

7,8-dimethoxy-1-ethyl-3-(2-aminobenzyl)-5-phenyl-1,3-dihydro-2H-1,4-benzodiazepin-2-one.

7,8-dimethoxy-1-(2-hydroxyethyl)-5-phenyl-1,3-dihydro-2H-1,4-benzodiazepin-2-one.

3-(2-cyanobenzyl)-7,8-dimethoxy-1-ethyl-5-phenyl-1,3-dihydro-2H-1,4-benzodiazepin-2-one.

N-[2-(7,8-dimethoxy-2-oxo-5-phenyl-2,3-dihydro-1H-1,4-benzodiazepin-3-yl)benzyl]acetamide.

3-(2-aminomethylbenzyl)-7,8-dimethoxy-1-ethyl-5-phenyl-1,3-dihydro-2H-1,4-benzodiazepin-2-one.

[(7,8-dimethoxy-1-ethyl-2-oxo-2,3-dihydro-1H-1,4-benzodiazepin-3-yl)benz-2-yl]carboxamide.

N-[2-(7,8-dimethoxy-2-oxo-5-phenyl-2,3-dihydro-1H-1,4-benzodiazepin-3-yl)benzyl]methylacetamide.

7,8-dimethoxy-3,5-diphenyl-1,3-dihydro-2H-1,4-benzodiazepin-2-one.

3-(2,4-dichlorobenzyl)-7,8-dimethoxy-1-ethyl-5-phenyl-1,3-dihydro-2H-1,4-benzodiazepin-2-one.

3-(2,5-dichlorobenzyl)-7,8-dimethoxy-1-ethyl-5-phenyl-1,3-dihydro-2H-1,4-benzodiazepin-2-one.

3,5-diphenyl-8-ethoxy-7-methoxy-1,3-dihydro-2H-1,4-benzodiazepin-2-one.

3-benzyl-8-ethoxy-7-methoxy-5-phenyl-1,3-dihydro-2H-1,4-benzodiazepin-2-one.

3-benzyl-8-ethoxy-1-ethyl-7-methoxy-5-phenyl-1,3-dihydro-2H-1,4-benzodiazepin-2-one.

3,5-diphenyl-8-ethoxy-1-ethyl-7-methoxy-1,3-dihydro-2H-1,4-benzodiazepin-2-one.

5-phenyl-7-ethoxy-8-methoxy-1,3-dihydro-2H-1,4-benzodiazepin-2-one.

The compounds according to the invention may be in the form of salts, particularly acid or base salts, preferably compatible with pharmaceutical use. Among the pharmaceutically acceptable acids, non-limiting examples include hydrochloric, hydrobromic, sulfuric, phosphoric, acetic, trifluoroacetic, lactic, pyruvic, malonic, succinic, glutaric, fumaric, tartric, maleic, citric, ascorbic, methane or ethane sulfonic, camphoric acids, etc. Among the pharmaceutically acceptable bases, non-limiting examples include sodium hydroxide, potassium hydroxide, triethylamine, tert-butylamine, etc.

The invention also has as its object a composition comprising a compound such as defined hereinabove and a pharmaceutically acceptable vehicle or excipient.

The compounds or compositions of the invention may be administered in different ways and in different forms. For instance, they may be administered systemically, by the oral route, by inhalation or by injection, such as for example by the intravenous, intramuscular, subcutaneous, transdermal, intra-arterial route, etc., the intravenous, intramuscular, subcutaneous, oral and inhalation routes being preferred.

For injections, the compounds are generally prepared in the form of liquid suspensions, which may be injected through syringes or by infusion, for instance. In this respect, the compounds are generally dissolved in pharmaceutically compatible saline, physiologic, isotonic, buffered solutions, and the like, known to those skilled in the art. For instance, the compositions may contain one or more agents or vehicles chosen from among dispersives, solubilizers, stabilizers, preservatives, and the like. Agents or vehicles that may be used in the liquid and/or injectable formulations comprise in particular methylcellulose, hydroxymethylcellulose, carboxymethylcellulose, polysorbate 80, mannitol, gelatin, lactose, vegetable oils, acacia, and the like.

The compounds may also be administered in the form of gels, oils, tablets, suppositories, powders, capsules, gelules, aerosols, and the like, possibly by means of pharmaceutical forms or devices allowing extended and/or delayed release. For this type of formulation, an agent such as cellulose, carbonates or starches is advantageously used.

It is understood that the injection rate and/or injected dose may be adapted by those skilled in the art according to the patient, the pathology, the mode of administration, etc. Typically, the compounds are administered at doses ranging from 0.1 µg to 100 mg/kg of body weight, more generally from 0.01 to 10 mg/kg, typically between 0.1 and 10 mg/kg. Furthermore, repeated injections may be given, as the case may be. In addition, in the case of chronic treatments delayed or sustained release systems may be advantageous.

The compounds according to the invention may act on different cyclic nucleotide phosphodiesterases, particularly PDE4, and may also be active on certain PDE subtypes.

For instance, four subtypes of PDE4 have been identified, named PDE4A–D. The compounds according to the invention may display specific biological properties according to the PDE4 subtype affected. Thus, the inventive compounds may be (selective) inhibitors of PDE-4A, PDE-4B, PDE-4C and/or PDE-4D. The compounds of the invention which inhibit PDE-4B are especially interesting for treating the inflammatory component of depression, psychiatric disorders or obesity, for example.

The PDE4 inhibitor compounds according to the invention are of particular interest for treating pathologies involving bronchial inflammation and relaxation, and more particularly asthma and chronic obstructive pulmonary disease, but also other pathologies such as rhinitis, acute respiratory distress syndrome, allergy, skin disorders, such as dermatitis, psoriasis, rheumatoid arthritis, autoimmune diseases, different forms of sclerosis (particularly multiple sclerosis), dyskinesias, glomerulonephritis, osteoarthritis, cancer, septic shock, AIDS or obesity.

The compounds of the invention are also of particular interest for treating inflammatory disorders of the central nervous system, such as, more specifically, for treating an inflammatory disorder chosen from among depression, schizophrenia, bipolar disorder, attention deficit disorder, fibromyalgia, epilepsy, Alzheimer's disease, Parkinson's disease, amyotrophic lateral sclerosis, multiple sclerosis, and Lewy body dementia.

The invention also finds use for treating inflammatory disorders such as Crohn's disease.

A particular object of the invention therefore concerns using the compounds such as described hereinabove for preparing a medicament for treating inflammatory disorders of the nervous system, particularly central, which are chronic or acute.

A more particular object concerns using the compounds such as described hereinabove for preparing a medicament for treating inflammatory disorders of the central nervous system (e.g., neuroinflammation).

In the context of the invention, the term treatment denotes either a preventive or a curative treatment, which may be used alone or in combination with other agents or treatments. Moreover, it may be a treatment of chronic or acute disorders.

The present invention also has as its object the use of the described compounds as anti-inflammatory agents, for instance for treating osteoporosis or rheumatoid arthritis.

The preferred compounds of the invention advantageously display potent inhibitory activity towards one or more PDE4 subtypes. The preferred compounds of the invention further display an advantageous selectivity profile, particularly weak activity with respect to PDE3.

The compounds of the invention may be prepared from commercially available products, by using a combination of chemical reactions known to those skilled in the art.

Figure 1:
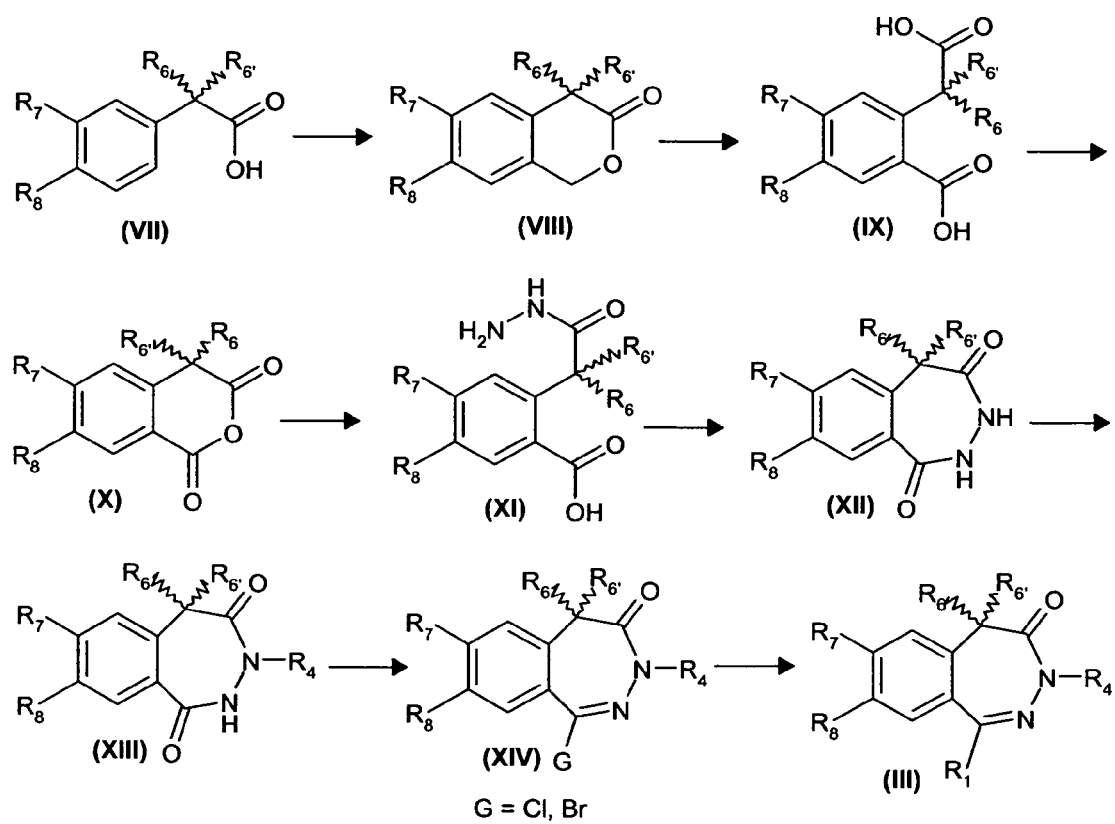
FIGS. 1 and 2 depict the synthetic reaction routes of compounds represented by formula (I).

In this respect, according to a first method, the compounds represented by general formula (III) according to the invention wherein Z is an oxygen atom may be obtained from a compound represented by formula (VI)

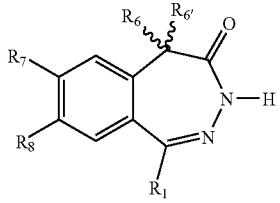

(VI)

wherein $R_1$ $R_6$, $R_{6'}$, $R_7$ and $R_8$ are defined as hereinabove, by reaction with an alkyl halogenide in the presence of potassium carbonate at room temperature. Preferably, the reaction is carried out in a polar aprotic solvent, DMF for example.

The compounds represented by general formula (VI) may be prepared by a method comprising the following steps:

a) reacting a compound represented by general formula (IV)

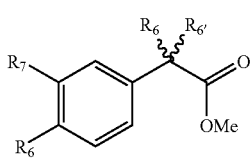

(IV)

wherein $R_6$, $R_{6'}$, $R_7$ and $R_8$ are defined as hereinabove, with a compound containing an acyl group having the formula $R_1CO$ so as to obtain a compound represented by formula (V)

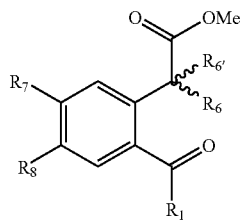

(V)

wherein $R_1$, $R_6$, $R_{6'}$, $R_7$ and $R_8$ are defined as hereinabove;

b) reacting a compound represented by formula (V) with hydrazine so as to obtain a compound represented by formula (VI) wherien $R_1$, $R_6$, $R_{6'}$, $R_7$ and $R_8$ are defined as hereinabove.

The acylating agent in step a) is preferably an acyl halogenide, particularly an acyl chloride. The reaction is advantageously carried out in the presence of a Lewis acid such as $SnCl_4$, in an inert solvent at room temperature. Solvents may be exemplified by hydrocarbons and their halogenated derivatives, for instance $CHCl_3$. When the reaction is complete, the resulting product is taken up in alcohol, methanol for example, and the reaction is continued at room temperature.

Step b) is advantageously carried out in the presence of hydrazine hydrate, for example in an alcohol, at a temperature comprised between 100 and 150° C., preferably at around 150° C., in a sealed tube for a time period ranging from 3 to 10 hours, preferably approximately 3 hours, and continued in the presence of an acid, for example acetic acid under ethanol reflux for 20 to 60 minutes.

The compounds represented by general formula (III) according to the invention may also be obtained directly from a compound represented by general formula (V) such as defined hereinabove, by reaction in the presence of a substituted hydrazine, for example methylhydrazine. Such reaction is advantageously carried out in an alcohol, ethanol for example, at a temperature comprised between 100 and 150° C., preferably at around 150° C., in a sealed tube for a time period ranging from 3 to 10 hours, preferably approximately 3 hours, and continued in the presence of an acid, for example acetic acid under ethanol reflux for 20 to 60 minutes.

In another embodiment, the compounds represented by general formula (III) according to the invention in which Z is an oxygen atom may be prepared from a compound represented by general formula (XIV)

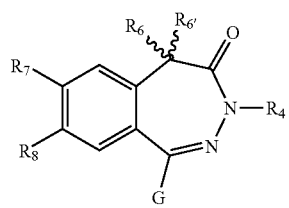

(XIV)

wherein $R_4$, $R_6$, $R_{6'}$, $R_7$ and $R_8$ are defined as hereinabove and G is an activator group such as a halogen (Cl or Br for example) or an O-triflate group, by a palladium coupling reaction in the presence of boronic, alcyn-1-yl acid or ester or organometallic acid or ester such as organozincics or organostannans. When G is a halogen atom, compound (III) may also be prepared by a substitution reaction in the presence of a nucleophilic agent, such as an amine for example, in ethanol.

The compounds represented by general formula (XIV) may be obtained by a method comprising:

reacting a compound represented by general formula (VII) as illustrated in FIG. 1 wherein $R_6$, $R_{6'}$, $R_7$ and $R_8$ are defined as hereinabove in the presence of paraformaldehyde, preferably by heating in acidic medium, to give a compound represented by general formula (VIII) such as illustrated in FIG. 1;

reacting a compound represented by general formula (VIII) in the presence of $KMnO_4$, followed by heating in an alcohol, to give a compound represented by general formula (IX) such as illustrated in FIG. 1 wherein $R_6$, $R_{6'}$, $R_7$ and $R_8$ are defined as hereinabove;

heating under reflux the compound represented by general formula (IX) in acetyl chloride to give a compound represented by general formula (X) such as illustrated in FIG. 1 wherein $R_6$, $R_{6'}$, $R_7$ and $R_8$ are defined as hereinabove;

reacting a compound represented by general formula (X) in the presence of hydrazine hydrate, preferably in ethanol, to give a compound represented by general formula (XI) such as illustrated in FIG. 1 wherein $R_6$, $R_{6'}$, $R_7$ and $R_8$ are defined as hereinabove;

reacting a compound represented by general formula (XI) in the presence of AcOH at a temperature comprised between 50 and 150° C. to give a compound represented by general formula (XII) such as illustrated in FIG. 1 wherein $R_6$, $R_{6'}$, $R_7$ and $R_8$ are defined as hereinabove;

reacting a compound represented by general formula (XII) in the presence of potassium carbonate and methyl iodide, preferably at room temperature in a solvent of the DMF type, to give a compound represented by general formula (XIII) such as illustrated in FIG. 1 wherein $R_4$, $R_6$, $R_{6'}$, $R_7$ and $R_8$ are defined as hereinabove; and reacting a compound represented by general formula (XIII) in the presence of dimethylaniline and phosphorus oxyhalogenide (for example $POCl_3$ or $POBr_3$), at a temperature comprised between 80 and 150° C., preferably in anhydrous $CHCl_3$ medium, to give a compound represented by general formula (XIV) such as illustrated in FIG. 1 wherein $R_4$, $R_6$, $R_{6'}$, $R_7$, $R_8$ and G are defined as hereinabove; or reacting a compound represented by general formula (XIII) with triflic anhydride in the presence of a base, for example n-BuLi in an anhydrous aprotic organic solvent, to give a compound represented by general formula (XIV) such as illustrated in FIG. 1 wherein $R_4$, $R_6$, $R_{6'}$, $R_7$ and $R_8$ are defined as hereinabove and G is a triflate group.

The compounds represented by formula (III) in which Z is a sulfur atom are obtained from compounds having formula (III) in which Z is an oxygen atom by reaction with Lawesson reagent in toluene under reflux.

The compounds represented by general formula (II) according to the invention in which Z is an oxygen atom may be prepared from a compound represented by general formula (XVIII):

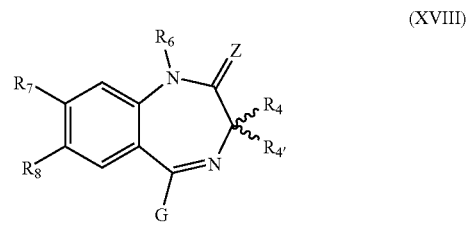

Figure 2:
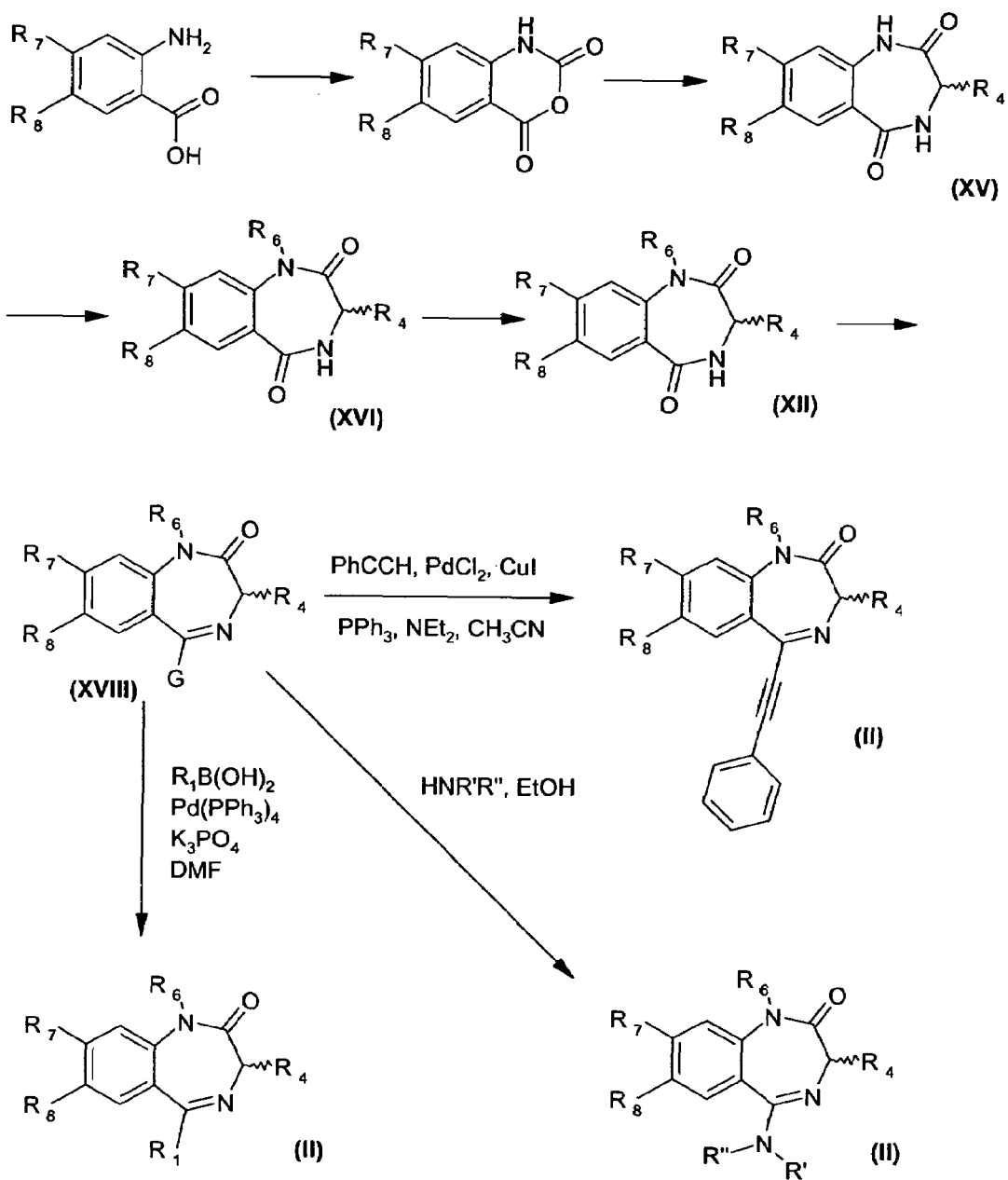

(XVIII)

wherein $R_4$, $R_{4'}$, $R_6$, $R_7$, $R_8$ and G are defined as hereinabove, by reacting with an acid compound of group $R_1$ in the presence of a palladium catalyst, such as illustrated in FIG. 2. The reaction is advantageously carried out in a solvent of the type DMF at a temperature comprised between 80 and 150° C.

The compounds represented by general formula (XVIII) may be obtained by a method such as illustrated in FIG. 2 and comprising:

reacting a compound represented by general formula (XV) wherein $R_7$ and $R_8$ are defined as hereinabove:

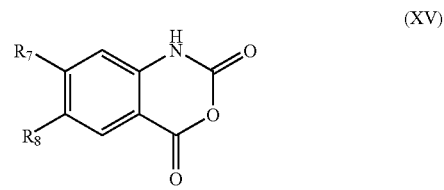

(XV)

in the presence of an alkyl halogenide, preferably in a solvent of the DMF type in the presence of NaH, to form a compound represented by general formula (XVI) wherein $R_7$ and $R_8$ are defined as hereinabove,

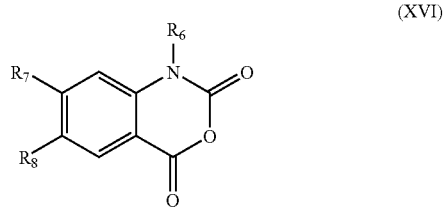

(XVI)

heating under reflux the compound represented by general formula (XVI) in the presence of α-amino acid ester hydrochloride and pyridine, followed by cycle formation in acidic medium, for example in the presence of acetic acid, at a temperature comprised between 100 and 150° C., to form a compound represented by general formula (XVII) wherein $R_4$, $R_{4'}$, $R_6$, $R_7$ and $R_8$ are defined as hereinabove,

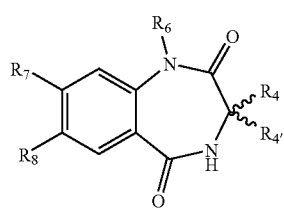

(XVII)

reacting the compound represented by general formula (XVII) in the presence of dimethylaniline (or dimethylaminopyridine) and phosphorus oxyhalogenide (preferably $POCl_3$ or $POBr_3$), preferably at a temperature comprised between 80 and 150° C. in anhydrous $CHCl_3$ medium and in a sealed tube, to form a compound represented by general formula (XVIII) wherein $R_4$, $R_{4'}$, $R_6$, $R_7$ and $R_8$ are defined as hereinabove and G is Cl or Br.

The compounds represented by formula (II) in which Z is a sulfur atom may be obtained from compounds represented by formula (II) in which Z is an oxygen atom by reaction with Lawesson reagent in toluene under reflux.

The compounds represented by general formula (II) according to the invention in which Z is an oxygen atom may also be prepared from a compound represented by general formula (XXII):

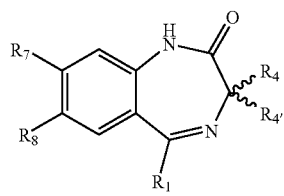

(XXII)

wherein $R_1$, $R_{4'}$, $R_7$, $R_8$, are defined as hereinabove, by reaction with an alkyl halogenide, preferably in a solvent of the type DMF or THF in the presence of a base, of the type NaH or $K_2CO_3$, preferably at room temperature (18–25° C.).

The compounds represented by general formula (XXII) may be obtained by a method comprising:
reacting a compound represented by general formula (XIX) in which $R_7$ and $R_8$ are defined as hereinabove:

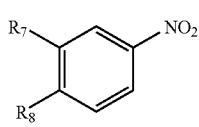

(XIX)

in the presence of hydrogen and a palladium catalyst in methanol to form a compound represented by general formula (XX) wherein $R_7$ and $R_8$ are defined as hereinabove,

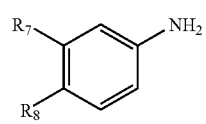

(XX)

heating under reflux the compound represented by general formula (XX) in the presence of Lewis acids, of the type $BCl_3$, $AlCl_3$, and a nitrile having general formula $R_1$—CN, in a halogenated solvent ($C_2H_4Cl_2$, $CHCl_3$), to form a compound represented by general formula (XXI) wherein $R_1$, $R_7$, $R_8$, are defined as hereinabove,

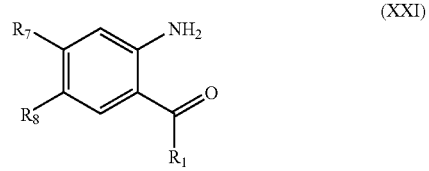

(XXI)

heating under reflux the compound represented by general formula (XXI), in the presence of a amino-acid ester hydrochloride substituted or not on the a carbon and which may be a racemic mixture or a pure enantiomer, and pyridine at a temperature comprised between 100 and 150° C. to form a compound represented by general formula (XXII) wherein $R_1$, $R_{4'}$, $R_7$, $R_8$ are defined as hereinabove (the molecules XXI and XXII were obtained by the method described in the reference: Yves Pascal, Charles R. Andrianjara, Eric Auclair, Nadine Avenel, Bernadette Bertin, Alain Calvet, Frederic Feru, Sophie Lardon, Indres Moodley, Malika Ouagued, Adrian Payne, Marie Pierre Pruniaux, and Corinne Szilagyi, *Bioorganic and Medicinal Chemistry Letters*, 2000, 10 35–38).

The invention is illustrated by the following examples, which are given for purposes of illustration and not by way of limitation. FIGS. 1 and 2 depict the synthetic routes of the inventive compounds.

EXAMPLE 1

Synthesis of Compounds Represented by Formula III According to the Invention by a First Route 1.1. Synthesis of intermediates represented by formula V
The following compounds were synthesized:
4,5-dimethoxy-2-(1-naphthoyl)phenyl methyl acetate, Vaa.
2-(2-benzo[b]thienylcarbonyl)-4,5-dimethoxyphenyl methyl acetate, Vab.
2-benzoyl-4,5-dimethoxyphenyl methyl acetate, Vac.
2-(4-iodobenzoyl)-4,5-dimethoxyphenyl methyl acetate, Vad.
2-(4-bromobenzoyl)-4,5-dimethoxyphenyl methyl aceetate, Vae.
2-(2-benzo[b]thienylcarbonyl)-4,5-diethoxyphenyl ethyl acetate, Vaf.
2-[2-(2-benzo[b]thienylcarbonyl)-4,5-diethoxyphenyl]ethyl valerate, Vag.
2-[2-(2-benzo[b]thienyl)carbonyl]-4,5-diethoxyphenyl] ethyl butyrate, Vah.

2-[2-(2-benzo[b]thienylcarbonyl)-4,5-dimethoxyphenyl]-2,
2-dimethyl methyl acetate; Vai.

4,5-dimethoxy-2-(1-naphthoyl)phenyl methyl acetate, Vaa.

To a solution of 315 mg (1.5 mmol) of 3,4-dimethoxyphenyl methyl acetate in 5 ml of anhydrous CHCl$_3$, add at 0° C. and under an inert atmosphere 452 μl (3 mmol) of 1-naphthoyl chloride. Add dropwise 351 μl of SnCl$_4$. Allow to return to room temperature. After 6 hours at room temperature, evaporate to dryness. Add 10 ml of MeOH. Stir at room temperature for 30 minutes. Evaporate to dryness. Add 7 ml of iced H$_2$O. Allow to crystallize at 0° C. for 1 hour. Filter. Wash twice with 1 ml of H$_2$O. Yield: 37%. The product is used as is for the subsequent reactions.

2-(2-benzo[b]thienylcarbonyl)-4,5-dimethoxyphenyl methyl acetate, Vab.

By replacing 1-naphthoyl chloride in example Vaa by 2-benzo[b]thiophene carbonyl chloride and proceeding in the same manner, the above named product is obtained. Yield: 58%. $^1$H-NMR (200 MHz, CDCl$_3$): d 3.63 (s, 3H, OCH$_3$), 3.88 (s, 2H, CH$_2$), 3.91 (s, 3H, OCH$_3$), 4.02 (s, 3H, OCH$_3$), 6.92 (s, 1H Ar), 7.26 (s, 1H Ar), 7.41–7.54 (m, 2H Ar), 7.81 (s, 1H Ar), 7.88–7.98 (m, 2H Ar).

2-benzoyl-4,5-dimethoxyphenyl methyl acetate, Vac.

By replacing 1-naphthoyl chloride in example Vaa by benzoyl chloride and proceeding in the same manner, the abovenamed product is obtained. Yield: 85%.

2-(4-iodobenzoyl)4,5-dimethoxyphenyl methyl aceetate, Vad.

By replacing 1-naphthoyl chloride in example Vaa by 4-iodobenzoyl chloride and proceeding in the same manner, the abovenamed product is obtained. Yield: 67%.

2-(4-bromobenzoyl)4,5-dimethoxyphenyl methyl acetate, Vae.

By replacing 1-naphthoyl chloride in example Vaa by 4-bromobenzoyl chloride and proceeding in the same manner, the abovenamed product is obtained. Yield: 10%. $^1$H-NMR (300 MHz, CDCl$_3$): δ 3.62 (s, 3H, CH$_3$), 3.80 (s, 3H, CH$_3$), 3.85 (s, 2H, CH$_2$), 3.97 (s, 3H, CH$_3$), 6.85 (s, 1H Ar), 6.90 (s, 1H Ar), 7.60–7.69 (m, 4H Ar).

2-(2-benzo[b]thienylcarbonyl)-4,5-diethoxyphenyl ethyl acetate, Vaf.

By replacing 3,4-dimethoxyphenyl methyl acetate in example Vab by 3,4-diethoxyphenyl ethyl acetate and proceeding in the same manner, the abovenamed product is obtained. Yield: 71%. $^1$H-NMR (200 MHz, CDCl$_3$): d 1.12 (t, J=7,1, 3H, CH$_3$), 1.41–1.55 (m, 6H, 2×CH$_3$), 3.60 (s, 2H, CH$_2$CO), 4.00–4.26 (m, 6H, 3×CH$_2$), 6.89 (s, 1H Ar), 7.24 (s, 1H Ar), 7.41–7.53 (m, 2H Ar), 7.77 (s, 1H Ar), 7.85–7.94 (m, 2H Ar).

2-[2-(2-benzo[b]thienylcarbonyl)-4,5-diethoxyphenyl]ethyl valerate, Vag.

By replacing 3,4-dimethoxyphenyl methyl acetate in example Vab by 2-(3,4-diethoxyphenyl) ethyl valerate and proceeding in the same manner, the abovenamed product is obtained. Yield: 61%.

2-[2-(2-benzo[b]thienyl)carbonyl]-4,5-diethoxyphenyl] ethyl butyrate, Vah.

By replacing 3,4-dimethoxyphenyl methyl acetate in example Vab by 2-(3,4-diethoxyphenyl)ethyl butyrate and proceeding in the same manner, the abovenamed product is obtained. Yield: 46%.

2-[2-(2-benzo[b]thienylcarbonyl)-4,5-dimethoxyphenyl]-2, 2-dimethyl methyl acetate, Vai.

By replacing 3,4-dimethoxyphenyl methyl acetate in example Vab by 2-(3,4-dimethoxyphenyl)-2,2-dimethyl methyl acetate and proceeding in the same manner, the abovenamed product is obtained. Yield: 43%.

1.2. Synthesis of Compounds Represented by Formula VI

The following compounds were synthesized:
7,8-dimethoxy-1-phenyl-3,5-dihydro-4H-2,3-benzodiazepin-4-one, VIaa.
1-(2-benzo[b]thienyl)-7,8-diethoxy-3,5-dihydro-4H-2,3-benzodiazepin-4-one, VIab.
1-(2-benzo[b]thienyl)-7,8-diethoxy-5-n-propyl-3,5-dihydro-4H-2,3-benzodiazepin-4-one, VIac.
1-(benzo[b]thienyl)-7,8-diethoxy-5-ethyl-3,5-dihydro-4H-2,3-benzodiazepin-4-one, VIad.
1-(2-benzo[b]thienyl)-7,8-dimethoxy-5,5-dimethyl-3,5-dihydro-4H-2,3-benzodiazepin-4-one, VIae.

7,8-dimethoxy-1-phenyl-3,5-dihydro-4H-2,3-benzodiazepin-4-one, VIaa.

Heat 500 mg (1.59 mmol) of 2-benzoyl-4,5-dimethoxyphenyl methyl acetate Vac, 2 ml of hydrazine hydrate and 12 ml of EtOH in a sealed tube at 150° C. for 3 hours. Cool to room temperature. Add 10 ml of AcOH. Heat under reflux for 25 minutes. Evaporate to dryness. Add 60 ml of iced H$_2$O. Allow to crystallize at 0° C. for 5 minutes. Filter and wash twice with 5 ml of H$_2$O, twice with 3 ml of EtOH and twice with 5 ml of pentane.

Recrystallize in EtOH/Et$_2$O. Yield: 82%. $^1$H-NMR (300 MHz, CDCl$_3$): d 3.51 (s, 2H, CH$_2$), 3.72 (s, 3H, OCH$_3$), 3.97 (s, 3H, OCH$_3$), 6.67 (s, 1H Ar), 6.86 (s, 1H Ar), 7.43–7.48 (m, 3H Ar), 7.62–7.65 (m, 2H Ar), 8.66 (broad s, 1H exchangeable, NH).

1-(2-benzo[b]thienyl)-7,8-diethoxy-3,5-dihydro-4H-2,3-benzodiazepin-4-one, VIab.

By replacing 2-benzoyl-4,5-dimethoxyphenyl methyl acetate Vac in example VIaa by 2-(2-benzo[b]thienylcarbonyl)-4,5-diethoxyphenyl ethyl acetate Vaf and proceeding in the same manner, the abovenamed product is obtained. Yield: 47%. $^1$H-NMR (200 MHz, CDCl$_3$): d 1.46 (t, J=7.1, 3H, CH$_3$), 1.56 (t, J=7.1, 3H, CH$_3$), 3.53 (s, 2H, CH$_2$CO), 4.07 (q, J=6.92, 2H, CH$_2$), 4.23 (q, J=6.92, 2H, CH$_2$), 6.89 (s, 11H Ar), 7.17 (s, 1H Ar), 7.39–7.48 (m, 3H Ar), 7.75–7.92 (m, 2H Ar), 8.40 (s, 1 exchangeable, NH).

1-(2-benzo[b]thienyl)-7,8-diethoxy-5-n-propyl-3,5-dihydro-4H-2,3-benzodiazepin-4-one, VIac.

By replacing 2-benzoyl-4,5-dimethoxyphenyl methyl acetate Vac in example VIaa by 2-[2-(2-benzo[b]thienylcarbonyl)-4,5-diethoxyphenyl]ethyl valerate Vag and proceeding in the same manner, the abovenamed product is obtained. 0.84–1.58 (m, 11H, 3×CH$_3$ and CH$_2$), 1.84–2.40 (m, 2H, CHCH$_2$), 3.09–3.16 (m, 1H, CH), 4.03–4.25 (m, 4H, 2×CH$_2$), 6.77–6.84 (m, 1H Ar), 7.14 (s, 1H Ar), 7.34–7.46 (m, 3H Ar), 7.72–7.90 (m, 2H Ar), 8.46–8.54 (m, 1H exchangeable, NH).

1-(benzo[b]thienyl)-7,8-diethoxy-5-ethyl-3,5-dihydro-4H-2,3-benzodiazepin-4-one, VIad.

By replacing 2-benzoyl-4,5-dimethoxyphenyl methyl acetate Vac in example VIaa by 2-[2-(2-benzo[b]thienyl) carbonyl]-4,5-diethoxyphenyl]ethyl butyrate Vah and proceeding in the same manner, the abovenamed product is obtained. Yield: 23%. $^1$H-NMR (300 MHz, CDCl$_3$):δ 1.11 (t, J=6.21, 3H, CH$_3$), 1.40–1.46 (m, 3H, CH$_3$), 1.53 (t, J=7.92, 3H, CH$_3$), 1.96–2.43 (m, 2H, CH$_2$), 3.02–3.07 (t, J=6.01, 1H, 5-H), 4.04–4.24 (m, 4H, 2×CH$_2$), 6.83 (s, 1H Ar), 7.15 (s, 1H Ar), 7.35–7.90 (m, 5H Ar), 8.39 (s, 1H exchangeable, NH).

1-(2-benzo[b]thienyl)-7,8-dimethoxy-5,5-dimethyl-3,5-dihydro-4H-2,3-benzodiazepin-4-one, VIae.

By replacing 2-benzoyl-4,5-dimethoxyphenyl methyl acetate V/aa in example V/aa by 2-[2-(2-benzo[b]thienylcarbonyl)-4,5-dimethoxyphenyl]-2,2-dimethyl methyl acetate Vai and proceeding in the same manner, the abovenamed product is obtained. Yield: 7%. $^1$H-NMR (300 MHz, CDCl$_3$): δ 1.36 (s, 3H, 5-CH$_3$), 1.79 (s, 3H, 5-CH$_3$), 3.83 (s, 3H, OCH$_3$), 4.00 (s, 3H, OCH$_3$), 7.03 (s, 1H Ar), 7.17 (s, 1H Ar), 7.35–7.44 (m, 3H Ar), 7.73–7.89 (m, 2H Ar), 8.39 (s, 1H exchangeable, NH).

1.3. Synthesis of Compounds Represented by Formula III
The following compounds were synthesized:

7,8-dimethoxy-3-methyl-1-(1-naphthyl)-3,5-dihydro-4H-2,3-benzodiazepin-4-one, IIIaa.

1-(2-benzo[b]thienyl)-7,8-dimethoxy-3-methyl-3,5-dihydro-4H-2,3-benzodiazepin-4-one, IIIab.

3-benzyl-7,8-dimethoxy-1-phenyl-3,5-dihydro-4H-2,3-benzodiazepin-4-one, IIIac.

3-dodecyl-7,8-dimethoxy-1-phenyl-3,5-dihydro-4H-2,3-benzodiazepin-4-one, IIIad.

7,8-dimethoxy-3-(12-methoxy-12-oxododecyl)-1-phenyl-3,5-dihydro-4H-2,3-benzodiazepin-4-one, IIIae.

7,8-dimethoxy-1-phenyl-3-n-propyl-3,5-dihydro-4H-2,3-benzodiazepin-4-one, IIIaf.

3-ethyl-7,8-dimethoxy-1-phenyl-3,5-dihydro-4H-2,3-benzodiazepin-4-one, IIIag.

1-(4-iodophenyl)-7,8-dimethoxy-3-methyl-3,5-dihydro-4H-2,3-benzodiazepin-4-one, IIIah.

7,8-dimethoxy-1-[4-(2-methoxyphenyl)phenyl]-3-methyl-3,5-dihydro-4H-2,3-benzodiazepin-4-one, IIIai.

7,8-dimethoxy-1-[4-(3-methoxyphenyl)phenyl]-3-methyl-3,5-dihydro-4H-2,3-benzodiazepin-4-one, IIIaj.

1-[4-(3-acetylphenyl)phenyl]-7,8-dimethoxy-3-methyl-3,5-dihydro-4H-2,3-benzodiazepin-4-one, IIIak.

1-[4-(4-acetylphenyl)phenyl]-7,8-dimethoxy-3-methyl-3,5-dihydro-4H-2,3-benzodiazepin-4-one, IIIal.

1-[4-(3-acetamidophenyl)phenyl]-7,8-dimethoxy-3-methyl-3,5-dihydro-4H-2,3-benzodiazepin-4-one, IIIam.

1-(4-bromophenyl)-7,8-dimethoxy-3-methyl-3,5-dihydro-4H-2,3-benzodiazepin-4-one, IIIan.

7,8-dimethoxy-1-[4-(4-methoxyphenyl)phenyl]-3-methyl-3,5-dihydro-4H-2,3-benzodiazepin-4-one, IIIao.

1-[4-[3-(trifluoromethyl)phenyl]phenyl]-7,8-dimethoxy-3-methyl-3,5-dihydro-4H-2,3-benzodiazepin-4-one, IIIap.

7,8-dimethoxy-3-methyl-1-[4-(2-methylphenyl)phenyl]-3,5-dihydro-4H-2,3-benzodiazepin-4-one, IIIaq.

7,8-dimethoxy-3-methyl-1-[4-(3-methylphenyl)phenyl]-3,5-dihydro-4H-2,3-benzodiazepin-4-one, IIIar.

7,8-dimethoxy-3-methyl-1-[4-(4-methylphenyl)phenyl]-3,5-dihydro-4H-2,3-benzodiazepin-4-one, IIIas.

1-[4-(4-chlorophenyl)phenyl]-7,8-dimethoxy-3-methyl-3,5-dihydro-4H-2,3-benzodiazepin-4-one, IIIat.

7,8-dimethoxy-3-methyl-1-[4-(2-thienyl)phenyl]-3,5-dihydro-4H-2,3-benzodiazepin-4-one, IIIau.

1-[4-(2-furyl)phenyl]-7,8-dimethoxy-3-methyl-3,5-dihydro-4H-2,3-benzodiazepin-4-one, IIIav.

1-{4-[3,5-bis(trifluoromethyl)phenyl]phenyl}-7,8-dimethoxy-3-methyl-3,5-dihydro-4H-2,3-benzodiazepin-4-one, IIIaw.

1-[4-(heptyn-1-yl)phenyl]-7,8-dimethoxy-3-methyl-3,5-dihydro-4H-2,3-benzodiazepin-4-one, IIIax.

7,8-dimethoxy-3-methyl-1-[4-(3-nitrophenyl)phenyl]-3,5-dihydro-4H-2,3-benzodiazepin-4-one, IIIay.

1-(2-benzo[b]thienyl)-7,8-diethoxy-3-ethyl-3,5-dihydro-4H-2,3-benzodiazepin-4-one, IIIaz.

1-(2-benzo[b]thienyl)-7,8-diethoxy-3-methyl-3,5-dihydro-4H-2,3-benzodiazepin-4-one, IIIba.

1-(2-benzo[b]thienyl)-7,8-diethoxy-5-ethyl-3-methyl-3,5-dihydro-4H-2,3-benzodiazepin-4-one, IIIbb.

1-(2-benzo[b]thienyl)-7,8-diethoxy-3-methyl-5-n-propyl-3,5-dihydro-4H-2,3-benzodiazepin-4-one, IIIbc.

3,5-dibenzyl-7,8-dimethoxy-1-phenyl-3,5-dihydro-4H-2,3-benzodiazepin-4-one, IIIbd.

7,8-dimethoxy-1-phenyl-3-(3-hydroxypropyl)-3,5-dihydro-4H-2,3-benzodiazepin-4-one, IIbe.

7,8-dimethoxy-3-methyl-1'-(1'-naphthyl)-3,5-dihydro-4H-2,3-benzodiazepin-4-one, IIIaa.

Heat 150 mg (0.41 mmol) of 4,5-dimethoxy-2-(1-naphthoyl)phenyl methyl acetate Vaa, 200 μl of methylhydrazine and 12 ml of EtOH in a sealed tube at 150° C. for 3 hours.

Allow to cool to room temperature. Add 1 ml of AcOH. Heat under reflux for 25 minutes. Evaporate to dryness. Add 5 ml of iced H$_2$O. Allow to crystallize at 0° C. for 5 minutes. Filter and wash twice with 1 ml of H$_2$O, twice with 0.5 ml of EtOH and twice with 3 ml of pentane. Recrystalize in EtOH/Et$_2$O. Yield: 31%. $^1$H-NMR (200 MHz, CDCl$_3$): d 3.53 (s, 3H, CH$_3$), 3.57 (s, 3H, CH$_3$), 3.72 (s, 2H, CH$_2$), 4.00 (s, 3H, CH$_3$), 6.41 (s, 1H Ar), 6.95 (s, 1H Ar), 7.40–7.65 (m, 4H Ar), 7.78–7.82 (m, 1H Ar), 7.92–8.03 (m, 2H Ar).

1-(2-benzo[b]thienyl)-7,8-dimethoxy-3-methyl-3,5-dihydro-4H-2,3-benzodiazepin-4-one, IIIab.

By replacing 4,5-dimethoxy-2-(1-naphthoyl)phenyl methyl acetate Vaa in example IIIaa by 2-(2-benzo[b]thienylcarbonyl)-4,5-dimethoxyphenyl methyl acetate Vab and proceeding in the same manner, the abovenamed product is obtained. Yield: 69%. M: 112–115° C. $^1$H-NMR (200 MHz, CDCl$_3$): d 3.44 (s, 3H, CH$_3$), 3.52 (s, 2H, CH$_2$), 3.86 (s, 3H, CH$_3$), 3.99 (s, 3H, CH$_3$), 6.89 (s, 1H Ar), 7.13 (s, 1H Ar), 7.37–7.44 (m, 3H Ar), 7.74–7.89 (m, 2H Ar).

3-benzyl-7,8-dimethoxy-1-phenyl-3,5-dihydro-4H-2,3-benzodiazepin-4-one, IIIac.

To a solution of 7,8-dimethoxy-1-phenyl-3,5-dihydro-4H-2,3-benzodiazepin-4-one VIaa (100 mg, 0.34 mmol) in DMF (5 ml), under an inert atmosphere, add NaH in oil (12 mg, 0.30 mmol). Then add dropwise benzyl bromide (40 μl, 0.34 mmol). After 2 hours at room temperature, evaporate the DMF. Take up the residue in CH$_2$Cl$_2$, wash twice with water. Dry the organic phases on Na$_2$SO$_4$. Purify by silica gel column chromatography (AcOEt/hexane, 4:1). Yield: 71%. M: 114–116° C. $^1$H-NMR (200 MHz, CDCl$_3$): d 3.53–3.64 (m, 2H, CH$_2$), 3.73 (s, 3H, OCH$_3$), 4.00 (s, 3H, OCH$_3$), 4.93–5.32 (d, 2H, NCH$_2$Ph), 6.63 (s, 1H, Ar), 6.92 (s, 1H, Ar), 7.20–7.59 (m, 10H, Ar).

3-n-dodecyl-7,8-dimethoxy-1-phenyl-3,5-dihydro-4H-2,3-benzodiazepin-4-one, IIIad.

By replacing benzyl bromide in example IIIac by n-dodecyl bromide and proceeding in the same manner, the abovenamed product is obtained in the form of a colorless oil.

Yield: 46%. $^1$H-NMR (200 MHz, CDCl$_3$): d 0.88 (t, J=4.5, 3H, CH$_3$), 1.25 (m, 18H, 9×CH$_2$), 1.65 (m, 2H, NCH$_2$CH$_2$), 3.43 (m, 2H, NCH$_2$), 3.73 (s, 3H, OCH$_3$), 3.80 (broad s, 2H, CH$_2$), 3.97 (s, 3H, OCH$_3$), 6.67 (s, 1H, Ar), 6.88 (s, 1H, Ar), 7.44 (m, 3H, Ar), 7.66 (m, 2H, Ar).

7,8-dimethoxy-3-(12-methoxy-12-oxododecyl)-1-phenyl-3,5-dihydro-4H-2,3-benzodiazepin-4-one, IIIae.

By replacing benzyl bromide in example IIIac by methyl 12-bromododecanoate and proceeding in the same manner, the abovenamed product is obtained as a colorless oil.

Yield: 99%. $^1$H-NMR (300 MHz, CDCl$_3$): d 1.20 (m, 14H, 7×CH$_2$), 1.56–1.64 (m, 4H, 2×CH$_2$), 2.27 (t, J=7.1, CH$_2$COO), 3.47 (broad m, 2H, NCH$_2$), 3.64 (s, 3H, COOCH$_3$), 3.70 (s, 3H, OCH$_3$), 3.75 (broad s, 2H, CH$_2$), 3.94 (s, 3H, OCH$_3$), 6.65 (s, 1H, Ar), 6.86 (s, 1H, Ar), 7.42 (m, 3H, Ar), 7.64 (m, 2H, Ar).

7,8-dimethoxy-1-phenyl-3-n-propyl-3,5-dihydro-4H-2,3-benzodiazepin-4-one, IIIaf.

Add dropwise under an inert atmosphere 400 µl of iodopropane to a solution of 200 mg (0.675 mmol) of 7,8-dimethoxy-1-phenyl-3,5-dihydro-4H-2,3-benzodiazepin-4-one VIaa and 121 mg (0.878 mmol) of K$_2$CO$_3$ in solution in 5 ml of DMF. After 72 hours at room temperature, add 30 ml of H$_2$O and extract three times with 30 ml of Et$_2$O. Dry the organic fractions on Na$_2$SO$_4$. Purify by chromatography (AcOEt 1/hexane 1). Yield: 72%. M: 48–52° C. $^1$H-NMR (300 MHz, CDCl$_3$): d 0.83 (t, J=7.34, 3H, CH$_3$), 1.65–1.72 (m, 2H, CH$_2$CH$_3$), 2.85–3.62 (m, 4H, CH$_2$CH$_2$CH$_3$+5-CH$_2$), 3.74 (s, 3H, OCH$_3$), 3.98 (s, 3H, OCH$_3$), 6.67 (s, 1H Ar), 6.89 (s, 1H Ar), 7.43–7.47 (m, 3H Ar), 7.65–7.68 (m, 2H Ar).

3-ethyl-7,8-dimethoxy-1-phenyl-3,5-dihydro-4H-2,3-benzodiazepin-4-one, IIIag.

By replacing iodopropane in example IIIaf by iodoethane and proceeding in the same manner, the abovenamed product is obtained. Yield: 84%. M: 123–126° C. $^1$H-NMR (200 MHz, CDCl$_3$): d 1.29 (t, J=7.08, 3H, CH$_3$), 3.25–3.70 (m, 5H, 5-CH$_2$+OCH$_3$), 2.90–4.00 (m, 5H, CH$_2$CH$_3$+OCH$_3$), 6.71 (s, 1H Ar), 6.91 (s, 1H Ar), 7.46–7.51 (m, 3H Ar), 7.68–7.71 (m, 2H Ar).

1-(4-iodophenyl)-7,8-dimethoxy-3-methyl-3,5-dihydro-4H-2,3-benzodiazepin-4-one, IIIah.

By replacing 4,5-dimethoxy-2-(1-naphthoyl)phenyl methyl acetate Vaa in example IIIaa by 2-(4-iodobenzoyl)-4,5-dimethoxyphenyl methyl acetate Vad and proceeding in the same manner, the abovenamed product is obtained. Yield: 32%. M: 158–160° C. $^1$H-NMR (200 MHz, CDCl$_3$): d 3.40–3.48 (s, 5H, CH$_3$+CH$_2$), 3.75 (s, 3H, CH$_3$), 3.97 (s, 3H, CH$_3$), 6.64 (s, 1H Ar), 6.87 (s, 1H Ar), 7.59 (AB system, ? d=0.38, J$_{AB}$=8.80, 4H Ar).

7,8-dimethoxy-1-[4-(2-methoxyphenyl)phenyl]-3-methyl-3,5-dihydro-4H-2,3-benzodiazepin-4-one, IIIai.

Heat at 90° C. for 12 hours under an inert atmosphere a mixture of 100 mg (0.229 mmol) of 1-(4-iodophenyl)-7,8-dimethoxy-3-methyl-3,5-dihydro-4H-2,3-benzodiazepin-4-one IIIah, 38 mg (0.25 mmol) of 2-methoxybenzene boronic acid, 215 µl of 2M Na$_2$CO$_3$, 25 mg (0.020 mmol) of tetrakis(triphenylphosphine)Pd(0) and 250 µl of EtOH in 5 ml of degassed toluene. Allow to cool to room temperature. Add 80 ml of H$_2$O and extract three times with 50 ml of Et$_2$O. Dry the organic fractions on Na$_2$SO$_4$. Purify by chromatography (AcOEt). Recrystallize in Et$_2$O/pentane. The reaction yields 70 mg of the abovenamed product in the form of colorless crystals. Yield: 73%. M: 185–186° C. $^1$H-NMR (CDCl$_3$, 300 MHz): d 3.40–3.51 (m, 5H, CH$_2$+CH$_3$), 3.78 (s, 3H, CH$_3$), 3.85 (s, 3H, CH$_3$), 3.98 (s, 3H, CH$_3$), 6.80 (s, 1H Ar), 6.89 (s, 1H Ar), 7.04–7.73 (m, 8H Ar).

7,8-dimethoxy-1-[4-(3-methoxyphenyl)phenyl]-3-methyl-3,5-dihydro-4H-2,3-benzodiazepin-4-one, IIIaj.

By replacing 2-methoxybenzene boronic acid in example IIIai by 3-methoxybenzene boronic acid and proceeding in the same manner, the abovenamed product is obtained.

Yield: 68%. M: 92–99° C. $^1$H-NMR (CDCl$_3$, 300 MHz): d 3.41–3.50 (m, 5H, CH$_2$+CH$_3$), 3.76 (s, 3H, CH$_3$), 3.89 (s, 3H, CH$_3$), 4.12 (s, 3H, CH$_3$), 6.75 (s, 1H Ar), 6.89 (s, 1H Ar), 6.94–7.75 (m, 8H Ar).

1-[4-(3-acetylphenyl)phenyl]-7,8-dimethoxy-3-methyl-3,5-dihydro-4H-2,3-benzodiazepin-4-one, IIIak.

By replacing 2-methoxybenzene boronic acid in example IIIai by 3-acetylbenzene boronic acid and proceeding in the same manner, the abovenamed product is obtained.

Yield: 76%. M: 147–149° C. $^1$H-NMR (CDCl$_3$, 300 MHz): d 2.69 (s, 3H, CH$_3$CO), 3.43–3.53 (m, 5H, CH$_2$+CH$_3$), 3.77 (s, 3H, CH$_3$), 3.98 (s, 3H, CH$_3$), 6.73 (s, 1H Ar), 6.90 (s, 1H Ar), 7.59–8.27 (m, 8H Ar).

1-[4-(4-acetylphenyl)phenyl]-7,8-dimethoxy-3-methyl-3,5-dihydro-4H-2,3-benzodiazepin-4-one, IIIal.

By replacing 2-methoxybenzene boronic acid in example IIIai by 4-acetylbenzene boronic acid and proceeding in the same manner, the abovenamed product is obtained.

Yield: 68%. M: 199–201° C. $^1$H-NMR (CDCl$_3$, 300 MHz): d 2.67 (s, 3H, CH$_3$CO), 3.43–3.54 (m, 5H, CH$_2$+CH$_3$), 3.76 (s, 3H, CH$_3$), 3.98 (s, 3H, CH$_3$), 6.73 (s, 1H Ar), 6.90 (s, 1H Ar), 7.70–7.80 (m, 6H Ar), 8.06–8.09 (m, 2H Ar).

1-[4-(3-acetamidophenyl)phenyl]-7,8-dimethoxy-3-methyl-3,5-dihydro-4H-2,3-benzodiazepin-4-one, IIIam.

By replacing 2-methoxybenzene boronic acid in example IIIai by 4-acetamidobenzene boronic acid and proceeding in the same manner, the abovenamed product is obtained.

Yield: 61%. MF: 244–246° C. $^1$H-NMR (CDCl$_3$, 300 MHz): d 2.23 (s, 3H, CH$_3$CO), 3.43–3.53 (m, 5H, CH$_2$+CH$_3$), 3.76 (s, 3H, CH$_3$), 3.98 (s, 3H, CH$_3$), 6.73 (s, 1H Ar), 6.89 (s, 1H Ar), 7.40–7.74 (m, 8H Ar), 7.90 (broad s, 1H exchangeable, NH).

1-(4-bromophenyl)-7,8-dimethoxy-3-methyl-3,5-dihydro-4H-2,3-benzodiazepin-4-one, IIIan.

By replacing 2-(4-iodobenzoyl)-4,5-dimethoxyphenyl methyl acetate Vad in example IIIah by 2-(4-bromobenzoyl)-4,5-dimethoxyphenyl methyl acetate Vae and proceeding in the same manner, the abovenamed product is obtained. Yield: 37%. M: 145–147° C. $^1$H-NMR (300 MHz, CDCl$_3$): d 3.40–3.49 (s, 5H, CH$_3$+CH$_2$), 3.75 (s, 3H, CH$_3$), 3.97 (s, 3H, CH$_3$), 6.64 (s, 1H Ar), 6.87 (s, 1H Ar), 7.56 (AB system, ? d=0.16, J$_{AB}$=8.30, 4H Ar).

7,8-dimethoxy-1-[4-(4-methoxyphenyl)phenyl]-3-methyl-3,5-dihydro-4H-2,3-benzodiazepin-4-one, IIao.

By replacing 2-methoxybenzene boronic acid in example IIIai by 4-methoxybenzene boronic acid and proceeding in the same manner, the abovenamed product is obtained. Yield: 81%. M: 222–224° C. $^1$H-NMR (CDCl$_3$, 300 MHz): d 3.41–3.50 (m, 5H, CH$_2$+CH$_3$), 3.76 (s, 3H, CH$_3$), 3.88 (s, 3H, CH$_3$), 3.98 (s, 3H, CH$_3$), 6.75 (s, 1H Ar), 6.89 (s, 1H Ar), 7.37 (AB system, ? d=0.67, J$_{AB}$=8.7, 4H Ar), 7.59–7.65 (m, 4H Ar).

1-[4-[3-(trifluoromethyl)phenyl]phenyl]-7,8-dimethoxy-3-methyl-3,5-dihydro-4H-2,3-benzodiazepin-4-one, IIIap.

By replacing 2-methoxybenzene boronic acid in example IIIai by 3-trifluoromethylbenzene boronic acid and proceeding in the same manner, the abovenamed product is obtained. Yield: 72%. M: 100–103° C. $^1$H-NMR (CDCl$_3$, 300 MHz): d 3.43–3.53 (m, 5H, CH$_2$+CH$_3$), 3.76 (s, 3H, CH$_3$), 3.98 (s, 3H, CH$_3$), 6.73 (s, 1H Ar), 6.90 (s, 1H Ar), 7.52–7.89 (m, 8H Ar).

7,8-dimethoxy-3-methyl-1-[4-(2-methylphenyl)phenyl]-3,5-dihydro-4H-2,3-benzodiazepin-4-one, IIIaq.

By replacing 2-methoxybenzene boronic acid in example IIIai by 2-methylbenzene boronic acid and proceeding in the same manner, the abovenamed product is obtained.

Yield: 84%. M: 184–186° C. $^1$H-NMR (CDCl$_3$, 300 MHz): d 2.31 (s, 3H, PhCH$_3$), 3.40–3.51 (m, 5H, CH$_2$+CH$_3$), 3.78 (s, 3H, CH$_3$), 3.98 (s, 3H, CH$_3$), 6.78 (s, 1H Ar), 6.89 (s, 1H Ar), 7.28–7.73 (m, 8H Ar).

7,8-dimethoxy-3-methyl-1-[4-(3-methylphenyl)phenyl]-3,5-dihydro-4H-2,3-benzodiazepin-4-one, IIIar.

By replacing 2-methoxybenzene boronic acid in example IIIai by 3-methylbenzene boronic acid and proceeding in the same manner, the abovenamed product is obtained.

Yield: 81%. M: 154–156° C. $^1$H-NMR (CDCl$_3$, 300 MHz): d 2.45 (s, 3H, PhCH$_3$), 3.40–3.51 (m, 5H, CH$_2$+CH$_3$), 3.76 (s, 3H, CH$_3$), 3.98 (s, 3H, CH$_3$), 6.75 (s, 1H Ar), 6.89 (s,1H Ar), 7.20–7.75 (m, 8H Ar).

7,8-dimethoxy-3-methyl-1-[4-(4-methylphenyl)phenyl]-3,5-dihydro-4H-2,3-benzodiazepin-4-one, IIIas.

By replacing 2-methoxybenzene boronic acid in example IIIai by 4-methylbenzene boronic acid and proceeding in the same manner, the abovenamed product is obtained.

Yield: 84%. M: 191–192° C. $^1$H-NMR (CDCl$_3$, 300 MHz): d 2.42 (s, 3H, PhCH$_3$), 3.40–3.51 (m, 5H, CH$_2$+CH$_3$), 3.76 (s, 3H, CH$_3$), 3.98 (s, 3H, CH$_3$), 6.75 (s, 1H Ar), 6.89 (s, 1H Ar), 7.28–7.74 (m, 8H Ar).

1-[4-(4-chlorophenyl)phenyl]-7,8-dimethoxy-3-methyl-3,5-dihydro-4H-2,3-benzodiazepin-4-one, IIIat.

By replacing 2-methoxybenzene boronic acid in example IIIai by 4-chlorobenzene boronic acid and proceeding in the same manner, the abovenamed product is obtained.

Yield: 44%. M: 191–193° C. $^1$H-NMR (CDCl$_3$, 200 MHz): δ 3.41–3.52 (m, 5H, CH$_2$+CH$_3$), 3.75 (s, 3H, OCH$_3$), 3.98 (s, 3H, OCH$_3$), 6.73 (s, 1H Ar), 6.89 (s, 1H Ar), 7.24–7.72 (m, 8H Ar).

7,8-dimethoxy-3-methyl-1-[4-(2-thienyl)phenyl]-3,5-dihydro-4H-2,3-benzodiazepin-4-one, IIIau.

By replacing 2-methoxybenzene boronic acid in example IIIai by 2-thiophene boronic acid and proceeding in the same manner, the abovenamed product is obtained. Yield 41%. M: 147–149° C.

1-[4-(2-furyl)phenyl]-7,8-dimethoxy-3-methyl-3,5-dihydro-4H-2,3-benzodiazepin-4-one, IIIav.

By replacing 2-methoxybenzene boronic acid in example IIIai by 2-furanboronic acid and proceeding in the same manner, the abovenamed product is obtained. Yield: 89%.

M: 178–179° C. $^1$H-NMR (CDCl$_3$, 300 MHz): d 3.40–3.51 (m, 5H, CH$_2$+CH$_3$), 3.74 (s, 3H, CH$_3$), 3.97 (s, 3H, CH$_3$), 6.51–6.53 (m, 1H Ar), 6.70 (s, 1H Ar), 6.76–6.78 (m, 1H Ar), 6.88 (s, 1H Ar), 7.52–7.75 (m, 5H Ar).

1-{4-[3,5-bis-(trifluoromethyl)phenyl]phenyl}-7,8-dimethoxy-3-methyl-3,5-dihydro-4H-2,3-benzodiazepin-4-one, IIIaw.

By replacing 2-methoxybenzene boronic acid in example IIIai by 3,5-bis(trifluoromethyl)benzene boronic acid and proceeding in the same manner, the abovenamed product is obtained. Yield: 32%. M: 192–194° C. $^1$H-NMR (300 MHz, CDCl$_3$): δ 3.40–3.51 (m, 5H, CH$_2$+CH$_3$), 3.76 (s, 3H, OCH$_3$), 3.98 (s, 3H, OCH$_3$), 6.70 (s, 1H Ar), 6.90 (s, 1H Ar), 7.67–8.06 (m, 7H Ar).

1-[4-(heptyn-1-yl)phenyl]-7,8-dimethoxy-3-methyl-3,5-dihydro-4H-2,3-benzodiazepin-4-one, IIIax.

Stir for 3 hours at room temperature under an inert atmosphere a mixture of 1-(4-iodophenyl)-7,8-dimethoxy-3-methyl-3,5-dihydro-4H-2,3-benzodiazepin-4-one IIIah, 12 mg of CuI, 7 mg of PdCl$_2$, 23 mg of PPh$_3$, 2 ml of TEA, 4 ml of heptyne, in 12 ml of CH$_3$CN. Evaporate to dryness and purify by silica chromatography (AcOEt 1/hexane 1).

Recrystallize in EtOH/pentane. Yield: 16%. M: 110–112° C. $^1$H-NMR (300 MHz, CDCl$_3$): δ 0.94 (t, J=7.2, 3H, CH$_3$), 1.36–1.64 (m, 8H, 4×CH$_2$), 2.44 (t, J=7.2, 2H, C≡CCH$_2$), 3.43 (s, 3H, NCH$_3$), 3.72 (s, 3H, OCH$_3$), 3.96 (s, 3H, OCH$_3$), 6.64 (s, 1H Ar), 6.86 (s, 1H Ar), 7.43–7.60 (m, 4H Ar).

7,8-dimethoxy-3-methyl-1-[4-(3-nitrophenyl)phenyl]-3,5-dihydro-4H-2,3-benzodiazepin-4-one, IIIay.

By replacing 2-methoxybenzene boronic acid in example IIIai by 3-nitrophenyl boronic acid and proceeding in the same manner, the abovenamed product is obtained. Yield: 89%. M: 211–213° C. $^1$H-NMR (CDCl$_3$, 200 MHz): d 3.50–3.56 (m, 5H, CH$_2$+CH$_3$), 3.80 (s, 3H, CH$_3$), 4.02 (s, 3H, CH$_3$), 6.75 (s, 1H Ar), 6.93 (s, 1H Ar), 7.65–8.56 (m, 8H Ar).

1-(2-benzo[b]thienyl)-7,8-diethoxy-3-ethyl-3,5-dihydro-4H-2,3-benzodiazepin-4-one, IIIaz.

By replacing 7,8-dimethoxy-1-phenyl-3,5-dihydro-4H-2,3-benzodiazepin-4-one VIaa in example IIIag by 1-(2-benzo[b]thienyl)-7,8-diethoxy-3,5-dihydro-4H-2,3-benzodiazepin-4-one VIab and proceeding in the same manner, the abovenamed product is obtained. Yield: 72%. M: 100–103° C. $^1$H-NMR (200 MHz, CDCl$_3$): d 1.26 (t, J=7.1, 3H, CH$_3$), 1.44 (t, J=7.0, 3H, CH$_3$), 1.52 (t, J=7.1, 3H, CH$_3$), 3.29–3.56 (m, 2H, 5-CH$_2$), 3.85–4.25 (m, 6H, 3×CH$_2$CH$_3$), 6.87 (s, 1H Ar), 7.15 (s, 1H Ar), 7.32–7.44 (m, 3H Ar), 7.71–7.89 (m, 2H Ar).

1-(2-benzo[b]thienyl)-7,8-diethoxy-3-methyl-3,5-dihydro-4H-2,3-benzodiazepin-4-one, IIIba.

By replacing ethyl iodide in example IIIaz by methyl iodide and proceeding in the same manner, the abovenamed product is obtained. Yield: 65%. M: 157–160° C. $^1$H-NMR (200 MHz, CDCl$_3$): d 1.43 (t, J=7.0, 3H, CH$_3$), 1.52 (t, J=7.2, 3H, CH$_3$), 3.38–3.58 (m, 5H, CH$_3$+5-CH$_2$), 4.05 (q, J=7.2, 2H, CH$_2$CH$_3$), 4.19 (q, J=7.0, 2H, CH$_2$CH$_3$), 6.87 (s, 1H Ar), 7.13 (s, 1H Ar), 7.35–7.44 (m, 3H Ar), 7.71–7.89 (m, 2H Ar).

1-(2-benzo[b]thienyl)-7,8-diethoxy-5-ethyl-3-methyl-3,5-dihydro-4H-2,3-benzodiazepin-4-one, IIIbb.

By replacing 1-(2-benzo[b]thienyl)-7,8-diethoxy-3,5-dihydro-4H-2,3-benzodiazepin-4-one VIab in example IIIba by 1-(benzo[b]thienyl)-7,8-diethoxy-5-ethyl-3,5-dihydro-4H-2,3-benzodiazepin-4-one VIad and proceeding in the same manner, the abovenamed product is obtained. Yield: 70%. M: 79–81° C. $^1$H-NMR (200 MHz, CDCl$_3$): d 1.07 (t, J=7.2, 3H, CH$_3$), 1.42 (t, J=7.0, 3H, CH$_3$), 1.52 (t, J=7.0, 3H, CH$_3$), 1.92–2.47 (m, 2H, 5-CH$_2$CH$_3$), 2.96–3.04 (m, 1H, 5-H), 3.45 (s, 3H, 3-CH$_3$), 3.99–4.25 (m, 4H, 3×OCH$_2$CH$_3$), 6.83 (s, 1H Ar), 7.13 (s, 1H Ar), 7.35–7.44 (m, 3H Ar), 7.72–7.90 (m, 2H Ar).

1-(2-benzo[b]thienyl)-7,8-diethoxy-3-methyl-5-n-propyl-3,5-dihydro-4H-2,3-benzodiazepin-4-one, IIIbc.

By replacing 1-(2-benzo[b]thienyl)-7,8-diethoxy-3,5-dihydro-4H-2,3-benzodiazepin-4-one VIab in example IIIba by 1-(2-benzo[b]thienyl)-7,8-diethoxy-5-n-propyl-3,5-dihydro-4H-2,3-benzodiazepin-4-one VIac and proceeding in the same manner, the abovenamed product is obtained. Yield: 34%. M: 61–63° C. $^1$H-NMR (200 MHz, CDCl$_3$): d 1.01 (t, J=7.34, 3H, (CH$_2$)$_2$CH$_3$), 1.39–4.55 (m, 8H, CH$_2$CH$_2$CH$_3$+ 2×OCH$_2$CH$_3$), 1.75–2.42 (m, 2H, CH$_2$CH$_2$CH$_3$), 3.04–3.11 (m, 1H, 5-H), 3.45 (s, 3H, 3-CH$_3$), 3.99–4.23 (m, 4H, 2×OCH$_2$CH$_3$), 6.83 (s, 1H Ar), 7.12 (s, 1H Ar), 7.35–7.44 (m, 3H Ar), 7.72–7.89 (m, 2H Ar).

3,5-dibenzyl-7,8-dimethoxy-1-phenyl-3,5-dihydro-4H-2,3-benzodiazepin-4-one, IIIbd.

To a solution of 7,8-dimethoxy-1-phenyl-3,5-dihydro-4H-2,3-benzodiazepin-4-one VIaa (200 mg, 0.67 mmol) in DMF (10 ml), under an inert atmosphee, add NaH in oil (50 mg, 1.25 mmol). Then add dropwise benzyl bromide (150 µl, 1.26 mmol). After 2 hours at room temperature, evaporate the DMF. Take up the residue in CH$_2$Cl$_2$, wash twice with water. Dry the organic phases on Na$_2$SO$_4$. Purify by silica gel column chromatography (AcOEt/hexane, 4:1). Yield: 79%. $^1$H-NMR (200 MHz, CDCl$_3$): d 3.35–3.56 (m, 2H, CH$_2$Ph), 3.70 (s, 3H, OCH$_3$), 3.80 (m, 1H, CH), 3.97 (s, 3H, OCH$_3$), 4.87 (d, J=10.2, 1H, NCHPh), 5.30 (d, J=10.2, 1H, NCHPh), 6.61 (s, 1H, Ar), 6.93 (s, 1H, Ar), 7.06–7.42 (m, 13H, Ar), 7.59 (d, J=4.8, 2H, Ar). SM: 477 (M+H), 500 (M+H+Na).

7,8-dimethoxy-1-phenyl-3-(3-hydroxypropyl)-3,5-dihydro-4H-2,3-benzodiazepin-4-one, IIIbe.

By replacing benzyl bromide in example IIIac by propan-1-ol bromide and proceeding in the same manner, the abovenamed product is obtained. Yield: 44%. $^1$H-NMR (200 MHz, CDCl$_3$): d 1.88 (broad m, 2H, CH$_2$), 3.21 (broad s, 1H, OH), 3.44 (broad m, 4H, NCH$_2$ and CH$_2$O), 3.72 (s, 3H, OCH$_3$), 3.97 (s, 3H, OCH$_3$), 4.06 (m, 2H, CH$_2$), 6.66 (s, 1H, Ar), 6.88 (s, 1H, Ar), 7.44 (m, 3H, Ar), 7.64 (m, 2H, Ar).

EXAMPLE 2

Synthesis of Compounds Represented by Formula III According to the Invention by a Second Route 2.1. Synthesis of 6,7-dimethoxyisochroman-3-one, VIII.

Heat at 120° C. for 1 hour a mixture of 19.6 g (100 mmol) of 3,4-dimethoxyphenyl acetic acid (VII), 7.4 g (246 mmol) of paraformaldehyde and 20 ml of concentrated HCl in 100 ml of AcOH. Evaporate to dryness. Add 100 ml of H$_2$O, and extract three times with 200 ml of CH$_2$Cl$_2$. Wash the organic phases with 50 ml of 0.5 N NaHCO$_3$ and dry on Na$_2$SO$_4$. Evaporate to dryness. Allow to crystallize for 2 hours in 50 ml of Et$_2$O.

Filter and wash twice with 10 ml of Et$_2$O and twice with 20 ml of pentane. Yield: 83%.

M: 106–108° C. $^1$H-NMR (300 MHz, CDCl$_3$): d 3.64 (s, 2H, CH$_2$), 3.89 (s, 3H, OCH$_3$), 3.90 (s, 3H, OCH$_3$), 5.26 (s, 2H, CH$_2$), 6.71 (s, 1H Ar), 6.75 (s, 1H Ar).

2.2. Synthesis of 4,5-dimethoxyhomophthalic acid, IX.

Add dropwise 800 ml of a 10% solution of KMnO$_4$ to a solution of 10.4 g (50 mmol) of 6,7-dimethoxy-3-isochromanone VIII in 55 ml of 10% KOH. Stir at room temperature for 10 hours. Add 20 ml of EtOH and heat at 70° C. for 20 minutes. Concentrate the reaction medium to two-thirds. Acidify to pH 2–3 (check with pH paper) using concentrated HCl. Allow to crystallize at 0° C. for 1 hour. Filter and wash twice with 10 ml of H$_2$O. Yield: 78%. $^1$H-NMR (300 MHz, CDCl$_3$): d 3.93 (s, 2H, CH$_3$), 3.96 (s, 3H, OCH$_3$), 4.01 (s, 2H, CH$_2$), 6.74 (s, 1H Ar), 7.66 (s, 1H Ar).

2.3. Synthesis of 6,7-dimethoxyisochroman-1,3-diones, X.

Heat under reflux 3.6 g (15 mmol) of 4,5-dimethoxyhomophthalic acid IX, in 30 ml of acetyl chloride. Add 40 ml of Et$_2$O. Filter and wash twice with 3 ml of Et$_2$O then twice with 10 ml of pentane. Yield: 82%. The product is used as is for the subsequent reactions.

2.4. Synthesis of 2-(2-hydrazino-2-oxoethyl)4,5-dimethoxy benzoic acid, XI.

To a solution of 810 µl of hydrazine hydrate in 15 ml of EtOH, add 3 g (13.5 mmol) of 6,7-dimethoxyisochroman-1,3-diones X. Stir for 15 minutes at room temperature. Filter the precipitate. Wash twice with 5 ml of EtOH and twice with 10 ml of Et$_2$O. Yield: 96%. $^1$H-NMR (300 MHz, DMSO-D$_6$): d 3.69 (s, 2H, CH$_2$), 3.73 (s, 3H, OCH$_3$), 3.75 (s, 3H, OCH$_3$), 6.55 (broad s, 2H exchangeable, NH), 6.76 (s, 1H Ar), 7.34 (s, 1H Ar).

2.5. Synthesis of 7,8-dimethoxy-1,2,3,4-tetrahydro-5H-2,3-benzodiazepine-1,4-dione, XII.

To 15 ml of AcOH at 100° C., add 1.5 g (5.9 mmol) of 2-(2-hydrazino-2-oxoethyl)-4,5-dimethoxy benzoic acid XI. After 5 minutes at 100° C., cool in an ice bath. Filter and wash twice with 1 ml of AcOH, twice with 2 ml of H$_2$O, twice with 10 ml of Et$_2$O.

Yield: 78%. $^1$H-NMR (300 MHz, DMSO-D$_6$): d 3.76 (s, 3H, OCH$_3$), 3.78 (s, 3H, OCH$_3$), 3.88 (s, 2H, CH$_2$), 6.97 (s, 1H Ar), 7.40 (s, 1H Ar), 9.85 (s, 1H exchangeable, 2-NH), 12.4 (s, 1H exchangeable, 3-NH).

2.6. Synthesis of 7,8-dimethoxy-3-methyl-1,2,3,4-tetrahydro-5H-2,3-benzodiazepine-1,4-diones, XIII.

Stir at room temperature a mixture of 200 mg (0.85 mmol) of 7,8-dimethoxy-1,2,3,4-tetrahydro-5H-2,3-benzodiazepine-1,4-dione XII, 130 mg (0.93 mmol) of K$_2$CO$_3$ and 58 µl (0.93 mmol) of methyl iodide in 3 ml of anhydrous DMF. After 24 hours add 40 ml of H$_2$O. Filter the precipitate and wash once with 1 ml of H$_2$O, twice with 3 ml of MeOH and twice with 5 ml of Et$_2$O. Yield: 87%. $^1$H-NMR (300 MHz, DMSO-D$_6$): d 3.77 (s, 3H, OCH$_3$), 3.78 (s, 3H, OCH$_3$), 3.80 (s, 3H, OCH$_3$), 3.84 (s, 2H, CH$_2$), 7.00 (s, 1H Ar), 7.38 (s, 1H Ar), 9.87 (s, 1H exchangeable, NH).

2.7. Synthesis of 1-chloro-7,8-dimethoxy-3-methyl-3,5-dihydro-5H-2,3-benzodiazepin-4-one, XIVaa.

Heat at 115° C. in a sealed tube for 1 hour a solution of 100 mg (0.40 mmol) of 7,8-dimethoxy-3-methyl-1,2,3,4-tetrahydro-5H-2,3-benzodiazepine-1,4-diones XIII, 250 µl of dimethylaniline, 600 µl of POCl$_3$, in 10 ml of anhydrous CHCl$_3$. Allow to cool to room temperature. At −20° C. add 3 g of silica, 15 ml of CH$_2$Cl$_2$ and 3 ml of triethylamine. Evaporate to dryness. Purify by chromatography (AcOEt). Triturate in 1 ml of Et$_2$O. Filter and wash twice with 2 ml of pentane. Yield: 88%. $^1$H-NMR (CDCl$_3$, 200 MHz): d 3.68 (s, 3H, 3-CH$_3$), 3.79 (s, 3H, OCH$_3$), 3.80 (s, 3H, OCH$_3$), 4.47 (s, 2H, CH$_2$), 7.03 (s, 1H Ar), 7.44 (s, 11H Ar).

2.8. Synthesis of 1-bromo-7,8-dimethoxy-3-methyl-3,5-dihydro-5H-2,3-benzodiazepin-4-one, XIVab.

By replacing POCl$_3$ in example XIVaa by POBr$_3$ and proceeding in the same manner, the abovenamed product is obtained. Yield: 48%. $^1$H-NMR (CDCl$_3$, 200 MHz): d 3.84 (s, 3H, 3-CH$_3$), 3.91 (s, 3H, OCH$_3$), 3.96 (s, 3H, OCH$_3$), 4.61 (s, 2H, CH$_2$), 6.80 (s, 1H Ar), 7.58 (s, 11H Ar).

EXAMPLE 3

Synthesis of Compounds Represented by General Formula II According to the Invention by a First Route 3.1. Synthesis of intermediates represented by formula XVIII.

6,7-dimethoxy-1-methyl-1,2-dihydro-4H-3,1-benzoxazine-2,4-dione, XVI.

To a solution of 500 mg (3.06 mmol) of 6,7-dimethoxy-1,2-dihydro-4H-3,1-benzoxazine-2,4-dione (XV), in 6 ml of anhydrous DMF, add under an inert atmosphere 134 mg (3.37 mmol) of 60% NaH in oil. After 10 minutes at room temperature, add dropwise 219 μl (3.52 mmol) of MeI. Allow to stand at room temperature for 3 hours.

Add 40 ml of a water-ice mixture. Filter the precipitate and wash twice with 1 ml of EtOH and 3 ml of Et$_2$O. One obtains 320 mg of the abovenamed product in the form of a white powder. Yield: 59%. $^1$H-NMR (CDCl$_3$, 300 MHz): d 3.31 (s, 3H, 1-CH$_3$), 3.82 (s, 3H, OCH$_3$), 3.96 (s, 3H, OCH$_3$), 6.85 (s, 1H Ar), 7.32 (s, 1H Ar).

7,8-dimethoxy-1-methyl-3,4-dihydro-1H-1,4-benzodiazepine-2,5-dione, XVIIaa.

Heat under reflux for 6 hours a mixture of 320 mg (1.35 mmol) of 6,7-dimethoxy-1-methyl-1,2-dihydro-4H-3,1-benzoxazine-2,4-dione (XVI), 452 mg (3.24 mmol) of methyl glycinate hydrochloride in 4 ml of pyridine. Add 3 ml of AcOH and heat at 130° C. for 12 hours. Evaporate to dryness. Add 10 ml of a water-ice mixture. Allow to crystallize at 0° C. for 30 minutes. Filter and wash twice with 2 ml of H$_2$O, twice with 1 ml of EtOH and twice with 5 ml of Et$_2$O. Recrystallize in EtOH. One obtains 240 mg of the abovenamed product in the form of colorless crystals. Yield: 71%. M: 260–263° C. $^1$H-NMR (CDCl$_3$, 300 MHz): d 3.42 (s, 3H, NCH$_3$), 3.75–3.92 (m, 2H, CH$_2$), 3.98 (s, 6H, 2×OCH$_3$), 6.39 (s, 1H exchangeable, NH), 6.69 (s, 1H Ar), 7.37 (s, 1H Ar).

7,8-dimethoxy-3,4-dihydro-1H-1,4-benzodiazepine-2,5-dione, XVIIab.

By replacing 6,7-dimethoxy-1-methyl-11,2-dihydro-4H-3,1-benzoxazine-2,4-dione (XVI) in example XVIIaa by 6,7-dimethoxy-1,2-dihydro-4H-3,1-benzoxazine-2,4-dione (XV) and proceeding in the same manner, the abovenamed product is obtained. Yield: 54%. $^1$H-NMR (DMSO, 300 MHz): d 3.55 (d, J=5.3, 2H, CH$_2$), 3.77 (s, 6H, 2×OCH$_3$), 6.16 (s, 1H Ar), 6.67 (s, 1H Ar), 8.34 (t, J=5.3, 1H, NH), 10.07 (s, 1H, NH).

7,8-dimethoxy-1-n-propyl-3,4-dihydro-1H-1,4-benzodiazepine-2,5-dione, XVIIac.

To a solution of 723 mg (3.06 mmol) of 7,8-dimethoxy-3,4-dihydro-1H-1,4-benzodiazepine-2,5-dione (XVIIab), in 6 ml of anhydrous DMF, add under an inert atmosphere 134 mg (3.37 mmol) of 60% NaH in oil. After 10 minutes at room temperature, add dropwise 328 μl (3.37 mmol) of n-PrI. Allow to stand at room temperature for 3 hours. Add 40 ml of a water-ice mixture. Filter the precipitate and wash twice with 1 ml of EtOH and 3 ml of Et$_2$O. One obtains 320 mg of the abovenamed product in the form of a white powder. Yield: 65%. $^1$H-NMR (DMSO, 200 MHz): d 0.66–0.73 (m, 3H, CH$_2$CH$_3$), 1.27–1.39 (m, 2H, CH$_2$CH$_3$), 3.30–4.22 (m, 10H, CH$_2$+CH$_2$+2×OCH$_3$), 6.97 (s, 1H Ar), 7.13 (s, 1H Ar), 8.56 (s, 1H, NH).

1-benzyl-7,8-dimethoxy-3,4-dihydro-1H-1,4-benzodiazepine-2,5-dione, XVIIad.

By replacing n-Pr-I in example XVIIac by Bn-Br and proceeding in the same manner, the abovenamed product is obtained. Yield: 45%. $^1$H-NMR (DMSO, 200 MHz): d 3.53–3.77 (m, 8H, CH$_2$+2×OCH$_3$), 4.90–5.36 (m, 2H, CH$_2$), 6.98–7.29 (m, 7H Ar), 8.61 (t, J=5.6, 1H, NH).

7,8-dimethoxy-1,3-dimethyl-3,4-dihydro-1H-1,4-benzodiazepine-2,5-dione, XVIIae.

By replacing methyl glycinate hydrochloride in example XVIIaa by methyl alaninate hydrochloride and proceeding in the same manner, the abovenamed product is obtained.

Yield: 45%. $^1$H-NMR (CDCl$_3$, 200 MHz): d 1.47 (d, J=6.6, 3H, 3-CH$_3$), 3.40 (s, 3H, 1-CH$_3$), 3.92–3.97 (m, 7H, 3-CH+2×OCH$_3$), 6.13 (d, J=4.9, 1H exchangeable, NH), 6.66 (s, 1H Ar), 7.33 (s, 1H Ar).

5-chloro-7,8-dimethoxy-1-methyl-1,3-dihydro-1,4-benzodiazepin-2-one, XVIIIaa.

Heat at 125° C. in a sealed tube for 3Y4 hour a solution of 100 mg (0.40 mmol) of 7,8-dimethoxy-1-methyl-3,4-dihydro-1H-1,4-benzodiazepine-2,5-dione (XVIIaa), 280 μl of dimethylaniline, 800 μl of POCl$_3$, in 10 ml of anhydrous CHCl$_3$. Allow to cool to room temperature. Add 3 g of silica and 5 ml of CH$_2$Cl$_2$. Add at 0° C., 1 ml of triethylamine.

Evaporate to dryness. Purify by chromatography (AcOEt 1/hexane 1, then AcOEt).

Triturate in 1 ml of Et$_2$O. Filter and wash twice with 2 ml of pentane. One obtains 93 mg of the abovenamed product as a white powder. Yield: 87%. $^1$H-NMR (CDCl$_3$, 200 MHz): d 3.42 (s, 3H, NCH$_3$), 3.77 (broad s, 1H of CH$_2$), 3.99 (s, 3H, OCH$_3$), 4.00 (s, 3H, OCH$_3$), 4.65 (broad s, 1H of CH$_2$), 6.71 (s, 1H Ar), 7.22 (s, 1H Ar).

5-chloro-7,8-dimethoxy-1,3-dimethyl-1,3-dihydro-1,4-benzodiazepin-2-one, XVIIIab.

By replacing 7,8-dimethoxy-1-methyl-3,4-dihydro-1H-1,4-benzodiazepine-2,5-dione (XVIIaa) in example XVIIIaa by 7,8-dimethoxy-1,3-dimethyl-3,4-dihydro-1H-1,4-benzodiazepine-2,5-dione (XVIIae) and proceeding in the same manner, the abovenamed product is obtained. Yield: 78%. $^1$H-NMR (CDCl$_3$, 200 MHz): d 1.67 (d, J=6.6, 3H, 3-CH$_3$), 3.44 (s, 3H, 1-CH$_3$), 3.68 (q, J=6.6, 1H, 3-CH), 3.98 (s, 3H, OCH$_3$), 3.99 (s, 3H, OCH$_3$), 6.70 (s, 1H Ar), 7.21 (s, 1H Ar).

1-benzyl-5-chloro-7,8-dimethoxy-1,3-dihydro-1,4-benzodiazepin-2-one, XVIIIac.

By replacing 7,8-dimethoxy-1-methyl-3,4-dihydro-1H-1,4-benzodiazepine-2,5-dione (XVIIaa) in example XVIIIaa by 1-benzyl-7,8-dimethoxy-3,4-dihydro-1H-1,4-benzodiazepine-2,5-dione (XVIIad) and proceeding in the same manner, the abovenamed product is obtained. Yield: 53%. $^1$H-NMR (CDCl$_3$, 200 MHz): d 3.70–3.96 (m, 7H, CH+2×OCH$_3$), 4.65–4.78 (m, 1H CH), 5.09–5.12 (m, 2H, CH$_2$), 6.70 (s, 1H Ar), 7.15–7.39 (m, 6H Ar).

5-chloro-7,8-dimethoxy-1-n-propyl-1,3-dihydro-1,4-benzodiazepin-2-one, XVIIIad.

By replacing 7,8-dimethoxy-1-methyl-3,4-dihydro-1H-1,4-benzodiazepine-2,5-dione (XVIIaa) in example XVIIIaa by 7,8-dimethoxy-1-n-propyl-3,4-dihydro-1H-1,4-benzodiazepine-2,5-dione (XVIIac) and proceeding in the same manner, the abovenamed product is obtained. Yield: 34%. $^1$H-NMR (CDCl$_3$, 200 MHz): d 0.81–0.89 (m, 3H, CH$_2$CH$_3$), 1.46–1.61 (m, 2H, CH$_2$CH$_3$), 3.50–3.74 (m, 2H, 2×CH), 3.98 (s, 6H, 2×OCH$_3$), 4.22–4.66 (m, 2H, 2×CH), 6.77 (s, 1H Ar), 7.30 (s, 1H Ar).

3.2. Synthesis of compounds represented by formula (II)
The following compounds were synthesized:

7,8-dimethoxy-1-methyl-5-phenyl-1,3-dihydro-1,4-benzodiazepin-2-one, IIaa.

7,8-dimethoxy-5-(3,4-dimethoxyphenyl)-1-methyl-1,3-dihydro-1,4-benzodiazepin-2-one, IIIab.

5-(2-benzo[b]thienyl)-7,8-dimethoxy-1-methyl-1,3-dihydro-1,4-benzodiazepin-2-one, IIac.

7,8-dimethoxy-5-(4-fluorophenyl)-1-methyl-1,3-dihydro-2H-1,4-benzodiazepin-2-one, had.

7,8-dimethoxy-1-methyl-5-(4-pyridyl)-1,3-dihydro-2H-1,4-benzodiazepin-2-one, IIae.

7,8-dimethoxy-1-methyl-5-(3, 5 bistrifluoromethylphenyl)-1,3-dihydro-2H-1,4-benzodiazepin-2-one, Iaf.

5-(2-benzo[b]furyl)-7,8-dimethoxy-1-methyl-1,3-dihydro-1,4-benzodiazepin-2-one, IIag.

5-(2-furyl)-7,8-dimethoxy-1-methyl-1,3-dihydro-1,4-benzodiazepin-2-one, IIah.

5-(4-acetylphenyl)-7,8-dimethoxy-1-methyl-1,3-dihydro-1,4-benzodiazepin-2-one, IIai.

7,8-dimethoxy-5-(4-N,N-dimethylaminophenyl)-1-methyl-1,3-dihydro-2H-1,4-benzodiazepin-2-one, IIaj.

7,8-dimethoxy-1-methyl-5-(2-thienyl)-1,3-dihydro-1,4-benzodiazepin-2-one, IIak.

7,8-dimethoxy-5-(3-methoxyphenyl)-1-methyl-1,3-dihydro-1,4-benzodiazepin-2-one, IIal.

7,8-dimethoxy-5-(2-methoxyphenyl)-1-methyl-1,3-dihydro-1,4-benzodiazepin-2-one, IIam.

5-(5-indolyl)-7,8-dimethoxy-1-methyl-1,3-dihydro-1,4-benzodiazepin-2-one, Ian.

5-(6-benzyloxy-2-naphthyl)-7,8-dimethoxy-1-methyl-1,3-dihydro-1,4-benzodiazepin-2-one, IIao.

7,8-dimethoxy-5-(6-methoxy-2-naphthyl)-1-methyl-1,3-dihydro-1,4-benzodiazepin-2-one, IIap.

5-(2-indolyl)-7,8-dimethoxy-1-methyl-1,3-dihydro-1,4-benzodiazepin-2-one, IIaq.

7,8-dimethoxy-1-methyl-5-(piperidin-1-yl)-1,3-dihydro-1,4-benzodiazepin-2-one, IIar.

7,8-dimethoxy-1-methyl-5-[(E)-2-phenylethenyl]-1,3-dihydro-2H-1,4-benzodiazepin-2-one, IIas.

7,8-dimethoxy-5-(3-hydroxymethylphenyl)-1-methyl-3-propyl-1,3-dihydro-2H-1,4-benzodiazepin-2-one, IIat.

7,8-dimethoxy-1-methyl-5-(2-methylphenyl)-1,3-dihydro-1,4-benzodiazepin-2-one, IIau.

7,8-dimethoxy-1-methyl-5-(N-tetrahydro-1,2,3,4-isoquinolyl)-1,3-dihydro-2H-1,4-benzodiazepin-2-one, IIav.

7,8-dimethoxy-5-(4-methoxyphenyl)-1-methyl-1,3-dihydro-1,4-benzodiazepin-2-one, IIaw.

5-(3-bromophenyl)-7,8-dimethoxy-1-methyl-1,3-dihydro-2H-1,4-benzodiazepin-2-one, IIax.

5-(1,1'-biphenyl-3-yl)-7,8-dimethoxy-1-methyl-1,3-dihydro-2H-1,4-benzodiazepin-2-one, IIay.

7,8-dimethoxy-1-methyl-5-(2-phenylethyl)-1,3-dihydro-2H-1,4-benzodiazepin-2-one, IIaz.

7,8-dimethoxy-1-methyl-5-phenyl-1,3-dihydro-1,4-benzodiazepin-2-one, IIaa.

Heat at 115° C. for 12 hours under an inert atmosphere a mixture of 200 mg (0.74 mmol) of 5-chloro-7,8-dimethoxy-1-methyl-1,3-dihydro-1,4-benzodiazepin-2-one XVIIIaa, 109 mg (0.89 mmol) of benzene boronic acid, 182 mg (0.86 mmol) of $K_3PO_4$, 23 mg (0.020 mmol) of tetrakis(triphenylphosphine)Pd(0) in 5 ml of DMF. Allow to cool to room temperature. Add 80 ml of $H_2O$ and extract three times with 50 ml of $Et_2O$. Dry the organic fractions on $Na_2SO_4$. Purify by chromatography (AcOEt). Recrystallize in EtOH. One obtains 122 mg of the abovenamed product in the form of colorless crystals.

Yield: 53%. M: 109–112° C. $^1$H-NMR (CDCl$_3$, 200 MHz): d 3.40 (s, 3H, NCH$_3$), 3.75 (s, 3H, OCH$_3$), 3.98 (s, 3H, OCH$_3$), 4.30 (AB system, ? d=1.00, J$_{AB}$=10.2, 2H, CH$_2$), 6.71 (s, 1H Ar), 6.78 (s, 1H Ar), 7.35–7.47 (m, 3H Ar), 7.64–7.68 (m, 2H Ar).

7,8-dimethoxy-5-(3,4-dimethoxyphenyl)-1-methyl-1,3-dihydro-1,4-benzodiazepin-2-one, IIab.

By replacing benzene boronic acid in example IIaa by 3,4-dimethoxybenzene boronic acid and proceeding in the same manner, the abovenamed product is obtained. Yield: 82%. M: 130–133° C. $^1$H-NMR (CDCl$_3$, 200 MHz): d 3.40 (s, 3H, NCH$_3$), 3.43 (s, 3H, OCH$_3$), 3.94 (s, 6H, 2×OCH$_3$), 3.98 (s, 3H, OCH$_3$), 4.27 (AB system, ? d=0.98, J$_{AB}$=10.8, 2H, CH$_2$), 6.78–6.85 (m, 3H Ar), 7.04–7.09 (m, 1H Ar), 7.42–7.43 (m, 1H Ar).

5-(2-benzo[b]thienyl)-7,8-dimethoxy-1-methyl-1,3-dihydro-1,4-benzodiazepin-2-one, IIac.

By replacing benzene boronic acid in example IIaa by benzo[b]thiophene-2-boronic acid and proceeding in the same manner, the abovenamed product is obtained. Yield: 83%. M: 136–138° C. $^1$H-NMR (CDCl$_3$, 200 MHz): d 3.40 (s, 3H, NCH$_3$), 3.88 (s, 3H, OCH$_3$), 4.00 (s, 3H, OCH$_3$), 4.32 (AB system, ? d=0.93, J$_{AB}$=10.7, 2H, CH$_2$), 6.80 (s, 1H Ar), 7.15 (s, 1H Ar), 7.31–7.42 (m, 3H Ar), 7.69–7.89 (m, 2H Ar).

7,8-dimethoxy-5-(4-fluorophenyl)-1-methyl-1,3-dihydro-2H-1,4-benzodiazepin-2-one, IIad.

By replacing benzene boronic acid in example IIaa by 4-fluorobenzene boronic acid and proceeding in the same manner, the abovenamed product is obtained. Yield: 20%. M: 201–202° C. $^1$H-NMR (DMSO, 300 MHz): d 3.30 (s, 3H, NCH$_3$), 3.63 (s, 3H, OCH$_3$), 3.89 (s, 3H, OCH$_3$), 4.11 (AB system, ? d=0.79, J$_{AB}$=10.6, 2H, CH$_2$), 6.67 (s, 1H Ar), 7.08 (s, 1H Ar), 7.08–7.66 (m, 4H Ar).

7,8-dimethoxy-1-methyl-5-(4-pyridyl)-1,3-dihydro-2H-1,4-benzodiazepin-2-one, IIae.

By replacing benzene boronic acid in example IIaa by (pyrid-4-yl))-4,4,5,5-tetramethyl-1,3-dioxolaborolane acid and proceeding in the same manner, the abovenamed product is obtained. Yield: 25%. M: 170–172° C. $^1$H-NMR (DMSO, 200 MHz): d 3.34 (s, 3H, NCH$_3$), 3.68 (s, 3H, OCH$_3$), 3.93 (s, 3H, OCH$_3$), 4.25 (AB system, ? d=0.81, J$_{AB}$=10.5, 2H, CH$_2$), 6.73 (s, 1H Ar), 7.58 (d, 2H Ar, J=6.1), 8.72 (d, 2H Ar, J=5.9).

7,8-dimethoxy-1-methyl-5-(3, 5 bistrifluoromethylphenyl)-1,3-dihydro-2H-1,4-benzodiazepin-2-one, IIaf.

By replacing benzene boronic acid in example IIaa by 3, 5 bis trifluoromethylbenzene boronic acid and proceeding in the same manner, the abovenamed product is obtained. Yield: 20%. M: 180–182° C. $^1$H-NMR (CDCl$_3$, 300 MHz): d 3.44 (s, 3H, NCH$_3$), 3.76–3.88 (m, 4H, 1HCH$_2$+OCH$_3$), 4.02 (s, 3H, OCH$_3$), 4.89 (m, 1HCH$_2$), 6.61 (s, 1H Ar), 6.84 (s, 1H Ar), 7.98 (s, 1H Ar), 8.19 (s, 2H Ar).

5-(2-benzo[b]furyl)-7,8-dimethoxy-1-methyl-1,3-dihydro-1,4-benzodiazepin-2-one, IIag.

By replacing benzene boronic acid in example IIaa by 2-benzo[b]furanboronic acid and proceeding in the same manner, the abovenamed product is obtained. Yield: 70%. M: 139–141° C. $^1$H-NMR (CDCl$_3$, 300 MHz): d 3.40 (s, 3H, NCH$_3$), 3.89 (s, 3H, OCH$_3$), 4.00 (s, 3H, OCH$_3$), 4.41 (AB system, ? d=1.03, $J_{AB}$=10.3, 2H, CH$_2$), 6.80 (s, 1H Ar), 7.08 (s, 1H Ar), 7.14–7.65 (m, 5H Ar).

5-(2-furyl)-7,8-dimethoxy-1-methyl-1,3-dihydro-1,4-benzodiazepin-2-one, IIah.

By replacing benzene boronic acid in example IIaa by 2-furanboronic acid and proceeding in the same manner, the abovenamed product is obtained. Yield: 43%. M: 172–173° C. $^1$H-NMR (CDCl$_3$, 200 MHz): d 3.38 (s, 3H, NCH$_3$), 3.88 (s, 3H, OCH$_3$), 3.98 (s, 3H, OCH$_3$), 4,28 (AB system, ? d=0.98, $J_{AB}$=10., 2H, CH$_2$), 6.50–6.54 (m, 1H Ar), 6.74–6.77 (m, 2H Ar), 7.07 (s, 1H Ar), 7.59–7.61 (m, 1H Ar).

5-(4-acetylphenyl)-7,8-dimethoxy-1-methyl-1,3-dihydro-1,4-benzodiazepin-2-one, IIai.

By replacing benzene boronic acid in example IIaa by 4-acetylbenzene boronic acid and proceeding in the same manner, the abovenamed product is obtained. Yield: 49%. M: 175–176° C. $^1$H-NMR (CDCl$_3$, 200 MHz): d 2.63 (s, 3H, CH$_3$CO), 3.42 (s, 3H, NCH$_3$), 3.75 (s, 3H, OCH$_3$), 4.00 (s, 3H, OCH$_3$), 4.30 (AB system, ? d=1.03, $J_{AB}$=10.3, 2H, CH$_2$), 6.64 (s, 1H Ar), 6.80 (s, 1H Ar), 7.86 (AB system, ? d=0.23, $J_{AB}$=8.08, 4H Ar).

7,8-dimethoxy-5-(4-N,N-dimethylaminophenyl)-1-methyl-1,3-dihydro-2H-1,4-benzodiazepin-2-one, IIaj.

By replacing benzene boronic acid in example IIaa by 4-N,N-dimethylaminobenzene boronic acid and proceeding in the same manner, the abovenamed product is obtained. Yield: 10%. M: >290° C. $^1$H-NMR (CDCl$_3$, 200 MHz): d 3.02 (s, 6H, NCH$_3$), 3.38 (s, 3H, NCH$_3$), 3.74–3.78 (m, 4H, 1HCH$_2$+OCH$_3$), 3.97 (s, 3H, OCH$_3$), 4.67–4.71 (m, 1HCH$_2$), 6.66–6.81 (m, 4H Ar), 7.54–7.64 (m, 2H Ar). Mass: (M+H)$^+$=354.23.

7,8-dimethoxy-1-methyl-5-(2-thienyl)-1,3-dihydro-1,4-benzodiazepin-2-one, IIak.

By replacing benzene boronic acid in example IIaa by 2-thiophene boronic acid and proceeding in the same manner, the abovenamed product is obtained. Yield: 66%. M: 180–182° C. $^1$H-NMR (CDCl$_3$, 200 MHz): d 3.38 (s, 3H, NCH$_3$), 3.87 (s, 3H, OCH$_3$), 3.99 (s, 3H, OCH$_3$), 4.24 (AB system, ? d=0.91, $J_{AB}$=10.8, 2H, CH$_2$), 6.77 (s, 1H Ar), 7.05–7.49 (m, 4H Ar).

7,8-dimethoxy-5-(3-methoxyphenyl)-1-methyl-1,3-dihydro-1,4-benzodiazepin-2-one, IIal.

By replacing benzene boronic acid in example IIaa by 3-methoxybenzene boronic acid and proceeding in the same manner, the abovenamed product is obtained. Yield: 38%. M: 99–102° C. $^1$H-NMR (CDCl$_3$, 200 MHz): d 3.40 (s, 3H, NCH$_3$), 3.77 (s, 3H, OCH$_3$), 3.86 (s, 3H, OCH$_3$), 3.99 (s, 3H, OCH$_3$), 4.1 (AB system, ? d=0.98, $J_{AB}$=10.7, 2H, CH$_2$), 6.73 (s, 1H Ar), 6.78 (s, 1H Ar), 6.99–7.35 (m, 4H Ar).

7,8-dimethoxy-5-(2-methoxyphenyl)-1-methyl-1,3-dihydro-1,4-benzodiazepin-2-one, IIam.

By replacing benzene boronic acid in example IIaa by 2-methoxybenzene boronic acid and proceeding in the same manner, the abovenamed product is obtained. Yield: 54%. M: 153–154° C. $^1$H-NMR (CDCl$_3$, 200 MHz): d 3.43 (s, 3H, NCH$_3$), 3.57 (s, 3H, OCH$_3$), 3.68 (s, 3H, OCH$_3$), 3.96 (s, 3H, OCH$_3$), 4.31 (AB system, ? d=0.99, $J_{AB}$=10.7, 2H, CH$_2$), 6.53 (s, 1H Ar), 6.75 (s, 1H Ar), 6.86–7.51 (m, 4H Ar).

5-(5-indolyl)-7,8-dimethoxy-1-methyl-1,3-dihydro-1,4-benzodiazepin-2-one, IIan.

By replacing benzene boronic acid in example IIaa by (1-tert-butyloxycarbonylindole)-5-boronic acid and proceeding in the same manner, the abovenamed product is obtained. Yield: 21%. M: 148–151° C. $^1$H-NMR (CDCl$_3$, 300 MHz): d 3.40 (s, 3H, NCH$_3$), 3.92 (s, 3H, OCH$_3$), 4.00 (s, 3H, OCH$_3$), 4.32 (AB system, ? d=0.85, $J_{AB}$=10.9, 2H, CH$_2$), 6.75 (s, 1H Ar), 6.80 (s, 1H Ar), 7.10–7.76 (m, 5H Ar), 9.50 (broad s, 1H exchangeable, NH).

5-(6-benzyloxy-2-naphthyl)-7,8-dimethoxy-1-methyl-1,3-dihydro-1,4-benzodiazepin-2-one, IIao.

By replacing benzene boronic acid in example IIaa by (6-benzyloxynaphthalene-2-boronic acid and proceeding in the same manner, the abovenamed product is obtained. Yield: 18%. M: 143–146° C. $^1$H-NMR (CDCl$_3$, 300 MHz): d 3.43 (s, 3H, NCH$_3$), 3.72 (s, 3H, OCH$_3$), 4.01 (s, 3H, OCH$_3$), 4.34 (AB system, ? d=0.98, $J_{AB}$=10.6, 2H, CH$_2$), 5.21 (s, 2H, CH$_2$), 6.78 (s, 1H Ar), 6.82 (s, 1H Ar), 7.33–8.02 (m, 11H Ar).

7,8-dimethoxy-5-(6-methoxy-2-naphthyl)-1-methyl-1,3-dihydro-1,4-benzodiazepin-2-one, IIap.

By replacing benzene boronic acid in example IIaa by (6-methoxynaphthalene-2-boronic acid and proceeding in the same manner, the abovenamed product is obtained. Yield: 40%. M: 193–194° C. $^1$H-NMR (CDCl$_3$, 300 MHz): d 3.43 (s, 3H, NCH$_3$), 3.72 (s, 3H, OCH$_3$), 3.95 (s, 3H, OCH$_3$), 4.01 (s, 3H, OCH$_3$), 4.34 (AB system, ? d=0.98, $J_{AB}$=10.6, 2H, CH$_2$), 6.79 (s, 1H Ar), 6.82 (s, 1H Ar), 7.16–8.00 (m, 6H Ar).

5-(2-indolyl)-7,8-dimethoxy-1-methyl-1,3-dihydro-1,4-benzodiazepin-2-one, IIaq.

By replacing benzene boronic acid in example IIaa by (1-tert-butyloxycarbonylindole)-2-boronic acid and proceeding in the same manner, the abovenamed product is obtained. Yield: 21%. M: 146–148° C. $^1$H-NMR (CDCl$_3$, 200 MHz): d 3.39 (s, 3H, NCH$_3$), 3.89 (s, 3H, OCH$_3$), 4.00 (s, 3H, OCH$_3$), 4.31 (AB system, ? d=0.87, $J_{AB}$=10.8, 2H, CH$_2$), 6.75 (s, 1H Ar), 6.79 (s, 1H Ar), 7.12–7.65 (m, 5H Ar).

7,8-dimethoxy-1-methyl-5-(piperidin-1-yl)-1,3-dihydro-1,4-benzodiazepin-2-one, IIar.

Heat at 110° C. in a sealed tube a mixture of 100 mg (0.37 mmol) of 5-chloro-7,8-dimethoxy-1-methyl-1,3-dihydro-1,4-benzodiazepin-2-one XVIIIaa and 300 μl (3 mmol) of piperidine in 10 ml of EtOH for 48 hours. Evaporate to dryness and purify by silica chromatography (CH$_2$Cl$_2$ 50/AcOEt 40/EtOH 10). Triturate in hexane, filter, dry. One obtains 70 mg of a beige powder. Yield: 60%. M=125–127° C. $^1$H-NMR (200 MHz, DMSO): δ 1.63–1.70 (m, 6H, 3×CH$_2$), 3.20–3.23 (m, 4H, 2×CH$_2$), 3.37 (s, 3H, NCH$_3$), 3.91 (AB system, Δδ=0.71, $J_{AB}$=11.5, 2H, 3-CH$_2$), 3.94 (s, 3H, OCH$_3$), 3.97 (s, 3H, OCH$_3$), 6.73 (s, 1H Ar), 6.99 (s, 1H Ar).

7,8-dimethoxy-1-methyl-5-[(E)-2-phenylethenyl]-1,3-dihydro-2H-1,4-benzodiazepin-2-one, IIas.

By replacing benzene boronic acid in example IIaa by (E)-2-phenylethenyl boronic acid and proceeding in the same manner, the abovenamed product is obtained. Yield: 20%. $^1$H-NMR (CDCl$_3$, 300 MHz): d 3.38 (s, 3H, NCH$_3$), 3.76 (s, 3H, OCH$_3$), 3.98 (s, 3H, OCH$_3$), 4,26 (AB system, ? d=0.93, $J_{AB}$=10.6, 2H, CH$_2$), 6.77 (s,1H Ar), 7.00 (s, 1H, =CHPh), 7.12 (s, 2H, =CH+1H Ar) 7.34–751 (m, 5H Ar). Mass: (M+H)$^+$=337.21.

7,8-dimethoxy-1-methyl-5-(2-phenylethynyl)-1,3-dihydro-2H-1,4-benzodiazepin-2-one, IIat.

To a solution of 240 mg (0.89 mmol) of 5-chloro-7,8-dimethoxy-1-methyl-1,3-dihydro-1,4-benzodiazepin-2-one XVIIIaa in 7 ml of CH$_3$CN, add under an inert atmosphere 17 mg (0.1 mmol) of PdCl$_2$, 30 mg (0.16 mmol) of CuI. Stir for 5 minutes, then add 68 mg (0.23 mmol) of PPh$_3$, 185 µl of Net$_3$ and 150 µl of phenylacetylene. Heat the mixture at 55° C. for 3 hours. Evaporate to dryness and purify by silica chromatography (AcOEt 1/hexane 1, then AcOEt). Recrystallize in EtOH. Yield: 45%. $^1$H-NMR (DMSO, 200 MHz): d 3.33 (s, 3H, NCH$_3$), 3.70–3.91 (m, 7H, 1HCH$_2$+2OCH$_3$), 4.50–5.60 (m, 1HCH$_2$), 7.06 (s, 1H Ar), 7.32 (s, 1H Ar), 7.48–7.68 (m, 5H Ar). Mass: (M+H)$^+$=335.16.

7,8-dimethoxy-1-methyl-5-(2-methylphenyl)-1,3-dihydro-1,4-benzodiazepin-2-one, IIau.

By replacing benzene boronic acid in example IIaa by 2-methylbenzene boronic acid and proceeding in the same manner, the abovenamed product is obtained. Yield: 30%. M: 139–141° C. $^1$H-NMR (CDCl$_3$, 300 MHz): d 1.99 (s, 3H, CH$_3$), 3.44 (s, 3H, NCH$_3$), 3.66 (s, 3H, OCH$_3$), 3.98 (s, 3H, OCH$_3$), 4.31 (system AB, ?d=0.99, J$_{AB}$=10.3, 2H, CH$_2$), 6.46 (s, 1H Ar), 6.77 (s, 1H Ar), 7.15–7.41 (m, 4H Ar).

7,8-dimethoxy-1-methyl-5-(N-tetrahydro-1,2,3,4-isoquinolyl)-1,3-dihydro-2H-1,4-benzodiazepin-2-one, IIav.

By replacing piperidine in example IIar by tetrahydro-1,2,3,4-isoquinoline and proceeding in the same manner, the abovenamed product is obtained. Yield: 35%. M: 154–157° C. $^1$H-NMR (DMSO, 300 MHz): d 2.70–3.10 (m, 2H, CH$_2$), 3.23 (s, 3H, NCH$_3$), 3.41–3.54 (m, 3H, 1CH$_2$+1HCH$_2$), 3.78 (s, 3H, OCH$_3$), 3.88 (s, 3H, OCH$_3$), 3.98–4.01 (m, 1HCH$_2$), 4.33–4.44 (m, 2H, CH$_2$), 6.97 (s, 1H Ar), 7.02 (s, 1H Ar), 7.15 (s, 4H Ar). Mass: (M+H)$^+$=366.19.

7,8-dimethoxy-5-(4-methoxyphenyl)-1-methyl-1,3-dihydro-1,4-benzodiazepin-2-one, IIaw.

By replacing benzene boronic acid in example IIaa by 4-methoxybenzene boronic acid and proceeding in the same manner, the abovenamed product is obtained. Yield: 30%. M: 163–165° C. $^1$H-NMR (CDCl$_3$, 200 MHz): d 3.39 (s, 3H, NCH$_3$), 3.76 (s, 3H, OCH$_3$), 3.86 (s, 3H, OCH$_3$), 3.98 (s, 3H, OCH$_3$), 4.25 (AB system, ? d=0.98, J$_{AB}$=10.5, 2H, CH$_2$), 6.74–6.93 (m, 4H Ar), 7.59 (s, 1H Ar), 7.63 (s, 1H Ar).

5-(3-bromophenyl)-7,8-dimethoxy-1-methyl-1,3-dihydro-2H-1,4-benzodiazepin-2-one, IIax.

By replacing benzene boronic acid in example IIaa by 3-bromobenzene boronic acid and proceeding in the same manner, the abovenamed product is obtained. Yield: 38%. $^1$H-NMR (DMSO, 200 MHz): d 3.33 (s, 3H, NCH$_3$), 3.66 (s, 3H, OCH$_3$), 3.92 (s, 3H, OCH$_3$), 4,23 (AB system, ?d=0.98, J$_{AB}$=10, 2H, CH$_2$), 6.72 (s, 1H Ar), 7.12 (s, 1H Ar), 7.37–7.80 (m, 4H Ar).

5-(1,1'-biphenyl-3-yl)-7,8-dimethoxy-1-methyl-1,3-dihydro-2H-1,4-benzodiazepin-2-one, IIay.

Heat at 115° C. for 12 hours under an inert atmosphere a mixture of 100 mg (0.26 mmol) of 5-(3-bromophenyl)-7,8-dimethoxy-1-methyl-1,3-dihydro-2H-1,4-benzodiazepin-2-one IIax, 38 mg (0.31 mmol) of benzene boronic acid, 63 mg (0.30 mmol) of K$_3$PO$_4$, 9 mg (0.020 mmol) of tetrakis (triphenylphosphine)Pd(0) in 1 ml of DMF. Allow to cool to room temperature. Add 80 ml of H$_2$O and extract three times with 50 ml of Et$_2$O. Dry the organic fractions on Na$_2$SO$_4$. Purify by chromatography (AcOEt 1/hexane 1). Recrystallize in EtOH. One obtains 13 mg of the abovenamed powder as colorless crystals. Yield: 13%. M: 127° C. $^1$H-NMR (CDCl$_3$, 200 MHz): d 3.42 (s, 3H, NCH$_3$), 3.77 (s, 3H, OCH$_3$), 4.00 (s, 3H, OCH$_3$), 4.34 (AB system, ?d=1.00, J$_{AB}$=10.5, 2H, CH$_2$), 6.78 (s, 1H Ar), 6.80 (s, 1H Ar), 7.39–7.90 (m, 9H Ar).

7,8-dimethoxy-1-methyl-5-(2-phenylethyl)-1,3-dihydro-2H-1,4-benzodiazepin-2-one, IIaz.

Stir a mixture of 80 mg (0.24 mmol) of 7,8-dimethoxy-1-methyl-5-(2-phenylethynyl)-1,3-dihydro-1,4-benzodiazepin-2-one 132, 15 mg of 10% Pd/C by weight in 5 ml of MeOH and 5 ml of CH$_2$Cl$_2$ under 70 psi of H$_2$ for 48 hours. Filter the suspension on celite, rinse three times with 10 ml of MeOH. Evaporate to dryness and purify by silica chromatography (AcOEt 1/hexane 1, then AcOEt). Yield: 5%. M: 112–115° C. $^1$H-NMR (CDCl$_3$, 300 MHz): d 2.95–3.07 (m, 4H, CH$_2$CH$_2$), 3.28 (s, 3H, NCH$_3$), 3.87 (s, 3H, OCH$_3$), 3.93 (s, 3H, OCH$_3$), 4.10 (AB system, ? d=0.96, J$_{AB}$=10.2, 2H, CH$_2$), 6.67 (s, 1H Ar), 6.78 (s, 1H Ar), 7.15–7.25 (m, 5H Ar). Mass: (M+H)$^+$=339.15

EXAMPLE 4

Synthesis of Compounds Represented by General Formula II According to the Invention by a Second Route 4.1. Synthesis of Intermediates.

2-ethoxy-1-methoxy-4-nitrobenzene, XIXaa.

Under an inert atmosphere at 0° C., add a solution of 10 g (59 mmol) of 2-ethoxy-5-nitrophenol dissolved in 125 ml of DMF, on a solution of 2.6 g (65 mmol) of 60% NaH in oil dissolved in 125 ml of DMF. After 30 minutes at room temperature, add dropwise 5.2 ml (65 mmol) of EtI at 0° C. Allow to stand at room temperature for 12 hours. Add 1.5 l of a water-ice mixture. Filter the precipitate and wash three times with 100 ml of water then once with 100 ml of pentane. One obtains 9.8 g of the abovenamed product in the form of a white powder. Yield: 93%. $^1$H-NMR (CDCl$_3$, 300 MHz): d 1.52 (t, 3H, —CH$_3$), 3.98 (s, 3H, OCH$_3$), 4.20 (q, 2H, OCH$_2$), 6.91 (d, 1H Ar), 7.75 (d, 1H Ar), 7.91 (dd,1H Ar).

1,2-diethoxy-4-nitrobenzene, XIXab.

Under an inert atmosphere at 0° C., add a solution of 20 g (0.13 mol) of 4-nitrobenzene-1,2-diol dissolved in 150 ml of DMF, on a solution of 11.35 g (0.28 mol) of 60% NaH dissolved in 150 ml of DMF. After 30 minutes at room temperature, add dropwise 5.2 ml (65 mmol) of EtI at 0° C. Allow to stand at room temperature for 12 hours. Add 2 l of a water-ice mixture. Filter the precipitate and wash three times with 100 ml of water then once with 100 ml of pentane. One obtains 20.4 g of the abovenamed product in the form of a white powder. Yield: 76%. $^1$H-NMR (CDCl$_3$, 300 MHz): d 1.47–1.53 (m, 6H, 2×—CH$_3$), 4.14–4.20 (m, 4H, 2×OCH$_2$), 6.88 (d, 1H Ar), 7.74 (d, 1H Ar), 7.89 (dd, 1H Ar).

3-ethoxy-4-methoxyaniline, XXaa.

Leave under hydrogen pressure (Patm) for 12 hours, 5 g of 2-ethoxy-1-methoxy-4-nitrobenzene (XIXaa), 500 mg of 10% palladium on charcoal (10% by weight of product to reduce), in 200 ml of methanol. Filter on celite, rinse several times with methanol. Evaporate to dryness. Take up in ether and evaporate. One obtains 3.28 g of the abovenamed product as a pinkish white powder. Yield: 79%. $^1$H-NMR (CDCl$_3$, 300 MHz): d 1.46 (t, 3H, —CH$_3$), 3.33 (s, 2H exchangeable, —NH$_2$), 3.81 (s, 3H, OCH$_3$), 4.05 (q, 2H, OCH$_2$), 6.22(d, 1H Ar), 6.28 (dd, 1H Ar), 6.71 (d, 1H Ar).

3,4-diethoxyaniline, XXab.

By replacing 2-ethoxy-1-methoxy-4-nitrobenzene (XIXaa) in example XXaa by 1,2-diethoxy-4-nitrobenzene (XIXab) and proceeding in the same manner, the abovenamed product is obtained. Yield: 80%. $^1$H-NMR (CDCl$_3$, 300 MHz): d 1.36–1.46 (m, 6H, 2 times —CH$_3$), 3.44 (s, 2H exchangeable, —NH$_2$), 3.97–4.07 (m, 4H, 2×OCH$_2$), 6.19 (dd, 1H Ar), 6.23 (d, 1H Ar), 6.73 (d, 1H Ar).

(2-amino-4,5-dimethoxyphenyl)(phenyl)methanone, XXIaa.

Under an inert atmosphere at 0° C., add to a solution of 35 ml of boron tribromide (1M/CH$_2$Cl$_2$, 35.8 mmol), 5 g of 3,4-dimethoxyaniline (32.6 mmol) dissolved in 30 ml of dichloroethane, 6.7 ml of benzonitrile (65.2 mmol), and 4.79 g of AlCl$_3$ (35.8 mmol). Stir at room temperature for 30 minutes. Evaporate the dichloromethane. Heat under reflux for 12 hours. Allow to cool. Add 35 ml of 1 M HCl at 0° C., stir at 75° C. for 1 hour. Add 150 ml of water and extract three times with 200 ml of CH$_2$Cl$_2$. Dry the organic fractions on Na$_2$SO$_4$. Purify by chromatography (AcOEt 1/hexane 2). One obtains 6.1 g of the abovenamed product as a yellow powder. Yield: 73%. $^1$H-NMR (CDCl$_3$, 300 MHz): d 3.66 (s, 3H, —OCH$_3$), 3.92 (s, 3H, —OCH$_3$), 6.22 (s, 2H exchangeable+1H, 1H Ar$^{+-NH_2}$), 6.95 (s, 1H Ar), 7.46–7.51 (m, 3H Ar), 7.61–7.64 (m, 2H Ar).

(2-amino-4-bromophenyl)(4-bromophenyl)methanone, XXIab.

By replacing 3,4-dimethoxyaniline in example XXIaa by 3-bromoaniline, and benzonitrile by 4-bromobenzonitrile, and proceeding in the same manner, the abovenamed product is obtained. Yield: 17%. $^1$H-NMR (CDCl$_3$, 200 MHz): 6.18 (s, 2H exchangeable, —NH$_2$), 6.76 (dd, 1H Ar), 6.97 (d, 1H Ar), 7.30 (t, 1H Ar), 7.61 (AB system, ? d=0.13, J$_{AB}$=8.3, 4H Ar).

(2-amino-5-iodophenyl) [3-(trifluoromethyl)phenyl]methanone, XXIac.

By replacing 3,4-dimethoxyaniline in example XXIaa by 4-iodoaniline, and benzonitrile by 3-trifluoromethyl-benzonitrile, and proceeding in the same manner, the abovenamed product is obtained. Yield: 10%. $^1$H-NMR (DMSO, 300 MHz): d 6.41 (d, 2H Ar), 6.74 (m, 1H Ar), 7.06 (d, 1H Ar), 7.26–7.38 (m, 2H Ar), 7.55–7.58 (m, 1H Ar).

2-amino-3-bromo-4,5-dimethoxybenzophenone, XXIad

To a solution of 900 mg (3.5 mmol) of (2-amino-4,5-dimethoxyphenyl)(phenyl)methanone (XXIaa) in 60 ml of DMSO, add dropwise at 0° C. 15 g of HBr 40% by weight in water. Heat at 60° C. for 24 hours. Add 400 ml of H$_2$O and extract four times with 200 ml of AcOEt; dry on MgSO$_4$, evaporate the AcOEt and purify by silica chromatography (AcOEt 1/hexane 4). Yield: 65%. $^1$H-NMR (CDCl$_3$, 300 MHz): d 3.67 (s, 3H, OCH$_3$), 3.97 (s, 3H, OCH$_3$), 6.59 (s, 2H, NH$_2$), 7.06 (s, 1H Ar), 7.47–7.65 (m, 5H Ar). Mass: (M+H)$^+$=335.98+337.98.

(2-amino-5-methoxyphenyl)[3-(trifluoromethyl)phenyl]methanone, XXIae.

By replacing 3,4-dimethoxyaniline in example XXIaa by 4-methoxyaniline, and benzonitrile by 3-trifluoromethyl-benzonitrile, and proceeding in the same manner, the abovenamed product is obtained. Yield: 23%. $^1$H-NMR (CDCl$_3$, 200 MHz): d 3.70 (s, 3H, OCH$_3$), 6.18–6.24 (m, 2H Ar), 6.35 (s, 2H exchangeable, —NH$_2$), 7.35–7.81 (m, 6H Ar).

(2-amino-4,5-dimethoxyphenyl)(4-bromophenyl)methanone, XXIaf.

By replacing benzonitrile in example XXIaa by 4-bromobenzonitrile and proceeding in the same manner, the abovenamed product is obtained. Yield: 82%. $^1$H-NMR (CDCl$_3$, 300 MHz): d 3.67 (s, 3H, —OCH$_3$), 3.91 (s, 3H, —OCH$_3$), 6.20 (s, 2H exchangeable+1H, 1H Ar$^{+-NH_2}$), 6.86 (s, 1H Ar), 7.55 (AB system, ? d=0.10, J$_{AB}$=8.7, 4H Ar).

(2-amino-4,5-diethoxyphenyl)(phenyl)methanone, XXIag.

By replacing 3,4-dimethoxyaniline in example XXIaa by 3,4-diethoxyaniline (XXab). By purifying by chromatography (AcOEt 1/hexane 4), and proceeding in the same manner, the abovenamed product is obtained. Yield: 35%. $^1$H-NMR (CDCl$_3$, 300 MHz): d 1.32 (t, 3H, —CH$_3$), 1.48 (t, 3H, —CH$_3$), 3.85 (q, 2H, OCH$_2$), 4.10 (q, 2H, OCH$_2$), 6.19 (s, 1H Ar), 6.23 (s, 2H exchangeable, —NH$_2$), 6.99 (s, 1H Ar), 7.42–7.62 (m, 5H Ar).

(7-amino-2,3-dihydro-1,4-benzodioxin-6-yl)(phenyl)methanone, XXIah.

By replacing 3,4-dimethoxyaniline in example XXIaa by 2,3-dihydro-1,4-benzodioxin-6-amine and proceeding in the same manner, the abovenamed product is obtained. Yield: 49%. The product is used as is.

(2-amino-4,5-dimethoxyphenyl)(3-bromophenyl)methanone, XXIai.

By replacing benzonitrile in example XXIaa by 3-bromobenzonitrile and proceeding in the same manner, the abovenamed product is obtained. Yield: 32%. $^1$H-NMR (CDCl$_3$, 300 MHz): d 3.70 (s, 3H, —OCH$_3$), 3.95 (s, 3H, —OCH$_3$), 6.23 (s, 1H Ar), 6.28 (s, 2H exchangeable, —NH$_2$), 6.88 (s, 1H Ar), 7.32 (s, 1H Ar), 7.40 (s, 1H Ar), 7.53–7.59 (m, 1H Ar), 7.63–7.69 (m, 1H Ar), 7.78–7.80 (m, 1H Ar).

(2-amino-4,5-dimethoxyphenyl)(2-bromophenyl)methanone, XXIaj.

By replacing benzonitrile in example XXIaa by 2-bromobenzonitrile and proceeding in the same manner, the abovenamed product is obtained. Yield: 30%. $^1$H-NMR (CDCl$_3$, 200 MHz): d 3.60 (s, 3H, —OCH$_3$), 3.92 (s, 3H, —OCH$_3$), 6.20 (s, 1H Ar), 6.51 (s, 2H exchangeable, —NH$_2$), 6.57 (s, 1H Ar), 7.29–7.42 (m, 3H Ar), 6.64–7.69 (m, 1H Ar).

(2-amino-4-ethoxy-5-methoxyphenyl)(phenyl)methanone, XXIak.

By replacing 3,4-dimethoxyaniline in example XXIaa by 3-ethoxy-4-methoxyaniline (XXaa). By purifying by chromatography (AcOEt 1/hexane 4) and proceeding in the same manner, the abovenamed product is obtained. Yield: 53%. $^1$H-NMR (CDCl$_3$, 300 MHz): d 1.52 (t, 3H, —CH$_3$), 3.66 (s, 3H, OCH$_3$), 4.13 (q, 2H, OCH$_2$), 6.19 (s, 2H exchangeable, —NH$_2$), 6.20 (s, 1H Ar) 6.95 (s, 1H Ar), 7.43–7.64 (m, 5H Ar).

(2-amino-4-methoxyphenyl)(phenyl)methanone, XXIal.

By replacing 3,4-dimethoxyaniline in example XXIaa by 3-methoxyaniline. By purifying by chromatography (AcOEt 1/hexane 4) and proceeding in the same manner, the abovenamed product is obtained. Yield: 68%. $^1$H-NMR (CDCl$_3$, 300 MHz): d 3.82 (s, 3H, OCH$_3$), 6.15–6.20 (m, 2H Ar), 6.37 (s, 2H exchangeable, —NH$_2$), 7.38–7.65 (m, 6H Ar).

(2-amino-5-methoxyphenyl)(phenyl)methanone, XXIam.

By replacing 3,4-dimethoxyaniline in example XXIaa by 4-methoxyaniline. By purifying by chromatography (AcOEt 1/hexane 4) and proceeding in the same manner, the abovenamed product is obtained. Yield: 43%. $^1$H-NMR (CDCl$_3$, 300 MHz): d 3.66 (s, 3H, OCH$_3$), 5.72 (s, 2H exchangeable, —NH$_2$), 6.73 (d, 1H Ar), 6.96–7.02 (m, 2H Ar), 7.44–7.54 (m, 3H Ar), 7.67–7.70 (m, 2H Ar).

(2-amino-5-hydroxy-4-methoxyphenyl)(phenyl)methanone, XXIan.

To 400 mg (1.55 mmol) of (2-amino-4,5-dimethoxyphenyl)(phenyl)methanone (XXIaa), add dropwise 2.1 ml of HBr 40% by weight in water. Heat at 95° C. for 12 hours. At 0° C. add ammonia to pH=8.9. Add 100 ml H$_2$O and extract three times with 100 ml of CH$_2$Cl$_2$. Dry on MgSO$_4$, evaporate the CH$_2$Cl$_2$ and purify by silica chromatography (AcOEt 1/hexane 4 then 1/1). Yield: 45%. $^1$H-NMR (CDCl$_3$, 200 MHz): d 3.92 (s, 3H, OCH$_3$), 6.20 (s, 1H Ar), 7.00 (s, 1H Ar), 7.42–7.61 (m, 5H Ar).

(2-amino-5-ethoxy-4-methoxyphenyl)(phenyl)methanone, XXIao.

At 0° C. under an inert atmosphere, add 50 mg (1.25 mmol) of 60% NaH in oil to a solution of 300 mg (1.23 mmol) of (2-amino-5-hydroxy-4-methoxyphenyl)(phenyl)methanone (XXIan) in 5 ml of DMF. Stir at room temperature for 1 hour. Add dropwise at 0° C. 210 mg (1.35 mmol) of ethyl iodide. Stir at room temperature overnight. Add 50 ml of H$_2$O and extract three times with 50 ml of AcOEt; dry on MgSO$_4$, evaporate the AcOEt and purify by silica chromatography (AcOEt 1/hexane 1). Yield: 85%. $^1$H-NMR (CDCl$_3$, 300 MHz): d 1.26–1.36 (m, 3H, OCH$_2$CH$_3$), 3.81–3.87 (m, 2H, OCH$_2$CH$_3$), 3.90 (s, 3H, OCH$_3$), 6.20 (s, 1H Ar), 6.96 (s, 1H Ar), 7.42–7.61 (m, 4H Ar).

4.2. Synthesis of compounds represented by formula XXII
The following compounds were synthesized:
7,8-dimethoxy-5-phenyl-1,3-dihydro-2H-1,4-benzodiazepin-2-one, XXIIaa.
8-bromo-5-(4-bromophenyl)-1,3-dihydro-2H-1,4-benzodiazepin-2-one, XXIIab.
7-iodo-5-[3-(trifluoromethyl)phenyl]-1,3-dihydro-2H-1,4-benzodiazepin-2-one, XXIIac.
7,8-dimethoxy-3-isobutyl-5-phenyl-1,3-dihydro-2H-1,4-benzodiazepin-2-one, XXIIad.
7-methoxy-5-[3-(trifluoromethyl)phenyl]-1,3-dihydro-2H-1,4-benzodiazepin-2-one, XXIIae.
5-(4-bromophenyl)-7,8-dimethoxy-1,3-dihydro-2H-1,4-benzodiazepin-2-one, XXIIaf.
7,8-diethoxy-5-phenyl-1,3-dihydro-2H-1,4-benzodiazepin-2-one, XXIIag.
10-phenyl-2,3,6,8-tetrahydro-7H-[1,4]dioxino[2,3-h][1,4]benzodiazepin-7-one, XXIIah.
7,8-diethoxy-3-methyl-5-phenyl-1,3-dihydro-2H-1,4-benzodiazepin-2-one, XXIIai.
3-benzyl-7,8-diethoxy-5-phenyl-1,3-dihydro-2H-1,4-benzodiazepin-2-one, XXIIaj.
5-(3-bromophenyl)-7,8-dimethoxy-1,3-dihydro-2H-1,4-benzodiazepin-2-one, XXIIak.
5-(2-bromophenyl)-7,8-dimethoxy-1,3-dihydro-2H-1,4-benzodiazepin-2-one, XXIIal.
8-ethoxy-7-methoxy-5-phenyl-1,3-dihydro-2H-1,4-benzodiazepin-2-one, XXIIam.
8-methoxy-5-phenyl-1,3-dihydro-2H-1,4-benzodiazepin-2-one, XXIIan.
7-methoxy-5-phenyl-1,3-dihydro-2H-1,4-benzodiazepin-2-one, XXIIao.
3-benzyl-7,8-dimethoxy-5-phenyl-1,3-dihydro-2H-1,4-benzodiazepin-2-one, XXIIap.
7,8-dimethoxy-3-methyl-5-phenyl-1,3-dihydro-2H-1,4-benzodiazepin-2-one, XXIIaq.
7,8-dimethoxy-3-(1H-imidazol-4-ylmethyl)-5-phenyl-1,3-dihydro-2H-1,4-benzodiazepin-2-one, XXIIar.
7,8-dimethoxy-3-(1H-indol-3-ylmethyl)-5-phenyl-1,3-dihydro-2H-1,4-benzodiazepin-2-one, XXIIas.
7,8-dimethoxy-3-(2-methylthioethyl)-5-phenyl-1,3-dihydro-2H-1,4-benzodiazepin-2-one, XXIIat.
(S) 3-benzyl-7,8-dimethoxy-5-phenyl-1,3-dihydro-2H-1,4-benzodiazepin-2-one, XXIIau.
(7,8-dimethoxy-5-phenyl-2-oxo-2,3-dihydro-1H-1,4-benzodiazepin-3-yl)benzyl(S)-butylcarbamate, XXIIav.
(S)-3-(4-aminobutyl)-7,8-dimethoxy-5-phenyl-1,3-dihydro-2H-1,4-benzodiazepin-2-one, XXIIaw.
(S)-N-[4-(7,8-dimethoxy-2-oxo-5-phenyl-2,3-dihydro-1H-1,4-benzodiazepin-3-yl)butyl]acetamide, XXIIax.
N-[4-(7,8-dimethoxy-2-oxo-5-phenyl-2,3-dihydro-1H-1,4-benzodiazepin-3-yl)butyl]guanidinium (S)-bis trifluoroacetate, XXIIay.
7,8-dimethoxy-3,5-diphenyl-1,3-dihydro-2H-1,4-benzodiazepin-2-one, XXIIaz.
3,5-diphenyl-8-ethoxy-7-methoxy-1,3-dihydro-2H-1,4-benzodiazepin-2-one, XXIIba.
3-benzyl-8-ethoxy-7-methoxy-5-phenyl-1,3-dihydro-2H-1,4-benzodiazepin-2-one, XXIIbb.
5-phenyl-7-ethoxy-8-methoxy-1,3-dihydro-2H-1,4-benzodiazepin-2-one, XXIIbc.

7,8-dimethoxy-5-phenyl-1,3-dihydro-2H-1,4-benzodiazepin-2-one, XXIIaa.

Heat under reflux for 36 hours under an inert atmosphere a mixture of 4.5 g (17.6 mmol) of (2-amino-4,5-dimethoxyphenyl)(phenyl)methanone (XXIaa), 5 g (36 mmol) of ethyl glycinate hydrochloride, and 30 ml of anhydrous pyridine. Add four 2.5 g (18 mmol) fractions of ethyl glycinate hydrochloride, every 6 hours. Allow to equilibrate to room temperature. Evaporate to dryness. Add 200 ml of water. Extract three times with 300 ml of dichloromethane. Dry the organic fractions on Na$_2$SO$_4$ Purify by chromatography (AcOEt 3/hexane 1/3% triethylamine). Recrystallize in EtOH/EtO$_2$. One obtains 2.2 g of the abovenamed product in the form of colorless crystals. Yield: 43%. M:248–250° C. $^1$H-NMR (CDCl$_3$, 200 MHz): d 3.71 (s, 3H, OCH$_3$), 3.95 (s, 3H, OCH$_3$), 4.31 (s, 2H, CH$_2$), 6.64 (s, 1H Ar), 6.70 (s, 1H Ar), 7.27–7.59 (m, 5H Ar), 9.40 (s, 1H exchangeable, —NH).

8-bromo-5-(4-bromophenyl)-1,3-dihydro-2H-1,4-benzodiazepin-2-one, XXIIab.

By replacing (2-amino-4,5-dimethoxyphenyl)(phenyl)methanone (XXIaa) in example XXIIaa by (2-amino-4-bromophenyl)(4-bromophenyl) methanone (XXIab) and proceeding in the same manner, the abovenamed product is obtained. Yield: 3%. M: 299° C. $^1$H-NMR (DMSO, 200 MHz): d 4.18 (s, 2H, CH$_2$), 7.21 (d, 1H Ar), 7.35–7.46 (m, 5H Ar), 7.63–7.68 (m, 2H Ar), 10.65 (s, 1H exchangeable, —NH).

7-iodo-5-[3-(trifluoromethyl)phenyl]-1,3-dihydro-2H-1,4-benzodiazepin-2-one, XXIIac.

By replacing (2-amino-4,5-dimethoxyphenyl)(phenyl)methanone (XXIaa) in example XXIIaa by (2-amino-5-iodophenyl)[3-(trifluoromethyl)phenyl]methanone (XXIac) and proceeding in the same manner, the abovenamed product is obtained. Yield: 5%. M: 209° C. $^1$H-NMR (CDCl$_3$, 200 MHz): d 4.36 (s, 2H, CH$_2$), 6.92 (d, 1H Ar), 7.51–7.59 (m, 2H Ar), 7.76–7.89 (m, 4H Ar), 8.30 (s, 1H exchangeable, —NH).

7,8-dimethoxy-3-isobutyl-5-phenyl-1,3-dihydro-2H-1,4-benzodiazepin-2-one, XXIIad.

By replacing ethyl glycinate hydrochloride in example XXIIaa by ethyl leucinate hydrochloride and proceeding in the same manner, the abovenamed product is obtained. Yield: 30%. M: 198–201° C. $^1$H-NMR (CDCl$_3$, 300 MHz):

d 0.85–0.87 (m, 3H, CH₃), 1.03–1.05 (m, 3H, CH₃), 1.94–2.05 (m, 2H, CH₂), 2.3–2.4 (m, 1HCH₂), 3.62–3.68 (m, 1HCH₂), 3.74 (s, 3H, OCH₃), 3.96 (s, 3H, OCH₃), 6.63 (s, 1H Ar), 6.73 (s, 1H Ar), 7.37–7.58 (m, 5H Ar), 9.04 (s, 1H, NH).

7-methoxy-5-[3-(trifluoromethyl)phenyl]-1,3-dihydro-2H-1,4-benzodiazepin-2-one, XXIIae.

By replacing (2-amino-4,5-dimethoxyphenyl)(phenyl) methanone (XXIaa) in example XXIIaa by (2-amino-5-methoxyphenyl)[3-(trifluoromethyl) phenyl]methanone (XXIae) and proceeding in the same manner, the abovenamed product is obtained. Yield: 75%. M: 197–199° C. ¹H-NMR (DMSO, 300 MHz): d 3.68 (s, 3H, OCH₃), 4.16 (s, 2H, CH₂), 6.74 (s, 1H Ar), 7,23 (s, 1H Ar), 7.68–7.90 (m, 4H Ar), 10.41 (s, 1H exchangeable, —NH).

5-(4-bromophenyl)-7,8-dimethoxy-1,3-dihydro-2H-1,4-benzodiazepin-2-one, XXIIaf.

By replacing (2-amino-4,5-dimethoxyphenyl)(phenyl) methanone (XXIaa) in example XXIIaa by (2-amino-4,5-dimethoxyphenyl)(4-bromophenyl) methanone (XXIaf) and proceeding in the same manner, the abovenamed product is obtained. Yield: 43%. Yield: 73%. ¹H-NMR (CDCl₃, 200 MHz): d 3.74 (s, 3H, OCH₃), 3.96 (s, 3H, OCH₃), 4.30 (s, 2H, CH₂), 6.78 (s, 1H Ar), 6.80 (s, 1H Ar), 7.50 (AB system, ? d=0.08, $J_{AB}$=8.3, 4H Ar), 8.75 (s, 1H exchangeable, —NH).

7,8-diethoxy-5-phenyl-1,3-dihydro-2H-1,4-benzodiazepin-2-one, XXIIag.

By replacing (2-amino-4,5-dimethoxyphenyl)(phenyl) methanone (XXIaa) in example XXIIaa by (2-amino-4,5-diethoxyphenyl)(phenyl)methanone (XXIag) and proceeding in the same manner, the abovenamed product is obtained. Yield: 60%. M: 233–236° C. ¹H-NMR (CDCl₃, 200 MHz): d 1.39 (t, 3H, CH₃), 1.54 (t, 3H, CH₃), 3.94 (q, 2H, OCH₂), 4.18 (q, 2H, OCH₂), 4.35 (s, 2H, CH₂), 6.66 (s, 1H Ar), 6.74 (s, 1H Ar), 7.36–7.63 (m, 5H Ar), 9,51 (s, 1H exchangeable, —NH).

10-phenyl-2,3,6,8-tetrahydro-7H-[1,4]dioxino[2,3-h][1,4] benzodiazepin-7-one, XXIIah.

By replacing (2-amino-4,5-dimethoxyphenyl)(phenyl) methanone (XXIaa) in example XXIIaa by (7-amino-2,3-dihydro-1,4-benzodioxin-6-yl)(phenyl) methanone (XXIah) and proceeding in the same manner, the abovenamed product is obtained. Yield: 15%. M: 263–265° C. ¹H-NMR (CDCl₃, 200 MHz): d 4.21–4.49 (m, 6H, —OCH₂CH₂O— + CH₂), 6.64 (s, 1H Ar), 6.80 (s, 1H Ar), 7.32–7.58 (m, 5H Ar), 8,37 (s, 1H exchangeable, —NH).

7,8-diethoxy-3-methyl-5-phenyl-1,3-dihydro-2H-1,4-benzodiazepin-2-one, XXIIai.

By replacing (2-amino-4,5-dimethoxyphenyl)(phenyl) methanone (XXIaa) in example XXIIaa by (2-amino-4,5-diethoxyphenyl)(phenyl)methanone (XXIag), and ethyl glycinate hydrochloride by methyl analitate hydrochloride, and proceeding in the same manner, the abovenamed product is obtained. Yield: 13%. M:195–198° C. ¹H-NMR (CDCl₃, 200 MHz): d 1.39 (t, 3H, CH₃), 1.54 (t, 3H, CH₃), 1.77 (d, 3H, CH₃), 3.80 (q, 1H, CH), 3.94 (q, 2H, OCH₂), 4.18 (q, 2H, OCH₂), 6.64 (s, 1H Ar), 6.75 (s, 1H Ar), 7.36–7.63 (m, 5H Ar), 9.10 (s, 1H exchangeable, —NH).

3-benzyl-7,8-diethoxy-5-phenyl-1,3-dihydro-2H-1,4-benzodiazepin-2-one, XXIIaj.

By replacing (2-amino-4,5-dimethoxyphenyl)(phenyl) methanone (XXIaa) in example XXIIaa by (2-amino-4,5-diethoxyphenyl)(phenyl)methanone (XXIag), and ethyl glycinate hydrochloride by methyl phenylanalilate hydrochloride, and proceeding in the same manner, the abovenamed product is obtained. Yield: 19%. M: 10–112° C. ¹H-NMR (CDCl₃, 200 MHz): d 1.38 (t, 3H, CH₃), 1.55 (t, 3H, CH₃), 3.61–3.66 (m, 2H, CH₂), 3.82–3.98 (m, 3H, CH+OCH₂), 4.18 (q, 2H, OCH₂), 6.64 (s, 1H Ar), 6,75 (s, 1H Ar), 7.25–7.57 (m, 10H Ar), 8.65 (s, 1H exchangeable, —NH).

5-(3-bromophenyl)-7,8-dimethoxy-1,3-dihydro-2H-1,4-benzodiazepin-2-one, XXIIak.

By replacing (2-amino-4,5-dimethoxyphenyl)(phenyl) methanone (XXIaa) in example XXIIaa by (2-amino-4,5-dimethoxyphenyl)(3-bromophenyl) methanone (XXIai) and proceeding in the same manner, the abovenamed product is obtained. Yield: 72%. M: 256–258° C. ¹H-NMR (DMSO, 300 MHz): d 3.61 (s, 3H, OCH₃), 3.82 (s, 3H, OCH₃), 4.10 (s, 2H, CH₂), 6.69 (s, 1H Ar), 6.83 (s, 1H Ar), 7.37–7.45 (m, 2H Ar), 7.67–7.73 (m, 2H Ar), 10.34 (s, 1H exchangeable, —NH).

5-(2-bromophenyl)-7,8-dimethoxy-1,3-dihydro-2H-1,4-benzodiazepin-2-one, XXIIal.

By replacing (2-amino-4,5-dimethoxyphenyl)(phenyl) methanone (XXIaa) in example XXIIaa by (2-amino-4,5-dimethoxyphenyl)(2-bromophenyl) methanone (XXIaj) and proceeding in the same manner, the abovenamed product is obtained. Yield: 27%. M: 280–281° C. ¹H-NMR (DMSO, 300 MHz): d 3.49 (s, 3H, OCH₃), 3.81 (s, 3H, OCH₃), 4.12 (s, 2H, CH₂), 6.33 (s, 1H Ar), 6.80 (s, 1H Ar), 7.36–7.42 (m, 1H Ar), 7.49–7.51 (m, 2H Ar), 7.63–7.65 (m, 1H Ar), 10.43 (s, 1H exchangeable, —NH).

8-ethoxy-7-methoxy-5-phenyl-1,3-dihydro-2H-1,4-benzodiazepin-2-one, XXIIam.

By replacing (2-amino-4,5-dimethoxyphenyl)(phenyl) methanone (XXIaa) in example XXIIaa by (2-amino-4-ethoxy-5-methoxyphenyl)(phenyl) methanone (XXIak) and proceeding in the same manner, the abovenamed product is obtained. Yield: 60%. ¹H-NMR (CDCl₃, 300 MHz): d 1.54 (t, 3H, CH₃), 3.73 (s, 3H, OCH₃), 4.17 (q, 2H, OCH₂), 4.33 (s, 2H, CH₂), 6.58 (s, 1H Ar), 6.73 (s, 1H Ar), 7.40–7.47 (m, 3H Ar), 7.58–7.61 (m, 3H Ar), 8.47 (s, 1H exchangeable, —NH).

8-methoxy-5-phenyl-1,3-dihydro-2H-1,4-benzodiazepin-2-one, XXIIan.

By replacing (2-amino-4,5-dimethoxyphenyl)(phenyl) methanone (XXIaa) in example XXIIaa by (2-amino-4-methoxyphenyl)(phenyl)methanone (XXIal) and proceeding in the same manner, the abovenamed product is obtained. Yield: 48%. M: 174–176° C. ¹H-NMR (CDCl₃, 200 MHz): d 3.87 (s, 3H, OCH₃), 4.32 (s, 2H, CH₂), 6.63–6.72 (m, 2H Ar), 7.20–7.56 (m, 6H Ar), 9.33 (s, 1H exchangeable, —NH).

7-methoxy-5-phenyl-1,3-dihydro-2H-1,4-benzodiazepin-2-one, XXIIao.

By replacing (2-amino-4,5-dimethoxyphenyl)(phenyl) methanone (XXIaa) in example XXIIaa by (2-amino-5-methoxyphenyl)(phenyl)methanone (XXIam) and proceeding in the same manner, the abovenamed product is obtained. Yield: 32%. M: 220–222° C. ¹H-NMR (CDCl₃, 200 MHz): d 3.72 (s, 3H, OCH₃), 4.32 (s, 2H, CH₂), 6.78 (m, 1H Ar), 7.01 (m, 2H Ar), 7.33–7.48 (m, 3H Ar), 7.56–7.60 (m, 2H Ar), 8.86 (s, 1H exchangeable, —NH).

3-benzyl-7,8-dimethoxy-5-phenyl-1,3-dihydro-2H-1,4-benzodiazepin-2-one, XXIIap.

By replacing ethyl glycinate hydrochloride in example XXIIaa by ethyl phenylalalinate hydrochloride and proceeding in the same manner, the abovenamed product is obtained. Yield: 55%. M: 216–218° C. $^1$H-NMR (DMSO, 200 MHz): d 3.37–3.49 (m, 2H, CH$_2$), 3.58–3.71 (m, 4H, 1CH+OCH$_3$), 3.84 (s, 3H, OCH$_3$), 6.65 (s, 1H Ar), 6.82 (s, 1H Ar), 7.22–7.48 (m, 10H Ar), 10.40 (s,1H, NH).

7,8-dimethoxy-3-methyl-5-phenyl-1,3-dihydro-2H-1,4-benzodiazepin-2-one, XXIIaq.

By replacing ethyl glycinate hydrochloride in example XXIIaa by ethyl alalinate hydrochloride and proceeding in the same manner, the abovenamed product is obtained. Yield: 50%. M: 247–248° C. $^1$H-NMR (DMSO, 200 MHz): d 1.52–1.55 (m, 3H, CH$_3$), 3.62–3.65 (m, 4H, 1CH+OCH$_3$), 3.85 (s, 3H, OCH$_3$), 6.70 (s, 1H Ar), 6.82 (s, 1H Ar), 7.43–7.56 (m, 10H Ar), 10.30 (s,1H, NH). Mass: (M+H)$^+$=311.12.

7,8-dimethoxy-3-(1H-imidazol-4-ylmethyl)-5-phenyl-1,3-dihydro-2H-1,4-benzodiazepin-2-one, XXIIar.

By replacing ethyl glycinate hydrochloride in example XXIIaa by ethyl histidinate dihydrochloride and proceeding in the same manner, the abovenamed product is obtained. Yield: 5%. M: 195° C., degradation. $^1$H-NMR (DMSO, 200 MHz): d 3.30–3.35 (m, 2H, CH$_2$), 3.62 (s, 3H, OCH$_3$), 3.70–3.76 (m, 1H, CH), 3.85 (s, 3H, OCH$_3$), 6.70 (s, 1H Ar), 6.82 (s, 1H Ar), 6.90 (s, 1H Imidazole), 7.47–7.53 (m, 5H Ar), 7.70 (s, 1H Imidazole), 10.37 (s, 1H, NH), 12.40 (broad s, 1H, NH). Mass: (M+H)$^+$=377.15.

7,8-dimethoxy-3-(1H-indol-3-ylmethyl)-5-phenyl-1,3-dihydro-2H-1,4-benzodiazepin-2-one, XXIIas.

By replacing ethyl glycinate hydrochloride in example XXIIaa by ethyl tryptophanate dihydrochloride and proceeding in the same manner, the abovenamed product is obtained. Yield: 10%. M: 180–185° C. $^1$H-NMR (DMSO, 200 MHz): d 3.44–3.57 (m, 5H, 1CH$_2$+OCH$_3$), 3.83 (s, 3H, OCH$_3$), 4.35–4.41 (m, 1H, CH), 6.64 (s, 1H Ar), 6.80 (s, 1H Ar), 6.97–7.07 (m, 2H Ar), 7.21–7.63 (m, 7H Ar), 10.37 (s, 1H, NH), 10.83 (s, 1H, NH Indole). Mass: (M+H)$^+$=426.19.

7,8-dimethoxy-3-(2-methylthioethyl)-5-phenyl-1,3-dihydro-2H-1,4-benzodiazepin-2-one, XXIIat.

By replacing ethyl glycinate hydrochloride in example XXIIaa by ethyl methionate hydrochloride and proceeding in the same manner, the abovenamed product is obtained. Yield: 15%. M: 126–128° C. $^1$H-NMR (DMSO, 300 MHz): d 2.04 (s, 3H, SCH$_3$), 2.49–2.51 (m, 2H, SCH$_2$), 2.59–2.72 (m, 2H, CH$_2$), 3.57–3.62 (m, 4H, 1CH+OCH$_3$), 3.83 (s, 3H, OCH$_3$), 6.68 (s, 1H Ar), 6.81 (s, 1H Ar), 7.42–7.54 (m, 5H Ar), 10.37 (s, 1H, NH). Mass: (M+H)$^+$=371.12.

(S)-3-benzyl-7,8-dimethoxy-5-phenyl-1,3-dihydro-2H-1,4-benzodiazepin-2-one, XXIIau.

By replacing ethyl glycinate hydrochloride in example XXIIaa by ethyl L-phenylalalinate hydrochloride and proceeding in the same manner, the abovenamed product is obtained. Yield: 50%. $^1$H-NMR (DMSO, 200 MHz): d 3.28–3.45 (m, 2H, CH$_2$), 3.55–3.68 (m, 4H, 1CH+OCH$_3$), 3.80 (s, 3H, OCH$_3$), 6.61 (s, 1H Ar), 6.78 (s, 1H Ar), 7.15–7.43 (m, 10H Ar), 10.34 (s, 1H, NH). Mass: (M+H)$^+$=387.14.

(7,8-dimethoxy-5-phenyl-2-oxo-2,3-dihydro-1H-1,4-benzodiazepin-3-yl)benzyl(S)-butylcarbamate, XXIIav.

By replacing ethyl glycinate hydrochloride in example XXIIaa by 377 lysine Z hydrochloride and proceeding in the same manner, the abovenamed product is obtained. Yield: 20%. M: 95–98° C. $^1$H-NMR (DMSO, 300 MHz): d 1.26–1.44 (m, 4H, 2CH$_2$), 1.95–1.97 (m, 2H, CH$_2$), 2.95–3.03 (m, 2H, CH$_2$), 3.31–3.35 (m, H, CH), 3.55 (s, 3H, OCH$_3$), 3.81 (s, 3H, OCH$_3$), 4.95 (s, 2H, CH$_2$), 6.62 (s, 1H Ar), 6.77 (s, 1H Ar), 7.20–7.29 (m, 6H, 1NH+5H Ar), 7.39–7.47 (m, 5H Ar), 10.29 (s, 1H, NH). Mass: (M+H)$^+$=502.25.

(S)-3-(4-aminobutyl)-7,8-dimethoxy-5-phenyl-1,3-dihydro-2H-1,4-benzodiazepin-2-one, XXIIaw.

Stir a mixture of 60 mg (0.12 mmol) of (7,8-dimethoxy-5-phenyl-2-oxo-2,3-dihydro-1H-1,4-benzodiazepin-3-yl) benzyl(S)-butylcarbamate (XXIIav), 6 mg of Pd/C 10% by weight in 10 ml of MeOH under an H$_2$ atmosphere at room temperature and pressure for 24 hours. Filter the suspension on celite, rinse three times with 10 ml of MeOH. Evaporate to dryness and purify by silica chromatography (AcOEt then AcOEt 5/CH$_2$Cl$_2$ 4/EtOH 1). Yield: 68%. $^1$H-NMR (DMSO, 200 MHz): d 1.55–1.63 (m, 4H, 2CH$_2$), 1.98–2.09 (m, 2H, CH$_2$), 2.75–2.81 (m, 2H, CH$_2$), 3.60 (s, 3H, OCH$_3$), 3.69–3.74 (m, H, CH), 3.84 (s, 3H, OCH$_3$), 6.67 (s, 1H Ar), 6.82 (s, 1H Ar), 7.41–7.53 (m, 5H Ar), 8.26 (broad s, 2H, NH$_2$), 10.37 (s, 1H, NH). Mass: (M+H)$^+$=368.21.

(S)-N-[4-(7,8-dimethoxy-2-oxo-5-phenyl-2,3-dihydro-1H-1,4-benzodiazepin-3-yl)butyl]acetamide, XXIIax.

To a solution of 20 mg (0.054 mmol) of (S)-3-(4-aminobutyl)-7,8-dimethoxy-5-phenyl-1,3-dihydro-2H-1,4-benzodiazepin-2-one (XXIIaw), add dropwise 11 mg (0.135 mmol) of pyridine in 2 ml of CH$_2$Cl$_2$, 6.5 mg (0.065 mmol) of acetic anhydride. Stir for 24 hours. Evaporate to dryness and purify by silica chromatography (AcOEt then AcOEt 5/CH$_2$Cl$_2$ 4/EtOH 1). Yield: 98%. M: 82–84° C. $^1$H-NMR (CDCl$_3$, 300 MHz): d 1.45–1.66 (m, 4H, 2CH$_2$), 1.97 (s, 3H, COCH$_3$), 2.22–2.27 (m, 2H, CH$_2$), 3.25–3.35 (m, 2H, CH$_2$), 3.53–3.57 (m, H, CH), 3.75 (s, 3H, OCH$_3$), 3.96 (s, 3H, OCH$_3$), 5.76 (broad s, 1H, ACNH), 6.57 (s, 1H Ar), 6.74 (s, 1H Ar), 7.39–7.58 (m, 5H Ar),), 8.07 (s, 1H, NH). Mass: (M+H)$^+$=410.21.

N-[4-(7,8-dimethoxy-2-oxo-5-phenyl-2,3-dihydro-1H-1,4-benzodiazepin-3-yl)butyl]guanidinium (S)-bis trifluoroacetate, XXIIay.

To a solution of 14 mg (0.04 mmol) of 1H-pyrazole-1-[N,N'-bis(ter-butoxycarbohyl)carboxamide] in 1 ml of anhydrous CH$_3$CN, add 20 mg (0.054 mmol) of (S)-3-(4-aminobutyl)-7,8-dimethoxy-5-phenyl-1,3-dihydro-2H-1,4-benzodiazepin-2-one (XXIIaw). Stir for 12 hours. Evaporate to dryness and purify by silica chromatography (AcOEt 1/hexane 4). Add 2 ml of TFA at 0° C. and stir at room temperature for 3 hours. Evaporate the TFA, take up in AcOEt, remove the supernatant, triturate in Et$_2$O, dry. Yield: 30%. Mass: (M+H)$^+$=410.15.

7,8-dimethoxy-3,5-diphenyl-1,3-dihydro-2H-1,4-benzodiazepin-2-one, XXIIaz.

By replacing ethyl glycinate hydrochloride in example XXIIaa by ethyl phenylglycinate hydrochloride and proceeding in the same manner, the abovenamed product is obtained. Yield: 55%. M: 202–204° C. $^1$H-NMR (CDCl$_3$, 200 MHz): d 3.62–3.78 (m, 4H, CH+OCH$_3$), 3.93 (s, 3H, OCH$_3$), 6.61 (s, 1H Ar), 6.66 (s, 1H Ar), 7.24–7.50 (m, 10H Ar), 9.14 (s, 1H, NH).

3,5-diphenyl-8-ethoxy-7-methoxy-1,3-dihydro-2H-1,4-benzodiazepin-2-one, XXIIba.

By replacing (2-amino-4,5-dimethoxyphenyl)(phenyl) methanone (XXIaa) in example XXIIaa by (2-amino-4-ethoxy-5-methoxyphenyl)(phenyl)methanone XXIak, and ethyl glycinate hydrochloride by ethyl phenylglycinate hydrochloride, and proceeding in the same manner, the abovenamed product is obtained. Yield: 55%. M: 168–169° C. $^1$H-NMR (DMSO, 200 MHz): d 1.38–1.42 (m, 3H, CH$_3$), 3.65 (s, 3H, OCH$_3$), 3.98–4.18 (m, 2H, CH$_2$), 4.76 (s, 1H, CH), 6.78 (s, 1H Ar), 6.88 (s, 1H Ar), 7.38–7.58 (m, 10H Ar), 10.49 (s, 1H, NH).

3-benzyl-8-ethoxy-7-methoxy-5-phenyl-1,3-dihydro-2H-1,4-benzodiazepin-2-one, XXIIbb.

By replacing (2-amino-4,5-dimethoxyphenyl)(phenyl)methanone (XXIaa) in example XXIIaa by (2-amino-4-ethoxy-5-methoxyphenyl)(phenyl)methanone (XXIak), and ethyl glycinate hydrochloride by ethyl phenylalalinate hydrochloride, and proceeding in the same manner, the abovenamed product is obtained. Yield: 55%. M: 190–193° C. $^1$H-NMR (DMSO, 200 MHz): d 1.33–1.39 (m, 3H, CH$_3$), 3.36–3.64 (m, 3H, CH+CH$_2$Bn), 3.73 (s, 3H, OCH$_3$), 3.95–4.10 (m, 2H, CH$_2$), 6.59 (s, 1H Ar), 6.77 (s, 1H Ar), 7.21–7.44 (m, 10H Ar), 10.36 (s, 1H, NH).

5-phenyl-7-ethoxy-8-methoxy-1,3-dihydro-2H-1,4-benzodiazepin-2-one, XXIIbc.

By replacing (2-amino-4,5-dimethoxyphenyl)(phenyl)methanone (XXIaa) in example XXIIaa by (2-amino-5-ethoxy-4-methoxyphenyl)(phenyl)methanone (XXIao) and proceeding in the same manner, the abovenamed product is obtained. Yield: 45%. M: C. $^1$H-NMR (CDCl$_3$, 200 MHz): d 1.36–1.44 (m, 3H, CH$_3$), 3.88–4.00 (m, 5H, OCH$_2$+OCH$_3$), 4.30–4.42 (m, 2H, CH$_2$), 6.62 (s, 1HAr), 6.73 (s, 1H Ar), 7.44–7.58 (m, 10H Ar), 8.88 (s, 1H, NH).

4.3. Synthesis of compounds represented by formula II
The following compounds were synthesized:
5-(4-bromophenyl)-7,8-dimethoxy-1-methyl-11,3-dihydro-2H-1,4-benzodiazepin-2-one, IIba.
3-benzyl-8-ethoxy-1-ethyl-7-methoxy-5-phenyl-1,3-dihydro-2H-1,4-benzodiazepin-2-one, IIbb.
1-benzyl-7,8-dimethoxy-5-phenyl-1,3-dihydro-2H-1,4-benzodiazepin-2-one, IIbc.
1-ethyl-7,8-dimethoxy-5-phenyl-1,3-dihydro-2H-1,4-benzodiazepin-2-one, IIbd.
7,8-dimethoxy-5-phenyl-1-propyl-1,3-dihydro-2H-1,4-benzodiazepin-2-one, IIbe.
7,8-diethoxy-1-methyl-5-phenyl-1,3-dihydro-2H-1,4-benzodiazepin-2-one, IIbf.
7,8-diethoxy-1-ethyl-5-phenyl-1,3-dihydro-2H-1,4-benzodiazepin-2-one, IIbg.
7,8-dimethoxy-1-ethyl-3-(2-nitrobenzyl)-5-phenyl-1,3-dihydro-2H-1,4-benzodiazepin-2-one, IIbh.
ethyl (7,8-diethoxy-2-oxo-5-phenyl-2,3-dihydro-1H-1,4-benzodiazepin-1-yl)acetate, IIbi.
1-benzyl-7,8-diethoxy-5-phenyl-1,3-dihydro-2H-1,4-benzodiazepin-2-one, IIbj.
1-ethyl-7,8-dihydroxy-5-phenyl-1,3-dihydro-2H-1,4-benzodiazepin-2-one, IIbk.
5-(4-bromophenyl)-1-ethyl-7,8-dimethoxy-1,3-dihydro-2H-1,4-benzodiazepin-2-one, IIbl.
5-(3-bromophenyl)-1-ethyl-7,8-dimethoxy-1,3-dihydro-2H-1,4-benzodiazepin-2-one, IIbm.
5-{4-[3-(benzyloxy)prop-1-ynyl]phenyl}-1-ethyl-7,8-dimethoxy-1,3-dihydro-2H-1,4-benzodiazepin-2-one, IIbn.
tert-butyl 3-[4-(1-ethyl-7,8-dimethoxy-2-oxo-2,3-dihydro-1H-1,4-benzodiazepin-5-yl)phenyl]prop-2-ynylcarbamate, IIbo.
5-(1,1'-biphenyl-4-yl)-1-ethyl-7,8-dimethoxy-1,3-dihydro-2H-1,4-benzodiazepin-2-one, IIbp.
3-(4-chlorobenzyl)-1-ethyl-7,8-dimethoxy-5-phenyl-1,3-dihydro-2H-1,4-benzodiazepin-2-one, IIbq.
1-ethyl-7,8-dimethoxy-5-[4-(phenylethynyl)phenyl]-1,3-dihydro-2H-1,4-benzodiazepin-2-one, IIbr.
3-allyl-1-ethyl-7,8-dimethoxy-5-phenyl-1,3-dihydro-2H-1,4-benzodiazepin-2-one, IIbs.
1-ethyl-7,8-dimethoxy-5-phenyl-3-prop-2-ynyl-1,3-dihydro-2H-1,4-benzodiazepin-2-one, IIbt.
1-ethyl-7,8-dimethoxy-5-[4-(2-phenylethyl)phenyl]-1,3-dihydro-2H-1,4-benzodiazepin-2-one, IIbu.
ethyl (1-ethyl-7,8-dimethoxy-2-oxo-5-phenyl-2,3-dihydro-1H-1,4-benzodiazepin-3-yl)acetate, IIbv.
1-ethyl-7,8-dimethoxy-5-[3-(phenylethynyl)phenyl]-1,3-dihydro-2H-1,4-benzodiazepin-2-one, IIbw.
3-(3,5-dibromobenzyl)-7,8-dimethoxy-1-ethyl-5-phenyl-1,3-dihydro-2H-1,4-benzodiazepin-2-one, IIbx.
7,8-dimethoxy-3-(diphenylhydroxymethyl)-1-ethyl-5-phenyl-1,3-dihydro-2H-1,4-benzodiazepin-2-one, IIby.
7,8-dimethoxy-1-ethyl-3-(E-3-phenylpropen-2yl)-5-phenyl-1,3-dihydro-2H-1,4-benzodiazepin-2-one, IIbz.
7,8-dimethoxy-1-ethyl-3-(2-aminobenzyl)-5-phenyl-1,3-dihydro-2H-1,4-benzodiazepin-2-one, IIca.
(1-ethyl-7,8-dimethoxy-2-oxo-5-phenyl-2,3-dihydro-1H-1,4-benzodiazepin-3-yl)acetonitrile, IIcb.
3-(2-bromobenzyl)-1-ethyl-7,8-dimethoxy-5-phenyl-1,3-dihydro-2H-1,4-benzodiazepin-2-one, IIcc.
3-(4-bromobenzyl)-1-ethyl-7,8-dimethoxy-5-phenyl-1,3-dihydro-2H-1,4-benzodiazepin-2-one, IIcd.
3-(2-cyanobenzyl)-7,8-dimethoxy-1-ethyl-5-phenyl-1,3-dihydro-2H-1,4-benzodiazepin-2-one, IIce.
N-[2-(7,8-dimethoxy-2-oxo-5-phenyl-2,3-dihydro-1H-1,4-benzodiazepin-3-yl)benzyl]acetamide, IIcf.
3-(2-aminomethylbenzyl)-7,8-dimethoxy-1-ethyl-5-phenyl-1,3-dihydro-2H-1,4-benzodiazepin-2-one, IIcg.
3-[(3-bromophenyl)(hydroxy)methyl]-1-ethyl-7,8-dimethoxy-5-phenyl-1,3-dihydro-2H-1,4-benzodiazepin-2-one, IIch.
[(7,8-dimethoxy-1-ethyl-2-oxo-2,3-dihydro-1H-1,4-benzodiazepin-3-yl)benz-2-yl]carboxamide, IIci.
3-(3-bromobenzyl)-1-ethyl-7,8-dimethoxy-5-phenyl-1,3-dihydro-2H-1,4-benzodiazepin-2-one, IIcj.
3-(1,1'-biphenyl-4-ylmethyl)-1-ethyl-7,8-dimethoxy-5-phenyl-1,3-dihydro-2H-1,4-benzodiazepin-2-one, IIck.
3-(1-benzyl-4-hydroxypiperidin-4-yl)-1-ethyl-7,8-dimethoxy-5-phenyl-1,3-dihydro-2H-1,4-benzodiazepin-2-one, IIcl.
N-[2-(7,8-dimethoxy-2-oxo-5-phenyl-2,3-dihydro-1H-1,4-benzodiazepin-3-yl)benzyl]methylacetamide, IIcm.
3-(4-chlorobenzyl)-1-ethyl-7,8-dimethoxy-5-phenyl-1,3-dihydro-2H-1,4-benzodiazepin-2-one, IIcn.
3-(2,4-dichlorobenzyl)-7,8-dimethoxy-1-ethyl-5-phenyl-1,3-dihydro-2H-1,4-benzodiazepin-2-one, IIco.
3-[(1-ethyl-7,8-dimethoxy-2-oxo-5-phenyl-2,3-dihydro-1H-1,4-benzodiazepin-3-yl)methyl]benzonitrile, IIcp.
3-benzyl-1-ethyl-7,8-dimethoxy-5-phenyl-1,3-dihydro-2H-1,4-benzodiazepin-2-one, IIcq.
1-ethyl-7,8-dimethoxy-3-(2-methoxybenzyl)-5-phenyl-1,3-dihydro-2H-1,4-benzodiazepin-2-one, IIcr.
3-[(1-ethyl-7,8-dimethoxy-2-oxo-5-phenyl-2,3-dihydro-1H-1,4-benzodiazepin-3-yl)methyl]benzamide, IIcs.
3-[3-(aminomethyl)benzyl]-1-ethyl-7,8-dimethoxy-5-phenyl-1,3-dihydro-2H-1,4-benzodiazepin-2-one, IIct.
3-(1,1'-biphenyl-3-ylmethyl)-1-ethyl-7,8-dimethoxy-5-phenyl-1,3-dihydro-2H-1,4-benzodiazepin-2-one, IIcu.
3-benzyl-7,8-diethoxy-1-ethyl-5-phenyl-1,3-dihydro-2H-1,4-benzodiazepin-2-one, IIcv.
2-(1-ethyl-7,8-dimethoxy-2-oxo-5-phenyl-2,3-dihydro-1H-1,4-benzodiazepin-3-yl)acetamide, IIcw.
7,8-dimethoxy-1-(2-hydroxyethyl)-5-phenyl-1,3-dihydro-2H-1,4-benzodiazepin-2-one, IIcx.
3-(2-chlorobenzyl)-1-ethyl-7,8-dimethoxy-5-phenyl-1,3-dihydro-2H-1,4-benzodiazepin-2-one, IIcy.
1-ethyl-7,8-dimethoxy-3-(2-methylbenzyl)-5-phenyl-1,3-dihydro-2H-1,4-benzodiazepin-2-one, IIcz.

8-ethoxy-7-methoxy-1-methyl-5-phenyl-1,3-dihydro-2H-1,4-benzodiazepin-2-one, IIda.

1-ethyl-7,8-dimethoxy-5-phenyl-3-[3-(trifluoromethyl)benzyl]-1,3-dihydro-2H-1,4-benzodiazepin-2-one, IIdb.

1-ethyl-7,8-dimethoxy-3-(3-methoxybenzyl)-5-phenyl-1,3-dihydro-2H-1,4-benzodiazepin-2-one, IIdc.

1-ethyl-7,8-dimethoxy-3-(4-methylbenzyl)-5-phenyl-1,3-dihydro-2H-1,4-benzodiazepin-2-one, IIdd.

3-[1,2-bis(4-bromophenyl)ethyl]-1-ethyl-7,8-dimethoxy-5-phenyl-1,3-dihydro-2H-1,4-benzodiazepin-2-one, IIde.

3-[(8-ethoxy-7-methoxy-1-methyl-2-oxo-5-phenyl-2,3-dihydro-1H-1,4-benzodiazepin-3-yl)methyl]benzonitrile, IIdf.

2-[(8-ethoxy-7-methoxy-1-methyl-2-oxo-5-phenyl-2,3-dihydro-1H-1,4-benzodiazepin-3-yl)methyl]benzonitrile, IIdg.

3-[(8-ethoxy-7-methoxy-1-methyl-2-oxo-5-phenyl-2,3-dihydro-1H-1,4-benzodiazepin-3-yl)methyl]benzamide, IIdh.

3-(2,5-dichlorobenzyl)-7,8-dimethoxy-1-ethyl-5-phenyl-1,3-dihydro-2H-1,4-benzodiazepin-2-one, IIdi.

(S)-3-benzyl-7,8-dimethoxy-1-methyl-5-phenyl-1,3-dihydro-2H-1,4-benzodiazepin-2-one, IIdj.

3,5-diphenyl-8-ethoxy-1-ethyl-7-methoxy-1,3-dihydro-2H-1,4-benzodiazepin-2-one, IIdk.

7-methoxy-1-methyl-5-phenyl-1,3-dihydro-2H-1,4-benzodiazepin-2-one, IIdl.

8-methoxy-1-methyl-5-phenyl-1,3-dihydro-2H-1,4-benzodiazepin-2-one, IIdm.

5-(4-bromophenyl)-7,8-dimethoxy-1-methyl-1,3-dihydro-2H-1,4-benzodiazepin-2-one, IIba.

To a solution of 100 mg (0.267 mmol) of 5-(4-bromophenyl)-7,8-dimethoxy-1,3-dihydro-2H-1,4-benzodiazepin-2-one (XXIIaf) in 2 ml of anhydrous DMF, add under an inert atmosphere 48 mg (0.35 mmol) of $K_2CO_3$. After 30 minutes at room temperature, add dropwise 25 μl (0.4 mmol) of MeI. Allow to stand at room temperature for 12 hours. Add 30 ml of water. Extract three times with 30 ml of $EtO_2$. Dry the organic fractions on $Na_2SO_4$. Purify by chromatography (AcOEt 1/hexane 1). Recrystallize in $EtO_2$. One obtains 78 mg of the abovenamed product as a white powder. Yield: 73%. $^1$H-NMR (CDCl$_3$, 200 MHz): d 3.40 (s, 3H, NCH$_3$), 3.75 (s, 3H, OCH$_3$), 3.99 (s, 3H, OCH$_3$), 4.29 (AB system, ? d=1.014, J$_{AB}$=10.7, 2H, CH$_2$), 6.65 (s, 1H Ar), 6.78 (s, 1H Ar), 7.54 (s, 4H Ar).

3-benzyl-8-ethoxy-1-ethyl-7-methoxy-5-phenyl-1,3-dihydro-2H-1,4-benzodiazepin-2-one, IIbb.

By replacing 5-(4-bromophenyl)-7,8-dimethoxy-1,3-dihydro-2H-1,4-benzodiazepin-2-one (XXIIaf) in example IIba by 3-benzyl-8-ethoxy-7-methoxy-5-phenyl-1,3-dihydro-2H-1,4-benzodiazepin-2-one (XXIIbb), and methyl iodide by ethyl iodide, and proceeding in the same manner, the abovenamed product is obtained. Yield: 65%. F: 228–230° C. $^1$H-NMR (CDCl$_3$, 300 MHz): d 1.03–1.08 (m, 3H, NCH$_2$CH$_3$), 1.50–1.54 (m, 3H, OCH$_2$CH$_3$), 3.59–3.65 (m, 3H, 1HNCH$_2$+CH$_2$Bn), 3.70 (s, 3H, OCH$_3$), 3.77–3.83 (m, 1H, 1CH), 4.12–4.18 (m, 2H, OCH$_2$), 4.30–4.41 (m, 1H, 1HNCH$_2$), 6.62 (s, 1H Ar), 6.79 (s, 1H Ar), 7.22–7.59 (m, 10H Ar).

1-benzyl-7,8-dimethoxy-5-phenyl-1,3-dihydro-2H-1,4-benzodiazepin-2-one, IIbc.

By replacing 5-(4-bromophenyl)-7,8-dimethoxy-1,3-dihydro-2H-1,4-benzodiazepin-2-one (XXIIaf) in example IIba by 7,8-dimethoxy-5-phenyl-1,3-dihydro-2H-1,4-benzodiazepin-2-one (XXIIaa), and MeI by benzyl bromide, and proceeding in the same manner, the abovenamed product is obtained. Yield: 64%. M: 148–149° C. $^1$H-NMR (CDCl$_3$, 200 MHz): d 3.67 (s, 3H, OCH$_3$), 3.83 (s, 3H, OCH$_3$), 4.38 (AB system, ? d=0.96, J$_{AB}$=10.0 2H, CH$_2$), 5.15 (AB system, ? d=0.70, J$_{AB}$=15.4, 2H, —NCH$_2$), 6.56 (s, 1H Ar), 6.81 (s, 1H Ar), 7.07–7.46 (m, 10H Ar).

1-ethyl-7,8-dimethoxy-5-phenyl-1,3-dihydro-2H-1,4-benzodiazepin-2-one, IIbd.

By replacing 5-(4-bromophenyl)-7,8-dimethoxy-1,3-dihydro-2H-1,4-benzodiazepin-2-one (XXIIaf) in example IIba by 7,8-dimethoxy-5-phenyl-1,3-dihydro-2H-1,4-benzodiazepin-2-one (XXIIaa), and MeI by ethyl iodide, and proceeding in the same manner, the abovenamed product is obtained. Yield: 62%. M: 86–88° C. $^1$H-NMR (CDCl$_3$, 200 MHz): d 1.15 (t, 3H, CH$_3$), 3.80 (s, 3H, OCH$_3$), 4.01 (s, 3H, OCH$_3$), 4.03 (AB system, ? d=0.61, J$_{AB}$=13.9, 2H, —NCH$_2$), 4.30 (AB system, ? d=1.00, J$_{AB}$=9.98, 2H, CH$_2$), 6.71 (s, 1H Ar), 6.88 (s, 1H Ar), 7.40–7.69 (m, 5H Ar).

7,8-dimethoxy-5-phenyl-1-propyl-1,3-dihydro-2H-1,4-benzodiazepin-2-one, IIbe.

By replacing 5-(4-bromophenyl)-7,8-dimethoxy-1,3-dihydro-2H-1,4-benzodiazepin-2-one (XXIIaf) in example IIba by 7,8-dimethoxy-5-phenyl-1,3-dihydro-2H-1,4-benzodiazepin-2-one (XXIIaa), and MeI by (n)-propyl bromide, and proceeding in the same manner, the abovenamed product is obtained. Yield: 33%. M: 136–138° C. $^1$H-NMR (CDCl$_3$, 200 MHz): d 0.75 (t, 3H, CH$_3$), 1.48 (m, 2H, CH$_2$), 3.75 (s, 3H, OCH$_3$), 3.97 (s, 3H, OCH$_3$), 3.94 (AB system, ? d=0.87 J$_{AB}$=13.4, 2H, —NCH$_2$), 4.28 (AB system, ? d=0.97, J$_{AB}$=10.26, 2H, CH$_2$), 6.68 (s, 1H Ar), 6.84 (s, 1H Ar), 7.40–7.66 (m, 5H Ar).

7,8-diethoxy-1-methyl-5-phenyl-1,3-dihydro-2H-1,4-benzodiazepin-2-one, IIbf.

By replacing 5-(4-bromophenyl)-7,8-dimethoxy-1,3-dihydro-2H-1,4-benzodiazepin-2-one (XXIIaf) in example IIba by 7,8-diethoxy-5-phenyl-1,3-dihydro-2H-1,4-benzodiazepin-2-one (XXIIag) and proceeding in the same manner, the abovenamed product is obtained. Yield: 28%. M: 116–118° C. $^1$H-NMR (CDCl$_3$, 200 MHz): d 1.40 (t, 3H, CH$_3$), 1.56 (t, 3H, CH$_3$), 3.42 (s, 3H, NCH$_3$), 3.97 (q, 2H, OCH$_2$), 4.21 (q, 2H, OCH$_2$), 4.33 (AB system, ? d=0.98 J$_{AB}$=10.5, 2H, CH$_2$), 6.74 (s, 1H Ar), 6.81 (s, 1H Ar), 7.42–7.70 (m, 5H Ar).

7,8-diethoxy-1-ethyl-5-phenyl-1,3-dihydro-2H-1,4-benzodiazepin-2-one, IIbg.

By replacing 5-(4-bromophenyl)-7,8-dimethoxy-1,3-dihydro-2H-1,4-benzodiazepin-2-one (XXIIaf) in example IIba by 7,8-diethoxy-5-phenyl-1,3-dihydro-2H-1,4-benzodiazepin-2-one (XXIIag), and MeI by ethyl iodide, and proceeding in the same manner, the abovenamed product is obtained. Yield: 59%. M: 99–102° C. $^1$H-NMR (CDCl$_3$, 300 MHz): d 1.11 (t, 3H, CH$_3$), 1.36 (t, 3H, CH$_3$), 1.53 (t, 3H, CH$_3$), 3.93 (q, 2H, OCH$_2$), 3.97 (AB system, ?d=0.67, J$_{AB}$=14.0, 2H, —NCH$_2$), 4.17 (q, 2H, OCH$_2$), 4.28 (AB system, ?d=0.96 J$_{AB}$=10.0, 2H, CH$_2$), 6.68 (s, 1H Ar), 6.84 (s, 1H Ar), 7.38–7.64 (m, 5H Ar).

7,8-dimethoxy-1-ethyl-3-(2-nitrobenzyl)-5-phenyl-1,3-dihydro-2H-1,4-benzodiazepin-2-one, IIbh.

To a solution of 920 μl (1.84 mmol) of 2M LDA/THF in 5 ml of anhydrous THF, add dropwise at −78° C. under an inert atmosphere a solution of 300 mg (0.92 mmol) of 1-ethyl-7,8-dimethoxy-5-phenyl-1,3-dihydro-2H-1,4-benzodiazepin-2-one (IIbd) in 2 ml of THF. Allow to equilibrate to room temperature for 30 minutes. Add dropwise at −30

C. a solution of 220 mg (1.01 mmol) of 2-nitrobenzyl bromide in 2 ml of THF. Stir at room temperature for 12 hours. Add 1 ml of H$_2$O. Evaporate the THF. Purify by silica chromatography (AcOEt 1/hexane 4, 1/1, then AcOEt). Recrystallize in EtOH/cHexane. Yield: 35%. M: 158–160° C. $^1$H-NMR (DMSO, 300 MHz): d 0.87–0.91 (m, 3H, CH$_3$), 3.61–3.99 (m, 10H, NCH+CHCH$_2$+2OCH$_3$), 4.35–4.40 (m, 1H, NCH), 6.60 (s, 1H Ar), 6.82 (s, 1 H Ar), 7.37–7.90 (m, 9H Ar). Mass: (M+H)$^+$=460.88.

ethyl (7,8-diethoxy-2-oxo-5-phenyl-2,3-dihydro-1H-1,4-benzodiazepin-1-yl)acetate, IIbi.

By replacing 5-(4-bromophenyl)-7,8-dimethoxy-1,3-dihydro-2H-1,4-benzodiazepin-2-one (XXIIaf) in example IIba by 7,8-diethoxy-5-phenyl-1,3-dihydro-2H-1,4-benzodiazepin-2-one (XXIIag), and MeI by ethyl bromoacetate, and proceeding in the same manner, the abovenamed product is obtained. Yield: 55%. M: 160–162° C. $^1$H-NMR (CDCl$_3$, 200 MHz): d 1.21 (t, 3H, CH$_3$), 1.36 (t, 3H, CH$_3$), 1.50 (t, 3H, CH$_3$), 3.88–4.26 (m, 7H, 3×OCH$_2$+1H CH$_2$) 4.49 (AB system, ? d=0.17, J$_{AB}$=17.4, 2H, —NCH$_2$), 4.80 (m, 1H CH$_2$), 6.71 (s, 1H Ar), 6.81 (s, 1H Ar), 7.27–7.69 (m, 5H Ar).

1-benzyl-7,8-diethoxy-5-phenyl-1,3-dihydro-2H-1,4-benzodiazepin-2-one, IIbj.

By replacing 5-(4-bromophenyl)-7,8-dimethoxy-1,3-dihydro-2H-1,4-benzodiazepin-2-one (XXIIaf) in example IIba by 7,8-diethoxy-5-phenyl-1,3-dihydro-2H-1,4-benzodiazepin-2-one (XXIIag), and MeI by benzyl bromide, and proceeding in the same manner, the abovenamed product is obtained. Yield: 32%. M: 158–160° C. $^1$H-NMR (CDCl$_3$, 300 MHz): d 1.33 (t, 3H, CH$_3$), 1.40 (t, 3H, CH$_3$), 3.84–3.95 (m, 3H, OCH$_2$+1H CH$_2$) 4.04 (q, 2H OCH$_2$), 4.87 (m, 1H CH$_2$), 5.15 (AB system, ? d=0.74, J$_{AB}$=15.4, 2H, —NCH$_2$), 6.58 (s, 1H Ar), 6.81 (s, 1H Ar), 7.07–7.46 (m, 10H Ar).

1-ethyl-7,8-dihydroxy-5-phenyl-1,3-dihydro-2H-1,4-benzodiazepin-2-one, IIbk.

Add dropwise at 0° C. under an inert atmosphere, 0.68 ml of a 1 M solution of BBr$_3$ (0.68 mmol) in CH$_2$Cl$_2$ on 200 mg (0.62 mmol) of 7,8-diethoxy-1-ethyl-5-phenyl-1,3-dihydro-2H-1,4-benzodiazepin-2-one (IIbg) in 5 ml of dichloromethane. Stir at room temperature for 12 hours. Quench at 0° C. with methanol. Evaporate to dryness. Triturate again and evaporate. Purify by chromatography (AcOEt). Recrystallize in EtO$_2$/pentane. One obtains 30 mg of the abovenamed product as a yellow powder. Yield: 16%. M: 230–231° C. $^1$H-NMR (DMSO, 200 MHz): d 0.96 (t, 3H, CH$_3$), 3.80 (AB system, ? d=0.54, J$_{AB}$=13.7, 2H, —NCH$_2$), 4.05 (AB system, ? d=0.72, J$_{AB}$=10.0, 2H, CH$_2$), 6.52 (s, 1H Ar), 6.91 (s, 1H Ar), 7.42–7.55 (m, 5H Ar), 9–10.5 (hump, 2H, 2×—OH).

5-(4-bromophenyl)-1-ethyl-7,8-dimethoxy-1,3-dihydro-2H-1,4-benzodiazepin-2-one, IIbl.

By replacing MeI in example IIba by iodoethane and proceeding in the same manner, the abovenamed product is obtained. Yield: 76%. M: 93–95° C. $^1$H-NMR (CDCl$_3$, 200 MHz): d 1.10 (s, 3H, CH$_3$), 3.78 (s, 3H, OCH$_3$), 3.97 (s, 3H, OCH$_3$), 3.98 (AB system, ? d=0.54, J$_{AB}$=14.2, 2H, —NCH$_2$), 4.25 (AB system, ? d=0.98, J$_{AB}$=10.3, 2H, CH$_2$), 6.63 (s, 1H Ar), 6.84 (s, 1H Ar), 7.53 (s, 4H Ar).

5-(3-bromophenyl)-1-ethyl-7,8-dimethoxy-1,3-dihydro-2H-1,4-benzodiazepin-2-one, IIbm.

By replacing 5-(4-bromophenyl)-7,8-dimethoxy-1,3-dihydro-2H-1,4-benzodiazepin-2-one (XXIIaf) in example IIba by 5-(3-bromophenyl)-7,8-dimethoxy-2H-1,4-benzodiazepin-2-one (XXIIak), and MeI by ethyl iodide, and proceeding in the same manner, the abovenamed product is obtained. Yield: 17%. M: 122–126° C. $^1$H-NMR (CDCl$_3$, 300 MHz): d 1.14 (s, 3H, CH$_3$), 3.79–3.85 (m, 4H, 1H CH$_2$+OCH$_3$), 3.99 (AB system, ? d=0.62, J$_{AB}$=13.9, 2H, —NCH$_2$), 4.04 (s, 3H, OCH$_3$), 4.78 (m, 1H, CH$_2$), 6.65 (s, 1H Ar), 6.86 (s, 1H Ar), 7.26–7.31 (m, 2H Ar), 7.52–7.62 (m, 2H Ar), 7.86 (s, 1H Ar).

5-{4-[3-(benzyloxy)prop-1-ynyl]phenyl}-1-ethyl-7,8-dimethoxy-1,3-dihydro-2H-1,4-benzodiazepin-2-one, IIbn.

Stir for 12 hours under an inert atmosphere at 50° C., a mixture of 100 mg (0.27 mmol) of 5-(4-bromophenyl)-1-ethyl-7,8-dimethoxy-1,3-dihydro-2H-1,4-benzodiazepin-2-one (IIbl), 194 mg (1.3 mmol) of [(prop-2-ynyloxy)methyl]benzene, 9.0 mg of CuI, 5.2 mg of PdCl$_2$, 18.0 mg of PPh$_3$, 0.5 ml of TEA, 2 ml of CH$_3$CN. Evaporate to dryness and purify by silica chromatography (AcOEt 1/hexane 1). Recrystallize in EtO$_2$/pentane. Yield: 37%. M: 64–66° C. $^1$H-NMR (CDCl$_3$, 300 MHz): d 1.12 (s, 3H, CH$_3$), 3.72–3.83 (m, 4H, 1H CH$_2$+OCH$_3$), 4.00 (AB system, ? d=0.63, J$_{AB}$=13.5, 2H, —NCH$_2$), 4.03 (s, 3H, OCH$_3$), 4.43 (s, 2H, OCH$_2$), 4.69 (m, 2H, =C—CH$_2$), 4.77 (m, 1H, OCH$_2$), 6.65 (s, 1H Ar), 6.86 (s, 1H Ar), 7.27–7.63 (m, 9H Ar).

tert-butyl 3-[4-(1-ethyl-7,8-dimethoxy-2-oxo-2,3-dihydro-1H-1,4-benzodiazepin-5-yl)phenyl]prop-2-ynylcarbamate, IIbo.

By replacing [(prop-2-ynyloxy)methyl]benzene in example IIbn by tert-butyl-prop-2-ynylcarbamate and proceeding in the same manner, the abovenamed product is obtained. Yield: 47%. M: 95–97° C. $^1$H-NMR (CDCl$_3$, 300 MHz): d 1.10 (s, 3H, CH$_3$), 1.47 (m, 9H, CH$_3$), 3.72–3.78 (m, 4H, 1H CH$_2$+OCH$_3$), 3.96 (s, 3H, OCH$_3$), 3.7 (AB system, ? d=0.64, J$_{AB}$=13.5, 2H, —NCH$_2$), 4.16 (m, 2H, =C—CH$_2$), 4.81 (m, 1H, OCH$_2$), 4.88 (s, 1H, —NH), 6.62 (s, 1H Ar), 6.84 (s, 1H Ar), 7.42–7.59 (m, 4H Ar).

5-(1,1'-biphenyl-4-yl)-1-ethyl-7,8-dimethoxy-1,3-dihydro-2H-1,4-benzodiazepin-2-one, IIbp.

Heat at 90° C. for 12 hours under an inert atmosphere a mixture of 100 mg (0.27 mmol) of 5-(4-bromophenyl)-1-ethyl-7,8-dimethoxy-1,3-dihydro-2H-1,4-benzodiazepin-2-one (IIbl), 35 mg (0.30 mmol) of benzene boronic acid, 215 μl of 2M Na$_2$CO$_3$, 25 mg (0.020 mmol) of tetrakis(triphenylphosphine)Pd(0) and 250 μl of EtOH in 5 ml of degassed toluene. Allow to cool to room temperature. Evaporate to dryness. Purify by chromatography (AcOEt). Recrystallize in Et$_2$O. One obtains 62 mg of the abovenamed product in the form of colorless crystals. Yield: 52%. M: 149–150° C. $^1$H-NMR (CDCl$_3$, 200 MHz): d 1.13 (s, 3H, CH$_3$), 3.78 (s, 3H, OCH$_3$), 3.95 (AB system, ? d=0.57, J$_{AB}$=13.7, 2H, —NCH$_2$), 3.98 (s, 3H, OCH$_3$), 4.29 (AB system, ? d=0.99 J$_{AB}$=10.0, 2H, CH$_2$), 6.75 (s, 1H Ar), 6.86 (s, 1H Ar), 7.37–7.75 (m, 9H Ar).

3-(4-chlorobenzyl)-1-ethyl-7,8-dimethoxy-5-phenyl-1,3-dihydro-2H-1,4-benzodiazepin-2-one, IIbq.

By replacing 2-nitrobenzyl bromide in example IIbh by 4-chlorobenzyl bromide and proceeding in the same manner, the abovenamed product is obtained. Yield: 22%. M: 78–81° C. $^1$H-NMR (CDCl$_3$, 300 MHz): d 1.07 (s, 3H, CH$_3$), 3.54 (s, 1H, CH), 3.56 (s, 2H, CH$_2$), 3.72 (s, 3H, OCH$_3$), 3.95 (s, 3H, OCH$_3$), 3.99 (AB system, ? d=0.75, J$_{AB}$=13.7, 2H, —NCH$_2$), 6.64 (s, 1H Ar), 6.81 (s, 1H Ar), 7.23–7.32 (m, 4H Ar), 7.39–7.45 (m, 3H Ar), 7.55–7.58 (m, 2H Ar).

1-ethyl-7,8-dimethoxy-5-[4-(phenylethynyl)phenyl]-1,3-dihydro-2H-1,4-benzodiazepin-2-one, IIbr.

By replacing [(prop-2-ynyloxy)methyl]benzene in example IIbn by phenylacetylene and proceeding in the same manner, the abovenamed product is obtained. Yield: 80%. M: 166–168° C. $^1$H-NMR (CDCl$_3$, 200 MHz): d 1.16 (s, 3H, CH$_3$), 3.79 (s, 3H, OCH$_3$), 4.01 (s, 3H, OCH$_3$), 4.02 (AB system, ? d=0.65, $J_{AB}$=13.9, 2H, —NCH$_2$), 4.32 (AB system, ?d=0.98, $J_{AB}$=10.5, 2H, CH$_2$), 6.70 (s, 1H Ar), 6.88 (s, 1H Ar), 7.37–7.70 (m, 9H Ar).

3-alyl-1-ethyl-7,8-dimethoxy-5-phenyl-1,3-dihydro-2H-1,4-benzodiazepin-2-one, IIbs.

By replacing 2-nitrobenzyl bromide in example IIbh by allyl bromide and proceeding in the same manner, the abovenamed product is obtained. Yield: 46%. M: 176–179° C. $^1$H-NMR (CDCl$_3$, 200 MHz): d 1.11 (s, 3H, CH$_3$), 3.02–3.09 (m, 2H=CH$_2$), 3.60–3.73 (m, 2H, CH+1H-NCH$_2$), 3.79 (s, 3H, OCH$_3$), 4.01 (s, 3H, OCH$_3$), 4.32–4.50 (m, 1H, —NCH$_2$), 5.08–5.25 (m, 2H, =C—CH$_2$), 5.94–6.14 (m, 1H, =CH), 6.73 (s, 1H Ar), 6.87 (s, 1H Ar), 7.42–7.49 (m, 3H Ar), 7.64–7.69 (m, 2H Ar).

1-ethyl-7,8-dimethoxy-5-phenyl-3-prop-2-ynyl-1,3-dihydro-2H-1,4-benzodiazepin-2-one, IIbt.

By replacing 2-nitrobenzyl bromide in example IIbh by propargyl bromide and proceeding in the same manner, the abovenamed product is obtained. Yield: 22%. M: 161–163° C. $^1$H-NMR (CDCl$_3$, 200 MHz): d 1.07 (s, 3H, CH$_3$), 3.11–3.18 (m, 2H, —CH$_2$C=), 3.59–3.86 (m, 6H, OCH$_3$+=CH+1H NCH$_2$+CH), 3.97 (s, 3H, OCH$_3$), 4.35–4.42 (m, 1H, NCH$_2$), 6.71 (s, 1H Ar), 6.85 (s, 1H Ar), 7.39–7.42 (m, 3H Ar), 7.62–7.66 (m, 2H Ar).

1-ethyl-7,8-dimethoxy-5-[4-(2-phenylethyl)phenyl]-1,3-dihydro-2H-1,4-benzodiazepin-2-one, IIbu.

Leave the following under hydrogen pressure (Patm) for 48 hours: 80 mg of 5-(1,1'-biphenyl-4-yl)-1-ethyl-7,8-dimethoxy-1,3-dihydro-2H-1,4-benzodiazepin-2-one (IIbp), 16 mg of 10% palladium on charcoal (20% by weight of product to reduce), in 30 ml of methanol and 1 ml of CH$_2$Cl$_2$. Filter on celite, rinse several times with methanol. Evaporate to dryness. Purify by silica chromatography (AcOEt 1/hexane 1). Recrystallize in ether. One obtains 28 mg of the abovenamed product in the form of a white powder. Yield: 35%. M: 148–150° C. $^1$H-NMR (CDCl$_3$, 200 MHz): d 1.27 (t, 3H, —CH$_3$), 3.00 (s, 4H, 2×—CH$_2$). 3,37–3,40 (m, 2H, CH$_2$), 3.45–3.65 (m, 4H, —OCH$_3$+1H NCH$_2$), 3.92 (s, 3H, OCH$_3$), 4.21–4.48 (m, 1H, NCH$_2$), 6.22 (d, 1H Ar), 6.77 (d, 1H Ar), 7.19–7.39 (m, 9H Ar).

ethyl (1-ethyl-7,8-dimethoxy-2-oxo-5-phenyl-2,3-dihydro-1H-1,4-benzo diazepin-3-yl)acetate, IIbv.

By replacing 2-nitrobenzyl bromide in example IIbh by ethyl acetate bromide and proceeding in the same manner, the abovenamed product is obtained. Yield: 11%. M: 116–118° C. $^1$H-NMR (CDCl$_3$, 200 MHz): d 1.10 (s, 3H, CH$_3$), 1.32 (s, 3H, CH$_3$), 3.13–3.25 (m, 1H, —OCH$_2$), 3.43–3.56 (m, 1H, —OCH$_2$), 3.63–3.78 (m, 4H, OCH$_3$+1H NCH$_2$), 4.00 (s, 3H, OCH$_3$), 4.16–4.44 (m, 4H, CH+CH$_2$+1H NCH$_2$), 6.71 (s, 1H Ar), 6.90 (s, 1H Ar), 7.30–7.65 (m, 5H Ar).

1-ethyl-7,8-dimethoxy-5-[3-(phenylethynyl)phenyl]-1,3-dihydro-2H-1,4-benzodiazepin-2-one, IIbw.

By replacing 5-(4-bromophenyl)-1-ethyl-7,8-dimethoxy-1,3-dihydro-2H-1,4-benzodiazepin-2-one (IIbl) in example IIbn by 5-(3-bromophenyl)-1-ethyl-7,8-dimethoxy-1,3-dihydro-2H-1,4-benzodiazepin-2-one (IIbm), and [(prop-2-ynyloxy)methyl]benzene by phenylacetylene, and proceeding in the same manner, the abovenamed product is obtained. Yield: 33%. M: 100–102° C. $^1$H-NMR (CDCl$_3$, 200 MHz): d 1.13 (s, 3H, CH$_3$), 3.51–3.82 (m, 5H, 1H NCH$_2$+1H CH$_2$+OCH$_3$), 3.97 (s, 3H, OCH$_3$), 4.24–4.34 (m, 1H, NCH$_2$), 4.74–4.80 (m, 1H, CH$_2$), 6.66 (s, 1H Ar), 6.84 (s, 1H Ar), 7.26–7.83 (m, 9H Ar).

3-(3,5-dibromobenzyl)-7,8-dimethoxy-1-ethyl-5-phenyl-1,3-dihydro-2H-1,4-benzodiazepin-2-one, IIbx.

By replacing 2-nitrobenzyl bromide in example IIbh by 3,5-dibromobenzyl bromide and proceeding in the same manner, the abovenamed product is obtained. Yield: 30%. M: 178–179° C. $^1$H-NMR (DMSO, 300 MHz): d 0.85–0.89 (m, 3H, CH$_3$), 3.28–3.36 (m, 2H, CHCH$_2$), 3.59 (s, 3H, OCH$_3$), 3.69–3.75 (m, 2H, NCH+CHCH$_2$), 4.20–4.27 (m, 1H, NCH), 6.60 (s, 1H Ar), 7.13 (s, 1H Ar), 7.43–7.72 (m, 8H Ar). Mass: (M+H)$^+$=573.05.

7,8-dimethoxy-3-(diphenylhydroxymethyl)-1-ethyl-5-phenyl-1,3-dihydro-2H-1,4-benzodiazepin-2-one, IIby.

By replacing 2-nitrobenzyl bromide in example IIbh by benzophenone and proceeding in the same manner, the abovenamed product is obtained. Yield: 36%. M: 228–230° C. $^1$H-NMR (CDCl$_3$, 300 MHz): d 0.98–1.03 (m, 3H, CH$_3$), 3.74 (s, 3H, OCH$_3$), 4.00 (AB system, ?d=0.71, $J_{AB}$=13.7, 2H, NCH$_2$), 4.03 (s, 3H, OCH$_3$), 4.57 (s, 1H, CHCOH), 6.41 (s, 1H, CHCOH), 6.66 (s, 1H Ar), 6.94 (s, 1H Ar), 7.27–7.51 (m, 15H Ar). Mass: (M+H)$^+$=507.3.

7,8-dimethoxy-1-ethyl-3-(E-3-phenylpropen-2yl)-5-phenyl-1,3-dihydro-2H-1,4-benzodiazepin-2-one, IIbz.

By replacing 2-nitrobenzyl bromide in example IIbh by 3-bromo-1-phenylprop-1-ene and proceeding in the same manner, the abovenamed product is obtained. Yield: 37%. M: 162–164° C. $^1$H-NMR (DMSO, 300 MHz): d 0.86–0.91 (m, 3H, CH$_3$), 2.92–3.01 (m, 2H, CH$_2$CH=), 3.62 (s, 3H, OCH$_3$), 3.88 (s, 3H, OCH$_3$) 3.98 (AB system, ? d=0.55, $J_{AB}$=13.6, 2H, NCH$_2$), 6.32–6.40 (m, 1H, CH$_2$CH=), 6.50–6.56 (m, 1H, PhCH=), 6.66 (s, 1H Ar), 7.15 (s, 1H Ar), 7.16–7.60 (m, 10H Ar). Mass: (M+H)$^+$=441.24.

7,8-dimethoxy-1-ethyl-3-(2-aminobenzyl)-5-phenyl-1,3-dihydro-2H-1,4-benzodiazepin-2-one, IIca.

Stir a mixture of 80 mg (0.17 mmol) of 7,8-dimethoxy-1-ethyl-3-(2-nitrobenzyl)-5-phenyl-1,3-dihydro-2H-1,4-benzodiazepin-2-one IIbh, 10 mg of Pd/C 10% by weight in 15 ml of MeOH under 65 psi of H$_2$ at room temperature for 2 hours. Filter the suspension on celite, rinse three times with 10 ml of MeOH. Evaporate to dryness and purify by silica chromatography (AcOEt 1/hexane 4, 1/2). Recrystallize in EtOH. Yield: 70%. M: degradation at 280° C. $^1$H-NMR (DMSO, 300 MHz): d 0.86–0.90 (m, 3H, CH$_3$), 3.21–3.31 (m, 2H, CHCH$_2$), 3.59 (s, 3H, OCH$_3$), 3.69–3.76 (m, 2H, NCH+CHCH$_2$), 3.88 (s, 3H, OCH$_3$), 4.22–4.30 (m, 1H, NCH), 6.46–6.51 (m, 1H Ar), 6.59–6.61 (m, 2H Ar), 6.85–6.88 (m, 1H Ar), 7.01–7.03 (m, 1H Ar), 7.41–7.53 (m, 5H Ar). Mass: (M+H)$^+$=430.22.

(1-ethyl-7,8-dimethoxy-2-oxo-5-phenyl-2,3-dihydro-1H-1,4-benzodiazepin-3-yl)acetonitrile, IIcb.

By replacing 2-nitrobenzyl bromide in example IIbh by acetonitrile chloride and proceeding in the same manner, the abovenamed product is obtained but the reaction is very slow. Yield: 3%. M: 97–100° C. $^1$H-NMR (CDCl$_3$, 200 MHz): d 1.13 (s, 3H, CH$_3$), 3.12–3.46 (m, 2H, —CH$_2$—CN), 3.80 (s, 3H, OCH$_3$), 4.02 (s, 3H, OCH$_3$), 4.05 (AB system, ? d=0.68, $J_{AB}$=13.9, 2H, —NCH$_2$), 6.75 (s, 1H Ar), 6.88 (s, 1H Ar), 7.45–7.50 (m, 3H Ar), 7.68–7.72 (m, 3H Ar).

3-(2-bromobenzyl)-1-ethyl-7,8-dimethoxy-5-phenyl-1,3-dihydro-2H-1,4-benzodiazepin-2-one, Icec.

By replacing 2-nitrobenzyl bromide in example IIbh by 2-bromobenzyle bromide and proceeding in the same manner, the abovenamed product is obtained. Yield: 27%. M: 102–104° C. $^1$H-NMR (CDCl$_3$, 300 MHz): d 1.06 (s, 3H, CH$_3$), 3.52–3.82 (m, 6H, OCH$_3$+1H NCH$_2$+CH+1H —CH$_2$Ph), 3.92–4.05 (m, 4H, +1H —CH$_2$Ph+OCH$_3$), 4.35–4.47 (m, 1H NCH$_2$), 6.63 (s, 1H Ar), 6.83 (s, 1H Ar), 7.05–7.11 (m, 1H Ar), 7.30–7.50 (m, 8H Ar).

3-(4-bromobenzyl)-1-ethyl-7,8-dimethoxy-5-phenyl-1,3-dihydro-2H-1,4-benzodiazepin-2-one, IIcd.

By replacing 2-nitrobenzyl bromide in example IIbh by 4-bromobenzyl bromide and proceeding in the same manner, the abovenamed product is obtained. Yield: 61%. M: 97–99° C. $^1$H-NMR (CDCl$_3$, 200 MHz): d 1.05 (s, 3H, CH$_3$), 3.50–3.54 (m, 2H, CH+1H —CH$_2$Ph), 3.56–3.77 (m, 5H, OCH$_3$+1H NCH$_2$+1H —CH$_2$Ph), 3.93 (s, 3H, OCH$_3$), 4.28–4.45 (m, 1H NCH$_2$), 6.62 (s, 1H Ar), 6.80 (s, 1H Ar), 7.12–7.25 (m, 2H Ar), 7.35–7.37 (m, 5H Ar), 7.53–7.58 (m, 2H Ar).

3-(2-cyanobenzyl)-7,8-dimethoxy-1-ethyl-5-phenyl-1,3-dihydro-2H-1,4-benzodiazepin-2-one, IIce.

By replacing 2-nitrobenzyl bromide in example IIbh by 2-cyanobenzyl bromide and proceeding in the same manner, the abovenamed product is obtained. Yield: 45%. M: 154–156° C. $^1$H-NMR (CDCl$_3$, 300 MHz): d 1.05–1.10 (m, 3H, CH$_3$), 3.59–3.97 (m, 10H, CHCH$_2$+2OCH$_3$+1HNCH$_2$), 4.34–4.41 (m, 1H, 1HNCH$_2$), 6.61 (s, 1H Ar), 6.83 (s, 1H Ar), 7.29–7.77 (m, 9H Ar). Mass: (M+H)$^+$=440.23.

N-[2-(7,8-dimethoxy-2-oxo-5-phenyl-2,3-dihydro-1H-1,4-benzodiazepin-3-yl)benzyl]acetamide, IIcf.

To a solution of 40 mg (0.09 mmol) of 7,8-dimethoxy-1-ethyl-3-(2-aminobenzyl)-5-phenyl-1,3-dihydro-2H-1,4-benzodiazepin-2-one IIca, add 18.4 mg (0.23 mmol) of pyridine in 4 ml of CH$_2$Cl$_2$, 11.5 mg (0.11 mmol) of acetic anhydride dropwise. Stir for 24 hours. Evaporate to dryness and purify by silica chromatography (AcOEt then AcOEt 5/CH$_2$Cl$_2$ 4/EtOH 1). Yield: 70%. M: 144–145° C. $^1$H-NMR (CDCl$_3$, 300 MHz): d 0.89–0.96 (m, 3H, CH$_3$), 2.01 (s, 1H, COCH$_3$), 3.36–3.45 (m, 2H, CHCH$_2$), 3.61 (s, 3H, OCH$_3$), 3.73–3.84 (m, 2H, CHCH$_2$+1HNCH$_2$), 3.91 (s, 3H, OCH$_3$), 6.60 (s, 1H Ar), 7.07–7.61 (m, 10H Ar). Mass: (M+H)$^+$=472.23.

3-(2-aminomethylbenzyl)-7,8-dimethoxy-1-ethyl-5-phenyl-1,3-dihydro-2H-1,4-benzodiazepin-2-one, IIcg.

Stir a mixture of 100 mg (0.23 mmol) of 3-(2-cyanobenzyl)-7,8-dimethoxy-1-ethyl-5-phenyl-1,3-dihydro-2H-1,4-benzodiazepin-2-one IIce, 10 mg of Raney nickel in 5 ml of MeOH under an H$_2$ atmosphere at room temperature and pressure for 12 hours. Filter the suspension on celite, rinse three times with 10 ml of MeOH. Evaporate to dryness and purify by silica chromatography (AcOEt 5/CH$_2$Cl$_2$ 4/EtOH 1, CH$_2$Cl$_2$ 4/MeOH 1). Recrystallize in EtOH. Yield: 70%. M: 280° C. with degradation. $^1$H-NMR (CDCl$_3$, 300 MHz): d 0.98–1.02 (m, 3H, CH$_3$), 3.33–3.37 (m, 1H, 1H CHCH$_2$), 3.54–3.59 (m, 5H, OCH$_3$+1H NCH$_2$CH$_3$+1H CHCH$_2$), 3.79–3.84 m, 1H, CHCH$_2$), 3.89 (s, 3H, OCH$_3$), 4.25–4.32 (m, 3H, CH$_2$NH$_2$+1H NCH$_2$CH$_3$), 6.40 (s, 1H Ar), 6.78 (s, 1H Ar), 7.02–7.63 (m, 10H Ar). Mass: (M+H)$^+$=444.22

3-[(3-bromophenyl)(hydroxy)methyl]-1-ethyl-7,8-dimethoxy-5-phenyl-1,3-dihydro-2H-1,4-benzodiazepin-2-one, IIch.

By replacing 2-nitrobenzyl bromide in example IIbh by 3-bromobenzaldehyde bromide and proceeding in the same manner, the abovenamed product is obtained. Yield: 41%. M: 85–86° C. $^1$H-NMR (DMSO, 200 MHz): d 0.90 (s, 3H, CH$_3$), 3.34–3.65 (d, 1H, CH), 3.60 (s, 3H, OCH$_3$), 3.93 (s, 3H, OCH$_3$), 4.03 (AB system, ? d=0.58, J$_{AB}$=14.4, 2H, —NCH$_2$), 5.54 (dd, 1H, —CH-Ph), 5.73 (d, 1H, —OH), 6.57 (s, 1H Ar), 7.22 (s, 1H Ar), 7.28–7.49 (m, 8H Ar), 7.66 (s, 1H Ar).

[(7,8-dimethoxy-1-ethyl-2-oxo-2,3-dihydro-1H-1,4-benzodiazepin-3-yl)benz-2-yl]carboxamide, IIci.

To a solution of 100 mg (0.23 mmol) of 3-(2-cyanobenzyl)-7,8-dimethoxy-1-ethyl-5-phenyl-1,3-dihydro-2H-1,4-benzodiazepin-2-one IIce in 2 ml of EtOH, add 80 µl of 10% (m/m) H$_2$O$_{2aq}$ and dropwise 90 vl of 0.5 M NaOHaq. Add 50 ml of H$_2$O and extract three times with ml of AcOEt; dry on MgSO$_4$, evaporate the AcOEt and purify by silica chromatography (AcOEt 1/hexane 1 then AcOEt). Recrystallize in AcOEt. Yield: 65%. M: 193–195° C. $^1$H-NMR (CDCl$_3$, 300 MHz): d 1.10–1.15 (m, 3H, CH$_3$), 3.25–3.31 (m, 1H, 1H CHCH$_2$), 3.66–3.73 (m, 4H, OCH$_3$+1H NCH$_2$CH$_3$), 3.95–4.00 (s, 4H, OCH$_3$+1H CHCH$_2$), 4.19–4.28 (m, 1H, CHCH$_2$), 4.38–4.45 (m, 1H, 1H NCH$_2$CH$_3$), 4.74 (broad s, 2H, CONH$_2$), 6.54 (s, 1H Ar), 6.88 (s, 1H Ar), 7.09–7.85 (m, 10H Ar). Mass: (M+H)$^+$=458.23.

3-(3-bromobenzyl)-1-ethyl-7,8-dimethoxy-5-phenyl-1,3-dihydro-2H-1,4-benzodiazepin-2-one, IIcj.

By replacing 2-nitrobenzyl bromide in example IIbh by 3-bromobenzyl bromide and proceeding in the same manner, the abovenamed product is obtained. Yield: 56%. M: 140–142° C. $^1$H-NMR (CDCl$_3$, 200 MHz): d 1.07 (s, 3H, CH$_3$), 3.52–3.77 (m, 7H, CH+—CH$_2$Ph+OCH$_3$+1H NCH$_2$), 3.96 (s, 3H, OCH$_3$), 4.32–4.43 (m, 1H NCH$_2$), 6.63 (s, 1H Ar), 6.82 (s, 1H Ar), 7.15–7.19 (m, 1H Ar), 7.26–7.45 (m, 5H Ar), 7.55–7.60 (m, 3H Ar).

3-(1,1'-biphenyl-4-ylmethyl)-1-ethyl-7,8-dimethoxy-5-phenyl-1,3-dihydro-2H-1,4-benzodiazepin-2-one, IIck.

By replacing 5-(4-bromophenyl)-1-ethyl-7,8-dimethoxy-1,3-dihydro-2H-1,4-benzodiazepin-2-one (IIbl) in example IIbp by 3-(4-bromobenzyl)-1-ethyl-7,8-dimethoxy-5-phenyl-1,3-dihydro-2H-1,4-benzodiazepin-2-one (IIcd) and proceeding in the same manner, the abovenamed product is obtained. Yield: 48%. $^1$H-NMR (CDCl$_3$, 300 MHz): d 1.08 (s, 3H, CH$_3$), 3.61–3.87 (m, 7H, OCH$_3$+CH+1H NCH$_2$+—CH$_2$Ph), 4.01 (s, 3H, OCH$_3$), 4.38–4.45 (m, 1H NCH$_2$), 6.66 (s, 1H Ar), 6.83 (s, 1H Ar), 7.33–7.63 (m, 14H Ar).

3-(1-benzyl-4-hydroxypiperidin-4-yl)-1-ethyl-7,8-dimethoxy-5-phenyl-1,3-dihydro-2H-1,4-benzodiazepin-2-one, IIcl.

By replacing 2-nitrobenzyl bromide in example IIbh by 1-benzyl-piperidin-4-one and proceeding in the same manner, the abovenamed product is obtained. Yield: 61%. M: 197–199° C. $^1$H-NMR (CDCl$_3$, 300 MHz): d 1.07 (s, 3H, CH$_3$), 1.65–1.92 (m, 4H, 2×CH$_2$), 2.28–2.32 (m, 1H, CH), 2.54–2.68 (m, 4H, 2×CH$_2$), 3.35 (s, 1H CH$_2$-Ph), 3.57–3.72 (m, 2H, 1H CH$_2$-Ph+1H —NCH$_2$), 3.77 (s, 3H, OCH$_3$), 3.99 (s, 3H, +OCH$_3$), 4.31–4.38 (m, 1H —NCH$_2$), 4.53 (s, 1H, —OH), 6.72 (s, 1H Ar), 7.86 (s, 1H Ar), 7.30–7.46 (m, 8H Ar), 7.66–7.68 (s, 1H Ar).

N-[2-(7,8-dimethoxy-2-oxo-5-phenyl-2,3-dihydro-1H-1,4-benzodiazepin-3-yl)benzyl]methylacetamide, Icm.

By replacing 7,8-dimethoxy-1-ethyl-3-(2-aminobenzyl)-5-phenyl-1,3-dihydro-2H-1,4-benzodiazepin-2-one (IIca) in example IIcf by 7,8-dimethoxy-1-ethyl-3-(2-aminomethylbenzyl)-5-phenyl-1,3-dihydro-2H-1,4-benzodiazepin-2-one (IIcg) and proceeding in the same manner, the abovenamed product is obtained. Yield: 55%. M: 122–124° C. $^1$H-NMR (CDCl$_3$, 200 MHz): d 1.07–1.14 (m, 3H, CH$_3$), 1.49 (s, 1H, COCH$_3$), 3.41–3.80 (m, 6H, CHCH$_2$+1HNCH$_2$+OCH$_3$), 3.89–3.98 (m, 4H, CHCH$_2$+OCH$_3$), 4.34–4.45 (m, 1HNCH$_2$), 6.60 (s, 1H Ar), 4.55–4.57 (m, 2H, CH$_2$NHAc), 6.52 (s, 6.85 (s, 1H Ar), 7.18–8.45 (m, 9H Ar), 8.45 (m, 1H, NHAc).

3-(4-chlorobenzyl)-1-ethyl-7,8-dimethoxy-5-phenyl-1,3-dihydro-2H-1,4-benzodiazepin-2-one, IIcn.

By replacing 2-nitrobenzyl bromide in example IIbh by 4-chlorobenzyl bromide and proceeding in the same manner, the abovenamed product is obtained. Yield: 52%. M: 109–111° C. $^1$H-NMR (CDCl$_3$, 200 MHz): d 1.07 (s, 3H, CH$_3$), 3.54 (d, 1H —CH$_2$Ph), 3.72–3.77 (m, 5H,1H —CH$_2$Ph+CH+OCH$_3$), 3.95 (s, 3H, OCH$_3$), 4.00 (AB system, ? d=0.73, J$_{AB}$=13.4, 2H, —NCH$_2$), 6.63 (s, 1H Ar), 6.81 (s, 1H Ar), 7.26–7.42 (m, 7H Ar), 7.55–7.58 (m, 2H Ar).

3-(2,4-dichlorobenzyl)-7,8-dimethoxy-1-ethyl-5-phenyl-1,3-dihydro-2H-1,4-benzodiazepin-2-one, IIco.

By replacing 2-nitrobenzyl bromide in example IIbh by 2,4-dichlorobenzyl bromide and proceeding in the same manner, the abovenamed product is obtained. Yield: 20%. M: 92–94° C. $^1$H-NMR (CDCl$_3$, 200 MHz): d 1.02–1.09 (m, 3H, CH$_3$), 3.60–3.72 (m, 6H, +OCH$_3$, 1HNCH$_2$), 3.82–3.89 (m, 1H, CHCH$_2$), 3.96 (s, 3H, OCH$_3$), 4.33–4.44 (m, 1H, 1HNCH$_2$), 6.62 (s, 1H Ar), 6.82 (s, 1H Ar), 7.26–7.59 (m, 9H Ar).

3-[(1-ethyl-7,8-dimethoxy-2-oxo-5-phenyl-2,3-dihydro-1H-1,4-benzodiazepin-3-yl)methyl]benzonitrile, IIcp.

By replacing 2-nitrobenzyl bromide in example IIbh by 3-bromomethyl benzonitrile and proceeding in the same manner, the abovenamed product is obtained. Yield: 33%. M: 95–97° C. $^1$H-NMR (CDCl$_3$, 200 MHz): d 1.10 (s, 3H, CH$_3$), 3.63 (d, 1H —CH$_2$Ph), 3.68–3.85 (m, 5H, 1H —CH$_2$Ph+CH+OCH$_3$), 3.99 (s, 3H, OCH$_3$), 4.01 (AB system, ? d=0.69, J$_{AB}$=14.2, 2H, —NCH$_2$), 6.67 (s, 1H Ar), 6.86 (s, 1H Ar), 7.42–7.70 (m, 9H Ar).

3-benzyl-1-ethyl-7,8-dimethoxy-5-phenyl-1,3-dihydro-2H-1,4-benzodiazepin-2-one, IIcq.

By replacing 2-nitrobenzyl bromide in example IIbh by benzyl bromide and proceeding in the same manner, the abovenamed product is obtained. Yield: 38%. M: 157–159° C. $^1$H-NMR (CDCl$_3$, 200 MHz): d 1.10 (s, 3H, CH$_3$), 3.61–3.86 (m, 7H, —CH$_2$Ph+1H —NCH$_2$+CH+OCH$_3$), 3.99 (s, 3H, OCH$_3$), 4.37–4.47 (m, 1H —NCH$_2$), 6.67 (s, 1H Ar), 6.84 (s, 1H Ar), 7.30–7.44 (m, 8H Ar), 7.60–7.64(m, 2H Ar).

1-ethyl-7,8-dimethoxy-3-(2-methoxybenzyl)-5-phenyl-1,3-dihydro-2H-1,4-benzodiazepin-2-one, Icr.

By replacing 2-nitrobenzyl bromide in example IIbh by 2-methoxybenzyl bromide and proceeding in the same manner, the abovenamed product is obtained. Yield: 24%. M: 100–102° C. $^1$H-NMR (CDCl$_3$, 200 MHz): d 1.09 (s, 3H, CH$_3$), 3.50–3.92 (m, 10H, —CH$_2$Ph+1H —NCH$_2$+CH+2× OCH$_3$),3.99 (s, 3H, OCH$_3$), 4.39–4.49 (m, 1H —NCH$_2$), 6.66 (s, 1H Ar), 6.81–6.85 (m, 2H Ar), 6.95–7.02 (m, 1H Ar), 7.19–7.30 (m, 1H Ar), 7.39–7.59 (m, 6H Ar).

3-[(1-ethyl-7,8-dimethoxy-2-oxo-5-phenyl-2,3-dihydro-1H-1,4-benzodiazepin-3-yl)methyl]benzamide, IIcs.

To a solution of 40 mg (0.91 mmol) of 3-[(1-ethyl-7,8-dimethoxy-2-oxo-5-phenyl-2,3-dihydro-1H-1,4-benzodiazepin-3-yl)methyl]benzonitrile (IIcp) in 1 ml of ethanol, add under an inert atmosphere 27 μl (0.27 mmol) of 30% (m/m) H$_2$O$_2$ in water, 36 μl (0.018 mmol) of 0.5 M NaOH in water. Stir under reflux for 12 hours. Evaporate to dryness. Take up in a 25 ml of a water-ice mixture. Filter the solid, wash twice with 20 ml of water and once with 5 ml of ether. One obtains 24 mg of the abovenamed product as a white powder. Yield: 59%. M: 111–113° C. $^1$H-NMR (CDCl$_3$, 200 MHz): d 1.10 (s, 3H, CH$_3$), 3.50–3.75 (m, 6H, 1H —CH$_2$Ph+1H —NCH$_2$+CH+OCH$_3$), 3.98–4.11 (m, 4H, 1H —CH$_2$Ph+ OCH$_3$), 4.38–4.49 (m, 1H —NCH$_2$), 5.91 (m, 1H exchangeable CO—NH$_2$), 6.26 (m, 1H exchangeable CO—NH$_2$), 6.66 (s, 1H Ar), 6.85 (s, 1H Ar), 7.30–7.86 (m, 9H Ar).

3-[3-(aminomethyl)benzyl]-1-ethyl-7,8-dimethoxy-5-phenyl-1,3-dihydro-2H-1,4-benzodiazepin-2-one, IIct.

Leave under hydrogen pressure (Patm) for 12 hours, 40 mg of 3-[(1-ethyl-7,8-dimethoxy-2-oxo-5-phenyl-2,3-dihydro-1H-1,4-benzodiazepin-3-yl)methyl]benzonitrile (IIcp), 0.4 ml of 30% ammonia, 4 ml of methanol, 1 spatula tip of Raney nickel. Filter on celite, rinse several times with methanol. Evaporate to dryness. Take up in 50 ml of dichloromethane, wash three times with 50 ml of 0.5 M NH$_3$ and twice with water. Dry the organic phase on Na$_2$SO$_4$. Evaporate to dryness. Recrystallize in ether. Filter. One obtains 40 mg of the abovenamed product in the form of a white powder. Yield: 55%. M: 122–125° C. $^1$H-NMR (CDCl$_3$, 200 MHz): d 1.10 (s, 3H, CH$_3$), 1.30 (m, 2H exchangeable —NH$_2$), 3.50–3.89 (m, 8H, 1H —CH$_2$Ph+1H —NCH$_2$+CH+CH$_2$—NH$_2$+OCH$_3$), 3.98–4.11 (m, 4H, 1H —CH$_2$Ph+OCH$_3$), 4.37–4.47 (m, 1H —NCH$_2$), 6.67 (s, 1H Ar), 6.84 (s,1H Ar), 7.20–7.64 (m, 9H Ar).

3-(1,1'-biphenyl-3-ylmethyl)—ethyl-7,8-dimethoxy-5-phenyl-1,3-dihydro-2H-1,4-benzodiazepin-2-one, IIcu.

By replacing 5-(4-bromophenyl)-1-ethyl-7,8-dimethoxy-1,3-dihydro-2H-1,4-benzodiazepin-2-one (IIbl) in example IIbp by 3-(3-bromobenzyl)-1-ethyl-7,8-dimethoxy-5-phenyl-1,3-dihydro-2H-1,4-benzodiazepin-2-one (IIcj) and proceeding in the same manner, the abovenamed product is obtained. Yield: 33% M: 139–141° C. $^1$H-NMR (CDCl$_3$, 200 MHz): d 1.12 (s, 3H, CH$_3$), 3.50–3.89 (m, 7H, OCH$_3$+ CH+1H NCH$_2$+—CH$_2$Ph), 3.99 (s, 3H, OCH$_3$), 4.38–4.48 (m, 1H NCH$_2$), 6.67 (s, 1H Ar), 6.85 (s, 1H Ar), 7.43–7.68 (m, 14H Ar).

3-benzyl-7,8-diethoxy-1-ethyl-5-phenyl-1,3-dihydro-2H-1,4-benzodiazepin-2-one, IIcv.

By replacing 5-(4-bromophenyl)-7,8-dimethoxy-1,3-dihydro-2H-1,4-benzodiazepin-2-one (XXIIaf) in example IIba by 3-benzyl-7,8-diethoxy-5-phenyl-1,3-dihydro-2H-1,4-benzodiazepin-2-one (XXIIaj), and MeI by ethyl iodide, and proceeding in the same manner, the abovenamed product is obtained. Yield: 36%. M: 128–130° C. $^1$H-NMR (CDCl$_3$, 200 MHz): d 1.10 (t, 3H, CH$_3$), 1.40 (t, 3H, CH$_3$), 1.55 (t, 3H, CH$_3$), 3.66 (m, 3H, CH$_2$Ph+CH), 3.94 (q, 2H, —OCH$_2$), 4.15 (AB system, ? d=0.52, J$_{AB}$=13.2, 2H, —NCH$_2$), 4.19 (q, 2H, —OCH$_2$), 6.67 (s, 1H Ar), 6.85 (s, 1H Ar), 7.33–7.63 (m, 10H Ar).

2-(1-ethyl-7,8-dimethoxy-oxo-5-phenyl-2,3-dihydro-1H-1,4-benzodiazepin-3-yl)acetamide, IIcw.

Stir at 0° C. under an inert atmosphere for 48 hours, 70 mg (0.17 mmol) of ethyl (1-ethyl-7,8-dimethoxy-2-oxo-5-phenyl-2,3-dihydro-1H-1,4-benzodiazepin-3-yl)acetate (IIbv)

and 1.5 ml of methanol at 35% molar saturation with NH$_3$. Evaporate to dryness. Purify by silica chromatography (dichloromethane 9/methanol 1). Recrystallize in ether. One obtains 12 mg of the abovenamed product as a white powder. Yield: 17%. M: 105–107° C. $^1$H-NMR (CDCl$_3$, 300 MHz): d 1.10 (t, 3H, CH$_3$), 3.02–3.09 (m, 1H —CH$_2$), 3.22–3.29 (m, 1H —CH$_2$), 3.75 (s, 1H, OCH$_3$), 3.98 (s, 1H, OCH$_3$), 4.01 (AB system, ? d=0.67, J$_{AB}$=13.9, 2H, —NCH$_2$), 4.13 (t, 1H, CH), 5.52 (s, 1H exchangeable NH$_2$), 6.43 (s, 1H exchangeable NH$_2$), 6.67 (s, 1H Ar), 6.85 (s, 1H Ar), 7.38–7.47 (m, 3H Ar), 7.59–7.62 (m, 2H Ar).

7,8-dimethoxy-1-(2-hydroxyethyl)-5-phenyl-1,3-dihydro-2H-1,4-benzodiazepin-2-one, IIcx.

To a solution of 150 mg (0.50 mmol) of 7,8-dimethoxy-5-phenyl-1,3-dihydro-1,4-benzodiazepin-2-one XXIIaa in 5 ml of DMF, add at 0° C. under an inert atmosphere 21 mg (0.52 mmol) of 60% NaH in oil. Stir at room temperature for 1 hour. Add at 0° C., 53 mg (0.60 mmol) of ethylene carbonate. Stir at room temperature overnight. Add 50 ml of H$_2$O and extract three times with 50 ml of AcOEt; dry on MgSO$_4$, evaporate the AcOEt and purify by silica chromatography (AcOEt 3/hexane 1, then AcOEt). Recrystallize in CHCl$_3$/cHexane. Yield: 40%. M: 128–130° C. $^1$H-NMR (DMSO, 300 MHz): d 3.36–3.52 (m, 2H, HOCH$_2$), 3.60 (s, 3H, OCH$_3$), 3.70–3.86 (m, 5H, NCH$_2$+OCH$_3$), 4.11 (AB system, ? d=0.77, J$_{AB}$=9.96, 2H, CH$_2$), 4.77 (m, 1H, OH), 6.60 (s, 1H Ar), 7.39 (s, 1H Ar), 7.42–7.58 (m, 4H Ar). Mass: (M+H)$^+$=341.16.

3-(2-chlorobenzyl)-1-ethyl-7,8-dimethoxy-5-phenyl-1,3-dihydro-2H-1,4-benzodiazepin-2-one, IIcy.

By replacing 2-nitrobenzyl bromide in example IIbh by 2-chlorobenzyl bromide and proceeding in the same manner, the abovenamed product is obtained. Yield: 60%. M: 78–81° C. $^1$H-NMR (CDCl$_3$, 300 MHz): d 1.09 (s, 3H, CH$_3$), 3.50–3.96 (m, 6H, 1H —CH$_2$Ph+1H —NCH$_2$+CH+OCH$_3$), 3.90–3.98 (m, 3H, 1H —CH$_2$Ph+OCH$_3$), 4.38–4.44 (m, 1H —NCH$_2$), 6.63 (1H Ar), 6.83 (s, 1H Ar), 7.16–7.65 (m, 9H Ar).

1-ethyl-7,8-dimethoxy-3-(2-methylbenzyl)-5-phenyl-1,3-dihydro-2H-1,4-benzodiazepin-2-one, IIcz.

By replacing 2-nitrobenzyl bromide in example IIbh by 2-methylbenzyl bromide and proceeding in the same manner, the abovenamed product is obtained. Yield: 55%. M: 73–75° C. $^1$H-NMR (CDCl$_3$, 300 MHz): d 1.08 (s, 3H, CH$_3$), 2.40 (s, 3H, CH$_3$), 3.62–3.73 (m, 6H, 1H —CH$_2$Ph+ 1H —NCH$_2$+CH+OCH$_3$), 3.83–3.86 (m, 1H —CH$_2$Ph), 3.97 (s, 3H, CH$_3$), 4.38–4.45 (m, 1H —NCH$_2$), 6.64 (s, 1H Ar), 6.84 (s, 1H Ar), 7.14 (m, 3H Ar), 7.34–7.44 (m, 4H Ar),7.56–7.58 (m, 2H Ar).

8-ethoxy-7-methoxy-1-methyl-5-phenyl-1,3-dihydro-2H-1,4-benzodiazepin-2-one, IIda.

By replacing in the example 7,8-dimethoxy-5-phenyl-1,3-dihydro-1,4-benzodiazepin-2-one (XXIIaa) by 8-ethoxy-7-methoxy-5-phenyl-1,3-dihydro-2H-1,4-benzodiazepin-2-one (XXIIam), and ethylene carbonate by iodomethane, and proceeding in the same manner, the abovenamed product is obtained. Yield: 69%. M: 138–140° C. $^1$H-NMR (CDCl$_3$, 200 MHz): d 1.54 (t, 3H, CH$_3$), 3.38 (s, 3H, NCH$_3$), 3.74 (s, 3H, OCH$_3$), 4.18 (q, 2H, —OCH$_2$), 4.29 (AB system, ? d=0.98, J$_{AB}$=10.5, 2H, —CH$_2$), 6.70 (s, 1H Ar), 6.77 (s, 1H Ar), 7.39–7.43 (m, 3H Ar), 7.63–7.68 (m, 3H Ar).

1-ethyl-7,8-dimethoxy-5-phenyl-3-[3-(trifluoromethyl)benzyl]-1,3-dihydro-2H-1,4-benzodiazepin-2-one, Idb.

By replacing 2-nitrobenzyl bromide in example IIbh by 3-trifluoromethylbenzyl bromide and proceeding in the same manner, the abovenamed product is obtained. Yield: 49%. M: 151–153° C. $^1$H-NMR (CDCl$_3$, 300 MHz): d 1.09 (s, 3H, CH$_3$), 3.55–3.77 (m, 7H, —CH$_2$Ph+1H —NCH$_2$+CH+OCH$_3$), 3.96 (s, 3H, OCH$_3$), 4.32–4.44 (m, 1H —NCH$_2$), 6.63 (s, 1H Ar), 6.83 (s, 1H Ar), 7.37–7.48 (m, 5H Ar),7.55–7.58 (m, 3H Ar), 7.70 (s, 1H Ar).

1-ethyl-7,8-dimethoxy-3-(3-methoxybenzyl)-5-phenyl-1,3-dihydro-2H-1,4-benzodiazepin-2-one, IIdc.

By replacing 2-nitrobenzyl bromide in example IIbh by 3-methoxybenzyl bromide and proceeding in the same manner, the abovenamed product is obtained. Yield: 45%. M: 155–157° C. $^1$H-NMR (CDCl$_3$, 300 MHz): d 1.08 (s, 3H, CH$_3$), 3.56–3.60 (m, 2H, 1H —CH$_2$Ph+CH), 3.72 (s, 3H, NCH$_3$), 3.77–3.80 (m, 1H CH$_2$Ph), 3.95 (s, 3H, OCH$_3$), 4.00 (AB system, ? d=0.75, J$_{AB}$=14.0, 2H, —NCH$_2$), 6.64 (s, 1H Ar), 6.74–6.77 (m, 1H Ar), 6.82 (s, 1H Ar), 6.95–6.98 (m, 2H Ar), 7.20 (t, 1H Ar), 7.37–7.45 (m, 3H Ar), 7.59–7.62 (m, 2H Ar).

1-ethyl-7,8-dimethoxy-3-(4-methylbenzyl)-5-phenyl-1,3-dihydro-2H-1,4-benzodiazepin-2-one, IIdd.

By replacing 2-nitrobenzyl bromide in example IIbh by 4-methylbenzyl bromide and proceeding in the same manner, the abovenamed product is obtained. Yield: 24%. M: 107–108° C. $^1$H-NMR (CDCl$_3$, 300 MHz): d 1.07 (s, 3H, CH$_3$), 2.32 (s, 3H, CH$_3$), 3.54–3.58 (m, 2H, 1H —CH$_2$Ph+ CH), 3.72 (s, 3H, OCH$_3$), 3.75–3.80 (m, 1H CH$_2$Ph), 3.95 (s, 3H, OCH$_3$), 3.96 (AB system, ? d=0.68, J$_{AB}$=14.3, 2H, —NCH$_2$), 6.64 (s, 11H Ar), 6.81 (s, 1H Ar), 7.20 (AB system, ? d=0.17, J$_{AB}$=7.8, 2H, —NCH$_2$), 7.37–7.45 (m, 3H Ar), 7.59–7.62 (m, 2H Ar).

3-[1,2-bis(4-bromophenyl)ethyl]-1-ethyl-7,8-dimethoxy-5-phenyl-1,3-dihydro-2H-1,4-benzodiazepin-2-one, IIde.

This product is obtained at the same time as 3-(4-bromobenzyl)-1-ethyl-7,8-dimethoxy-5-phenyl-1,3-dihydro-2H-1,4-benzodiazepin-2-one (IIcd). Isolate by chromatography. Yield: 20%. M: 195–198° C. $^1$H-NMR (DMSO, 300 MHz): d 0.89 (s, 3H, CH$_3$), 2.82 (m, 1H, CH-Ph), 3.16 (m, 1H, CH), 3.61 (s, 3H, OCH$_3$), 3.91 (AB system, ? d=0.15, J$_{AB}$=10.2, 2H, —CH$_2$Ph), 3.93 (s, 3H, OCH$_3$), 3.96 (AB system, ? d=0.68, J$_{AB}$=13.5, 2H, —NCH$_2$), 6.61 (s, 1 H Ar), 7.05 (AB system, ? d=0.16, J$_{AB}$=7.9, 4H Ar), 7.23–7.39 (m, 8H Ar), 7.57 (s, 3H Ar).

3-[(8-ethoxy-7-methoxy-1-methyl-2-oxo-5-phenyl-2,3-dihydro-1H-1,4-benzodiazepin-3-yl)methyl]benzonitrile, IIdf.

By replacing 1-ethyl-7,8-dimethoxy-5-phenyl-1,3-dihydro-2H-1,4-benzodiazepin-2-one (IIbd) in example IIbh by 8-ethoxy-7-methoxy-1-methyl-5-phenyl-1,3-dihydro-2H-1,4-benzodiazepin-2-one (IIIda), and 2-nitrobenzyl bromide by 3-bromomethyl-benzonitrile, and proceeding in the same manner, the abovenamed product is obtained. Yield: 35%. M: 148–150° C. $^1$H-NMR (CDCl$_3$, 200 MHz): d 1.53 (s, 3H, CH$_3$), 3.40 (s, 3H, NCH$_3$), 3.58–3.62 (m, 2H, 1H —CH$_2$Ph+ CH), 3.72 (s, 3H, OCH$_3$), 3.75–3.80 (m, 1H CH$_2$Ph), 4.17 (q, 2H, CH$_2$), 6.66 (s, 1H Ar), 6.76 (s, 1H Ar), 7.35–7.67 (m, 9H Ar).

2-[(8-ethoxy-7-methoxy-1-methyl-2-oxo-5-phenyl-2,3-dihydro-1H-1,4-benzodiazepin-3-yl)methyl]benzonitrile, IIdg.

By replacing 1-ethyl-7,8-dimethoxy-5-phenyl-1,3-dihydro-2H-1,4-benzodiazepin-2-one (IIbd) in example IIbh by 8-ethoxy-7-methoxy-1-methyl-5-phenyl-1,3-dihydro-2H-1,4-benzodiazepin-2-one (IIda), and 2-nitrobenzyl bromide by 2-bromomethyl-benzonitrile, and proceeding in the same manner, the abovenamed product is obtained. Yield: 58%. M: 238–240° C. $^1$H-NMR (CDCl$_3$, 200 MHz): d 1.53 (s, 3H, CH$_3$), 3.40 (s, 3H, NCH$_3$), 3.71 (s, 3H, OCH$_3$), 3.78–3.90 (m, 3H, —CH$_2$Ph+CH), 4.17 (q, 2H, CH$_2$), 6.64 (s, 1H Ar), 6.76 (s, 1H Ar), 7.31–7.78 (m, 9H Ar).

3-[(8-ethoxy-7-methoxy-1-methyl-2-oxo-5-phenyl-2,3-dihydro-1H-1,4-benzodiazepin-3-yl)methyl]benzamide, IIdh.

By replacing 3-[(1-ethyl-7,8-dimethoxy-2-oxo-5-phenyl-2,3-dihydro-1H-1,4-benzodiazepin-3-yl)methyl]benzonitrile (IIcp) in example IIcs by 3-[(8-ethoxy-7-methoxy-1-methyl-2-oxo-5-phenyl-2,3-dihydro-1H-1,4-benzodiazepin-3-yl)methyl]benzonitrile (IIdf) and proceeding in the same manner, the abovenamed product is obtained. Yield: 86%. M: 199–201° C. $^1$H-NMR (CDCl$_3$, 300 MHz): d 1.52 (s, 3H, CH$_3$), 3.39 (s, 3H, NCH$_3$), 3.66–3.79 (m, 3H, —CH$_2$Ph+CH+OCH$_3$), 4.17 (q, 2H, CH$_2$), 5.84 (m, 1H exchangeable —NH$_2$), 6.24 (m, 1H exchangeable —NH$_2$), 6.64 (s, 1H Ar), 6.74 (s, 1H Ar), 7.26–7.83 (m, 9H Ar).

3-(2,5-dichlorobenzyl)-7,8-dimethoxy-1-ethyl-5-phenyl-1,3-dihydro-2H-1,4-benzodiazepin-2-one, IIdi.

By replacing 2-nitrobenzyl bromide in example IIbh by 2,5-dichlorobenzyl bromide and proceeding in the same manner, the abovenamed product is obtained. Yield: 22%. M: 94–95° C. $^1$H-NMR (CDCl$_3$, 300 MHz): d 1.03–1.10 (m, 3H, CH$_3$), 3.64–3.82 (m, 7H, CHCH$_2$, OCH$_3$, 1HNCH$_2$), 3.96 (s, 3H, OCH$_3$), 4.35–4.45 (m, 1H, 1HNCH$_2$), 6.62 (s, 1H Ar), 6.83 (s, 1H Ar), 7.16–7.64 (m, 9H Ar).

(S)-3-benzyl-7,8-dimethoxy-1-methyl-5-phenyl-1,3-dihydro-2H-1,4-benzodiazepin-2-one, IIdj.

By replacing 5-(4-bromophenyl)-7,8-dimethoxy-1,3-dihydro-2H-1,4-benzodiazepin-2-one (XXIIaf) in example IIba by (S) 3-benzyl-7,8-dimethoxy-5-phenyl-1,3-dihydro-1,4-benzodiazepin-2-one (XXIIau) and proceeding in the same manner, the abovenamed product is obtained. Yield: 55%. M: 104–106° C. $^1$H-NMR (DMSO, 200 MHz): d 3.45 (s, 3H, NCH$_3$), 3.61–3.65 (m, 2H, CH$_2$), 3.75–3.84 (m, 4H, 1CH+OCH$_3$), 4.00 (s, 3H, OCH$_3$), 6.70 (s, 1H Ar), 6.79 (s, 1H Ar), 7.23–7.62 (m, 10H Ar). Mass: (M+H)$^+$=401.15

3,5-diphenyl-8-ethoxy-1-ethyl-7-methoxy-1,3-dihydro-2H-1,4-benzodiazepin-2-one, IIdk.

By replacing 5-(4-bromophenyl)-7,8-dimethoxy-1,3-dihydro-2H-1,4-benzodiazepin-2-one (XXIIaf) in example IIba by 3,5-diphenyl-8-ethoxy-7-methoxy-1,3-dihydro-2H-1,4-benzodiazepin-2-one (XXIIba), and methyl iodide by ethyl iodide, and proceeding in the same manner, the abovenamed product is obtained. Yield: 65%. M: 178–180° C. $^1$H-NMR (CDCl$_3$, 300 MHz): d 1.06–1.11 (m, 3H, NCH$_2$CH$_3$), 1.55–1.59 (m, 3H, OCH$_2$CH$_3$), 3.77 (s, 3H, OCH$_3$), 4.19–4.26 (m, 2H, OCH$_2$), 4.01 (AB system, ? d=0.70, J$_{AB}$=13.7, 2H, NCH$_2$), 6.77 (s, 1H Ar), 6.92 (s, 1H Ar), 7.35–7.74 (m, 10H Ar).

7-methoxy-1-methyl-5-phenyl-1,3-dihydro-2H-1,4-benzodiazepin-2-one, IIdl.

By replacing 7,8-dimethoxy-5-phenyl-1,3-dihydro-1,4-benzodiazepin-2-one (XXIIaa) in the example by 7-methoxy-5-phenyl-1,3-dihydro-2H-1,4-benzodiazepin-2-one (XXIIao), and ethylene-carbonate by iodomethane, and proceeding in the same manner, the abovenamed product is obtained. Yield: 55%. M: 10–112° C. $^1$H-NMR (CDCl$_3$, 300 MHz): d 3.38 (s, 3H, NCH$_3$), 3.75 (s, 3H, OCH$_3$), 4.30 (AB system, ? d=1.00, J$_{AB}$=10.6, 2H, —CH$_2$), 6.77–6.78 (m, 1H Ar), 7.09–7.14 (m, 1H Ar), 7.31 (s, 1H Ar), 7.38–7.46 (m, 3H Ar), 7.44–7.67 (m, 2H Ar).

8-methoxy-1-methyl-5-phenyl-1,3-dihydro-2H-1,4-benzodiazepin-2-one, IIdm.

By replacing 7,8-dimethoxy-5-phenyl-1,3-dihydro-1,4-benzodiazepin-2-one (XXIIaa) in the example by 7-methoxy-5-phenyl-1,3-dihydro-2H-1,4-benzodiazepin-2-one (XXIIan), and ethylene carbonate by iodomethane, and proceeding in the same manner, the abovenamed product is obtained. Yield: 76%. M: 114–116° C. $^1$H-NMR (CDCl$_3$, 300 MHz): d 3.41 (s, 3H, NCH$_3$), 3.90 (s, 3H, OCH$_3$), 4.29 (AB system, ? d=0.99, J$_{AB}$=10.6, 2H, —CH$_2$), 6.71–6.75 (m, 1H Ar), 6.81–6.82 (m, 1H Ar), 7.22–7.25 (m, 1H Ar), 7.36–7.42 (m, 3H Ar), 7.50–7.62 (m, 2H Ar).

EXAMPLE 5

Pharmacological Activity: Inhibition of Phosphodiesterases 5.1. Isolation of phosphodiesterases from smooth muscle A 3 g segment of bovine aortic media cut into pieces with scissors was homogenized with an ultra-turrax then a potter glass/glass homogenizer in 7 volumes by weight of buffer A containing a protease inhibitor cocktail (20 mM Tris-HCl, 0.25 M saccharose, 2 mM magnesium acetate, 1 mM dithiothreitol, 5 mM EGTA, 2000 U/ml aprotinin, 10 mg/l leupeptin and 10 mg/l soya trypsic inhibitor). The homogenizate was centrifuged at 105,000 g for 1 hour. The supernatant was loaded on a DEAE-Sephacel column (15× 1.6 cm) pre-equilibrated with buffer B (buffer A without the saccharose, EGTA and protease inhibitors). The column was washed until there was no detectable absorption at 280 nm, then eluted with a linear gradient of NaCl (0–0.5 M) in buffer B. 3-ml fractions were collected and enzyme activity was determined under the conditions described hereinafter to localize the different enzymes PDE1, PDE3, PDE4 and PDE5, which were aliquoted and frozen at −80° C. (Lugnier et al., *Biochem. Phamacol.*, 35 (1986) 1746–1751). PDE2 was prepared from bovine endothelial cells by the same methods (Lugnier and Schini, *Biochem. Pharmacol.* 1990, 39; 75–84).

5.2. Protocol for Measuring Phosphodiesterase Activity

Cyclic nucleotide phosphodiesterase activity was determined by a radioenzymatic method using tritium-labelled cyclic GMP or AMP (1 μM) as substrate (Lugnier et al., 1986). $^3$H-labelled adenosine or guanosine monophosphate formed by hydrolysis of the radiolabelled cyclic nucleotide was then converted to $^3$H-labelled adenosine or guanosine in a second reaction with one nucleotidase in excess. The nucleoside formed was separated from the nucleotides by anion exchange chromatography. Nucleoside radioactivity was determined by liquid scintillation counting. Enzymatic incubations were carried out under conditions allowing no more than 15% hydrolysis of the substrate; each point was performed in duplicate.

5.2.1. Determination of inhibition of PDE4

The concentration of substance which inhibits enzymatic activity by 50% (IC$_{50}$) at 1 μM cyclic AMP was calculated by nonlinear regression (Prism, GraphPad).

5.2.2. Selectivity

The activity of the compounds was evaluated on other phosphodiesterase isoforms, particularly basal state or calmodulin-activated PDE1 from vascular smooth muscle, basal state or cyclic GMP-activated PDE2 from vascular endothelial cells, PDE3 and PDE5 from vascular smooth muscle.

The results obtained are presented in Table 4 hereinafter and are expressed as the percentage inhibition of enzymatic activity produced by 10 μmol of the tested compound.

TABLE 1

Compounds represented by formula (III)

| Compound | PDE4 IC$_{50}$ (μM) or percentage inhibition at 10 μM |
|---|---|
| IIIaa | 9.3 |
| IIIab | 0.30 |
| IIIac | 33% |
| IIIad | 3.9% |
| IIIae | 19% |
| IIIaf | 30% |
| IIIag | 36% |
| IIIah | 3.1 |
| IIIai | 1.8 |
| IIIaj | 2.7 |
| IIIak | 1.8 |
| IIIal | 2.4 |
| IIIam | 1.7 |
| IIIan | 1.8 |
| IIIao | 1.7 |
| IIIap | 1.9 |
| IIIaq | 1.9 |
| IIIar | 2.9 |
| IIIas | 2.9 |
| IIIat | 2.3 |
| IIIau | 3.8 |
| IIIav | 0.9 |
| IIIaw | 16 |
| IIIax | 7.8 |
| IIIba | 6.9 |
| IIIbb | 0.087 |
| IIIzc | 0.72 |

TABLE 2

Compounds represented by formula (XXII)

| Compound | PDE4 IC$_{50}$ (μM) or percentage inhibition at 10 μM |
|---|---|
| XXIIaa | 25.8% |
| XXIIab | 10% |
| XXIIac | 35% |
| XXIIad | 14.9% |
| XXIIae | 21% |
| XXIIaf | 15 |
| XXIIag | 0.95 |
| XXIIah | 21.2% |
| XXIIai | 1.7 |
| XXIIaj | 4.4 |
| XXIIak | 13 |
| XXIIal | 23.9% |
| XXIIam | 0.7 |
| XXIIan | 12.1% |
| XXIIao | 11.5% |
| XXIIap | 36.10% |
| XXIIaq | 26.2% |
| XXIIar | 49.3% |
| XXIIas | 41.3% |
| XXIIat | 29% |
| XXIIau | 42.6% |
| XXIIav | 23% |
| XXIIaw | 4% |
| XXIIax | 6% |
| XXIIay | 19.6% |
| XXIIaz | 9.5 |
| XXIIba | 6.7 |
| XXIIbb | 15 |
| XXIIbc | 10% |

TABLE 3

Compounds represented by formula (II)

| Compound | PDE4 IC$_{50}$ (μM) or percentage inhibition at 10 μM |
|---|---|
| IIab | 38% |
| IIac | 2.3 |
| IIad | 23% |
| IIae | 3.4% |
| IIaf | 11.7% |
| IIag | 4.8 |
| IIah | 36% |
| IIai | 39% |
| IIaj | 7.9% |
| IIak | 16 |
| IIal | 10 |
| IIam | 20% |
| IIan | 3.6 |
| IIao | 1.6 |
| IIap | 18% |
| IIaq | 7.9 |
| IIar | 0% |
| IIas | 8.4 |
| IIat | 3.9% |
| IIau | 18.5% |
| IIav | 15% |
| IIaw | 10 |
| IIax | 8.2 |
| IIay | 6.6 |
| IIaz | 6.9% |
| IIba | 17 |
| IIbb | 3.13 |
| IIbc | 27.2% |
| IIbd | 34.3% |
| IIbe | 34.7% |
| IIbf | 0.86 |
| IIbg | 0.9/1.6 |
| IIbh | 2.4 |
| IIbi | 23.1% |
| IIbj | 6.5 |
| IIbk | 14.2% |
| IIbl | 15 |
| IIbm | 7.3 |
| IIbn | 2.95 |
| IIbo | 2.92 |
| IIbp | 5.74 |
| IIbq | 33.8% |
| IIbr | 6.6/3.8 |
| IIbs | 38.8% |
| IIbt | 38.4% |
| IIbu | 12.4/18.7 |
| IIbv | 44.4% |
| IIbw | 46.1% |
| IIbx | 18% |
| IIby | 8.2 |
| IIbz | 42.3% |
| IIca | 2.5 |
| IIcb | 28.5% |
| IIcc | 4.97 |
| IIcd | 20.1% |
| IIce | 0.88/1.4 |
| IIcf | 21% |
| IIcg | 6.7 |
| IIch | 9.6 |
| IIci | 1.45 |
| IIcj | 3.76 |
| IIck | 32.2% |
| IIcl | 4.3% |
| IIcm | 1.9 |
| IIcn | 45% |
| IIco | 34.3% |
| IIcp | 9.2 |
| IIcq | 7.4 |
| IIcr | 2.7 |
| IIcs | 1.25 |
| IIct | 18% |
| IIcu | 4.8 |
| IIcv | 3.1 |

TABLE 3-continued

Compounds represented by formula (II)

| Compound | PDE4 IC$_{50}$ (μM) or percentage inhibition at 10 μM |
|---|---|
| IIcw | 9.4% |
| IIcx | 9.9% |
| IIcy | 2.8 |
| IIcz | 4.4 |
| IIda | 0.55 and 0.43 |
| IIdb | 23 |
| IIdc | 5.1 |
| IIdd | 31.5% |
| IIde | 0% |
| IIdf | 1.5 |
| IIdg | 1.1 |
| IIdh | 0.52 |
| IIdi | 8.15 |
| IIdj | 48.3% |
| IIdk | 1.1 |
| IIdl | 34.6% |
| IIdm | 16% |

TABLE 4

Selectivity

IC$_{50}$ (μM) or percentage inhibition at 10 μM

| Compound | PDE1 | PDE2 | PDE3 | PDE4 | PDE5 |
|---|---|---|---|---|---|
| IIIab | 3.81 | 16 | 5.8 | 0.30 | 4.3 |
| IIIav | 49% | 19 | 92% | 0.9 | 40 |
| IIIbb | 14 | 25% | 2.7 | 0.087 | 5.7 |
| IIIzc | 32% | 24% | 36% | 0.72 | 38% |
| XXIIag | 46% | 17% | 22% | 0.95 | 35% |
| IIbg | 47% | 20% | 40% | 0.9 | — |
| XXIIai | 55% | 6% | 55% | 1.7 | — |
| XXIIam | 29% | 36% | 36% | 0.7 | 35% |
| IIda | 26% | 7% | 47% | 0.5 | 14% |

All the compounds tested showed potent inhibition of PDE4. The preferred compounds according to the invention have an excellent potency and selectivity profile towards phosphodiesterase 4, in so far as these compounds are weaker inhibitors of the other PDEs, particularly PDE3.

EXAMPLE 6

Anti-Inflammatory Properties of the Inventive Compounds

Compounds according to the invention were assessed for anti-inflammatory properties on mononuclear cells from venous blood of healthy donors (n=4), by a protocol approved by the Alsace No. 1 Ethics Committee. More specifically, the cells were incubated for 24 hours in 24-well plates in the presence of the test compound, after activation by *Salmonella Abortis Equi* lipopolysaccharide (LPS) (5 pg/ml) (cf. De Groote et al., *Cytokine* 4, 1992, 239). After incubation, TNFα concentrations were determined in the culture supernatant by an ELISA method (Antibody Solutions, Half Moon Bay, Calif., USA).

The results obtained revealed that the test compounds produced a marked, dose-related inhibition of TNFα, and only TNFα, production (relative to IL1β, IL6 and IL8 which were not significantly decreased). As an example, compounds IIIab and IIda at a concentration of 1 μM, inhibited TNFα production by 100%, whereas at this same concentration, IL1β, IL6 and IL8 secretion levels were not at all altered.

Other compounds found to be potent inhibitors of PDE4, such as for example compounds IIdh, XXIIag, also have potent anti-TNFα activity, with IC$_{50}$ values comprised between 1 and 0.1 μM. Some such compounds, for instance compound XXIIag, are capable of inhibiting the secretion of TNFα, but also of IL1β, and display a pharmacological profile distinct from the selective anti-TNFα compounds.

The invention claimed is:

1. A compound represented by formula (I)

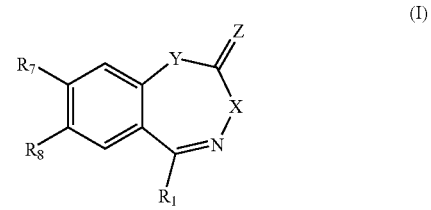

(I)

wherein:
X represents a CR$_4$R$_4$' group and Y represents an NR$_6$ group, R$_4$, R$_4$' and R$_6$ being defined hereinafter,
Z represents an oxygen atom,
R$_1$ is a (C$_1$–C$_{12}$)alkyl, (C$_3$–C$_6$)cycloalkyl, (C$_6$–C$_{18}$)aryl, (C$_6$–C$_{18}$)aryl(C$_1$–C$_4$)alkyl, (C$_1$–C$_{12}$)alkyl(C$_6$–C$_{18}$)aryl group, a (C$_5$–C$_{18}$)heterocycle, aromatic or not, containing 1 to 3 heteroatoms, or an OR$_2$, SR$_2$ or NR$_2$R$_3$ group in which (i) R$_2$ and R$_3$, independently of each other, are selected in the group consisting of a hydrogen atom, a (C$_1$–C$_6$)alkyl, (C$_3$–C$_6$)cycloalkyl, (C$_6$–C$_{12}$)aryl group, and a (C$_5$–C$_{12}$)heterocycle, aromatic or not, containing 1 to 3 heteroatoms or, (ii) R$_2$ and R$_3$ together form a linear or branched hydrocarbon having from 2 to 6 carbon atoms, possibly containing one or more double bonds and/or possibly interrupted by an oxygen, sulfur or nitrogen atom;
R$_4$ and R$_4$', which are the same or different are selected in the group consisting of the hydrogen atom and a (C$_1$–C$_{12}$)alkyl, (C$_6$–C$_{18}$)aryl, (C$_2$–C$_6$)alkenyl, (C$_3$–C$_6$) cycloalkyl, (C$_6$–C$_{18}$)aryl(C$_1$–C$_4$)alkyl, (C$_1$–C$_{12}$)alkyl (C$_6$–C$_{18}$)aryl group or a (C$_5$–C$_{18}$)heterocycle, aromatic or not, containing 1 to 3 heteroatoms, (C$_2$–C$_6$)alkynyl, NO$_2$, CF$_3$, CN, NR'R", SR', OR', COOR', CONR'R" and NHCOR'R" group, R' and R", independently of each other, being selected in the group consisting of the hydrogen atom, a (C$_1$–C$_6$)alkyl, (C$_1$–C$_6$)alkoxy, (C$_3$–C$_6$)cycloalkyl, (C$_6$–C$_{12}$)aryl group, and a (C$_5$–C$_{12}$)heterocycle, aromatic or not, containing 1 to 3 heteroatoms;
R$_6$ is selected from the group consisting of the hydrogen atom, (C$_1$–C$_6$)alkyl, (C$_6$–C$_{18}$)aryl, (C$_6$–C$_{18}$)aryl (C$_1$–C$_4$)alkyl, and (C$_1$–C$_{12}$)alkyl(C$_6$–C$_{18}$)aryl;
R$_7$ and R$_8$ represent an ethoxy group;
the alkyl, alkenyl, alkynyl, alkylaryl, aralkyl, cycloalkyl, aryl, heterocycle groups and the hydrocarbon chain defined hereinabove possibly being substituted by one or more substituents, which are the same or different, selected in the group consisting of a halogen atom, a (C$_1$–C$_{12}$)alkyl, (C$_6$–C$_{18}$)aryl, (C$_2$–C$_6$)alkenyl, (C$_2$–C$_6$) alkynyl, heterocycle, OH, =O, NO$_2$, NR'R", CN, CF$_3$, COR', COOR', (C$_1$–C$_6$)alkoxy, (di)(C$_1$–C$_6$)alkylamino, NHCOR' and CONR'R" group, in which R' and R" are defined as hereinabove,
and the salts thereof.

2. The compound according to claim 1 wherein $R_6$ represents the hydrogen atom or a $(C_1–C_6)$alkyl group.

3. The compound according to claim 1 wherein $R_4$ and $R_4'$, which are the same or different, represent a $(C_1–C_{12})$alkyl or $(C_6–C_{18})$aryl$(C_1–C_4)$alkyl group, possibly substituted by one or more substituents, which are the same or different, chosen from among a halogen atom and an OH, =O, $NO_2$, $NH_2$, CN, $CF_3$, COR', COOR', $(C_1–C_6)$alkoxy, (di)$(C_1–C_6)$alkylamino, NHCOR' and CONR'R" group, in which R' and R" are defined as in claim 1.

4. The compound according to claim 1 wherein $R_4$ and $R_4'$ represent the hydrogen atom.

5. The compound according to claim 1, wherein $R_6$ represents the hydrogen atom or a $(C_1–C_6)$alkyl group and $R_4$ and $R_4'$ represent the hydrogen atom.

6. The compound according to claim 1 wherein $R_1$ is a $(C_6–C_{18})$aryl, $(C_6–C_{18})$aryl$(C_1–C_4)$alkyl, $(C_1–C_{12})$alkyl $(C_6–C_{18})$aryl group or a $(C_5–C_{18})$heterocycle, aromatic or not, containing 1 to 3 heteroatoms, said group or heterocycle possibly being substituted.

7. The compound according to claim 1, wherein $R_1$ is a substituted or unsubstituted phenyl group.

8. The compound according to claim 1, wherein $R_1$ is an aromatic heterocycle optionally substituted by one or more groups chosen from among the following groups (a)–(d):
 (a) one or more halogen atoms,
 (b) a COR' group,
 (c) a trifluoromethyl group,
 (d) an alkyl or alkynyl group.

9. The compound according to claim 1, wherein $R_1$ is a 4-chlorophenyl, 3,4-dichlorophenyl, 2-naphthyl, 2-benzo[b]thienyl, 4-(2-furyl)phenyl, 3-pyridyl or 3-trifluoromethylphenyl group.

10. The compound according to claim 1 chosen among the following compounds:
 7,8-diethoxy-5-phenyl-1,3-dihydro-2H-1,4-benzodiazepin-2-one
 7,8-diethoxy-1-methyl-5-phenyl-1,3-dihydro-2H-1,4-benzodiazepin-2-one,
 7,8-diethoxy-1-ethyl-5-phenyl-1,3-dihydro-2H-1,4-benzodiazepin-2-one,
 ethyl (7,8-diethoxy-2-oxo-5-phenyl-2,3-dihydro-1H-1,4-benzodiazepin-1-yl)acetate,
 1-benzyl-7,8-diethoxy-5-phenyl-1,3-dihydro-2H-1,4-benzodiazepin-2-one,
 7,8-diethoxy-3-methyl-5-phenyl-1,3-dihydro-2H-1,4-benzodiazepin-2-one,
 3-benzyl-7,8-diethoxy-5-phenyl-1,3-dihydro-2H-1,4-benzodiazepin-2-one,
 3-benzyl-7,8-diethoxy-1-ethyl-5-phenyl-1,3-dihydro-2H-1,4-benzodiazepin-2-one,
 and the salts thereof.

11. The compound according to claim 1, wherein $R_1$ is a phenyl group substituted by:
 (a) one or more halogen atoms, or
 (b) a COR' group, or
 (c) a trifluoromethyl group, or
 (d) an alkyl or alkynyl group, or
 (e) an aryl group or heterocycle itself possibly substituted by one or more groups chosen from among the groups (a)–(d).

12. The compound according to claim 1, wherein $R_1$ is chosen from among naphthyl, thienyl, furyl, indolyl and pyridyl.

13. A composition comprising a compound according to claim 1 and a vehicle or excipient.

14. A method for preparing a compound according to claim 1 wherein Z is an oxygen atom by reacting a compound represented by formula (XVIII):

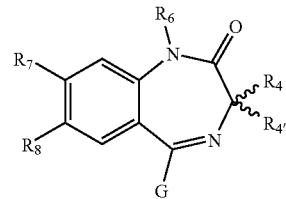

(XVIII)

wherein G is an activator group, with an acid compound of group $R_1$ in the presence of a palladium catalyst, $R_1$ being as defined in claim 1.

15. A method for preparing a compound according to claim 1 wherein Z is an oxygen atom by reacting a compound represented by formula (XXII):

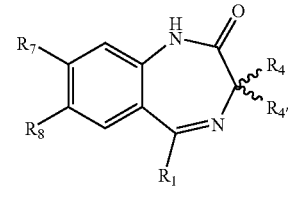

(XXII)

with an alkyl halogenide in the presence of a base.

16. The method of claim 14, wherein G is a halogen.

17. The method of claim 15, wherein the reaction is performed in a solvent.

18. The method of claim 15 or 17, wherein the reaction is performed at room temperature.

* * * * *